(12) United States Patent
Mabire et al.

(10) Patent No.: US 7,179,825 B2
(45) Date of Patent: Feb. 20, 2007

(54) RETINOIC ACID MIMETIC ANILIDES

(75) Inventors: Dominique Mabire, La Saussaye (FR);
Christophe Denis Adelinet, Iville (FR);
Imré Christian Csoka, Louviers (FR);
Marc Gaston Venet, Le Mesnil-Esnard (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/081,393

(22) Filed: Mar. 16, 2005

(65) Prior Publication Data
US 2005/0165018 A1 Jul. 28, 2005

Related U.S. Application Data

(62) Division of application No. 09/962,551, filed on Sep. 25, 2001, now Pat. No. 6,936,626, which is a division of application No. 09/555,775, filed on Jun. 1, 2000, now Pat. No. 6,319,939.

(30) Foreign Application Priority Data
Dec. 11, 1997 (EP) .................... 97203886

(51) Int. Cl.
C07D 213/02 (2006.01)
A61K 31/44 (2006.01)

(52) U.S. Cl. .............. 514/351; 514/381; 514/383; 514/400; 514/407; 514/427; 546/334; 548/253; 548/267.6; 548/338.5; 548/375.1; 548/561

(58) Field of Classification Search ............... 514/351, 514/381, 383, 400, 407, 427; 546/334; 548/253, 548/267.6, 338.5, 375.1, 561
See application file for complete search history.

(56) References Cited

U.S. PATENT DOCUMENTS 4,788,206 A 11/1988 Guthrie et al.

FOREIGN PATENT DOCUMENTS

| EP | 0260774 B1 | 3/1988 |
| EP | 0371559 B1 | 6/1990 |
| EP | 0371564 B1 | 6/1990 |
| JP | 52083565 | 7/1977 |
| WO | WO 97/16443 | 5/1997 |
| WO | WO 97/49704 | 12/1997 |

OTHER PUBLICATIONS

English Abstract of Japanese Patent JP52083565; Publication Date Jul. 12, 1977; Applicant Kyowa Hakko Kogyo KK.

*Primary Examiner*—Zinna N. Davis

(57) ABSTRACT

The present invention is concerned with compounds of formula

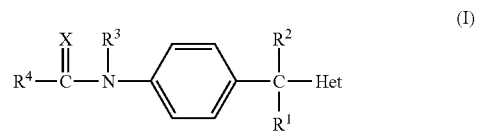

(I)

the N-oxides, the pharmaceutically acceptable addition salts and the stereochemically isomeric forms thereof, wherein X represents O, S or $NR^3$; $R^1$ represents hydrogen, hydroxy, $C_{1-6}$alkyl or aryl; $R^2$ represents hydrogen; optionally substituted $C_{1-12}$alkyl; $C_{3-7}$cycloalkyl; $C_{2-8}$alkenyl; aryl; $Het^1$; or $R^1$ and $R^2$ taken together may form a bivalent radical of formula —$(CH_2)_n$— wherein n is 2, 3, 4, 5 or 6; $R^3$ represents hydrogen, optionally substituted $C_{1-6}$alkyl, aryl, $Het^1$; $R^4$ represents hydrogen; hydroxy; mercapto; $C_{1-6}$alkyloxy; $C_{1-6}$alkylthio; aryloxy; arylthio; $Het^1$-oxy; $Het^1$-thio; optionally substituted $C_{1-12}$alkyl; optionally substituted $C_{2-8}$alkenyl; optionally substituted $C_{2-8}$alkynyl; optionally substituted $C_{3-7}$cycloalkyl; optionally substituted $C_{5-7}$cycloalkenyl; aryl; $Het^1$; or -Alk-$NR^3R^5$ (i) or —$NR^3R^5$ (ii) wherein Alk represents $C_{1-6}$alkanediyl; and $R^5$ represents hydrogen, $C_{1-6}$alkyl, aryl, $Het^1$, (aryl or $Het^1$)$C_{1-6}$alkyl, (aryl or $Het^1$)carbonyl or (aryl or $Het^1$)$C_{1-6}$alkyloxycarbonyl; aryl represents optionally substituted indanyl, indenyl, naphtyl, 5,6,7,8-tetrahydro-2-naphtalenyl or phenyl; Het represents an optionally substituted unsaturated heterocycle; and $Het^1$ represents an optionally substituted monocyclic or bicyclic heterocycle; having retinoic mimetic activity; their preparation, compositions containing them and their use as a medicine.

10 Claims, No Drawings

RETINOIC ACID MIMETIC ANILIDES

This application is a divisional of prior application U.S. Ser. No. 09/962,551, filed Sep. 25, 2001, now U.S. Pat. No. 6,936,626 which is a divisional of prior application U.S. Ser. No. 09/555,775, filed Jun. 1, 2000 now U.S. Pat. No. 6,319,939, the contents of both of which are hereby incorporated by reference.

The present invention concerns anilides, their N-oxides and addition salts; it further relates to processes for their preparation, compositions comprising them. The compounds of the present invention are potent inhibitors of the retinoic acid metabolism, and hence, their use as a medicine is also described.

EP-A-0,260,744, published on Mar. 23, 1988, discloses (1H-imidazol-1-ylmethyl) substituted benzimidazoles as inhibitors of the androgen formation from $C_{21}$-steroids, as inhibitors of the biosynthesis of thromboxane $A_2$, and also having the capability to increase the excretion of ureic acid. EP-A-0,371,559, published on Jun. 6, 1990, discloses said benzimidazoles and analogous benzotriazoles as potent suppressers of the plasma elimination of endogenously or exogenously administered retinoic acid.

Retinoic acid (RA) is a key molecule in the regulation of growth and differentiation of epithelial tissues. However, RA is very rapidly metabolized by a series of enzymatic reactions, which results in its deactivation. Inhibition of RA-metabolism leads to enhanced RA levels in plasma and tissue. Therefore, compounds with such an inhibitory action, also called retinoic mimetic activity, have therapeutic and/or preventive potential in the field of dermatology and oncology.

The present invention is concerned with compounds of formula

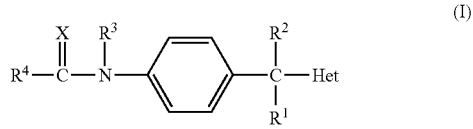

(I)

the N-oxides, the pharmaceutically acceptable addition salts and the stereochemically isomeric forms thereof, wherein:
X represents O, S or $NR^3$;
$R^1$ represents hydrogen, hydroxy, $C_{1-6}$alkyl or aryl;
$R^2$ represents hydrogen; $C_{1-12}$alkyl; $C_{3-7}$cycloalkyl; $C_{2-8}$alkenyl; aryl; $Het^1$; or $C_{1-12}$alkyl substituted with one or two substituents selected from $C_{3-7}$cycloalkyl, hydroxy, $C_{1-4}$alkyloxy, cyano, amino, mono- and di($C_{1-4}$alkyl)amino, mono- or di(aryl$C_{1-4}$alkyl)amino, di(aryl$C_{1-4}$alkyl)aminocarbonyloxy, ($C_{1-4}$alkyl) (aryl$C_{1-4}$alkyl) amino, mono- and di(aryl)amino, ($C_{1-4}$alkyl)(di($C_{1-4}$alkyl)-amino$C_{1-4}$alkyl)amino, pyrrolidinyl, piperidinyl, piperazinyl optionally substituted with $C_{1-4}$alkyl, morpholinyl, perhydro-azepinyl, carboxyl, $C_{1-4}$alkyloxycarbonyl, aminocarbonyl, mono- and di($C_{1-4}$alkyl)aminocarbonyl, aryl, aryloxy and arylthio; or
$R^1$ and $R^2$ taken together may form a bivalent radical of formula $-R^1-R^2-$ wherein $-R^1-R^2-$ represents $-(CH_2)_n-$ wherein n is 2, 3, 4, 5 or 6;
$R^3$ represents hydrogen, $C_{1-6}$alkyl, aryl, $Het^1$ or $C_{1-6}$alkyl substituted with aryl or $Het^1$;
$R^4$ represents hydrogen; hydroxy; mercapto; $C_{1-6}$alkyloxy; $C_{1-6}$alkylthio; aryloxy; arylthio; $Het^1$-oxy; $Het^1$-thio; $C_{1-12}$alkyl optionally substituted with one, two or three substituents each independently selected from halo, hydroxy, mercapto, $C_{1-6}$alkyloxy, $C_{1-6}$alkylthio, aryloxy, arylthio, $Het^1$-oxy, $Het^1$-thio, $C_{3-7}$cycloalkyl optionally substituted with hydroxycarbonyl$C_{1-6}$alkyl, carboxyl, $C_{1-6}$alkyloxycarbonyl, aryl$C_{1-6}$alkyloxy, aryl$C_{1-6}$alkylthio, aryl, $Het^1$; $C_{2-8}$alkenyl optionally substituted with one, two or three substituents selected from halo, $C_{3-7}$cycloalkyl, aryl, $Het^1$; $C_{2-8}$alkynyl optionally substituted with halo, $C_{3-7}$cycloalkyl, aryl; $C_{3-7}$cycloalkyl optionally substituted with $C_{1-6}$alkyl or aryl; $C_{5-7}$cycloalkenyl optionally substituted with $C_{1-6}$alkyl or aryl; aryl; $Het^1$; or $-Alk-NR^3R^5$ (i)

or $-NR^3R^5$ (ii)

wherein Alk represents $C_{1-6}$alkanediyl; and
$R^5$ represents hydrogen, $C_{1-6}$alkyl, aryl, $Het^1$, (aryl or $Het^1$)$C_{1-6}$alkyl, (aryl or $Het^1$)carbonyl or (aryl or $Het^1$)$C_{1-6}$alkyloxycarbonyl;
aryl represents indanyl, indenyl, naphtyl, 5,6,7,8-tetrahydro-2-naphtalenyl, phenyl; said indanyl, indenyl, naphtyl or phenyl may be substituted with one, two, three, four or five substituents each independently selected from hydroxy, halo, nitro, cyano, amino, azido, mono- or di($C_{1-6}$alkyl)amino, $C_{1-6}$alkylcarbonylamino, $C_{1-6}$alkyl, polyhalo$C_{1-6}$alkyl, hydroxy$C_{1-6}$alkyl, phenyl, phenyloxy, phenyl$C_{1-6}$alkyloxy, pyridinyl$C_{1-6}$alkyloxy, $C_{1-6}$alkyloxy, formyl, carboxyl and $C_{1-6}$alkylcarbonyl; or two adjacent carbon atoms on said phenyl may be substituted by a single bivalent radical having the formula $C_{1-12}$alkanediyl or polyhalo$C_{1-12}$alkanediyl;
Het represents an unsaturated heterocycle selected from pyrrolyl, pyrazolyl, imidazolyl, triazolyl, tetrazolyl and pyridinyl; each of said unsaturated heterocycles may optionally be substituted with amino, mercapto, $C_{1-6}$alkyl, $C_{1-6}$alkylthio or aryl; and
$Het^1$ represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3-triazinyl, 1,2,4-triazinyl, tetrahydropyranyl, pyranyl, morpholinyl and dioxanyl; each of said monocyclic heterocycles may be optionally substituted with one or two substituents each independently selected from $C_{1-4}$alkyl, hydroxy, amino, halo, aryl, arylcarbonyl or $C_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzoxathianyl, benzodioxanyl and benzodioxolanyl; each of said bicyclic heterocycles may be substituted with one or two substituents each independently selected from $C_{1-4}$alkyl, hydroxy, amino, halo, aryl, arylcarbonyl or $C_{1-4}$alkyloxycarbonyl.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{5-7}$cycloalkenyl is generic to cyclopentenyl, cyclohexenyl and cycloheptenyl; $C_{2-8}$alkenyl defines straight and branch chained hydro-carbon radicals containing one double bond and having from 2 to 8 carbon atoms such as, for example, ethenyl, 1-propenyl, 2-butenyl, 2-pentenyl, 3-pentenyl, 3-methyl-2-butenyl, 3-hexenyl, 3-heptenyl, 2-octenyl and the like; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; $C_{1-12}$alkyl is meant to include $C_{1-6}$alkyl and the higher homologues thereof having from 7 to 12 carbon atoms such as, for example, heptyl, octyl, nonyl, decyl, undecyl, dodecyl, 2-methylhexyl, 3-ethyloctyl and the like; $C_{1-12}$alkanediyl defines bivalent straight and branched chain saturated hydrocarbon radicals having from 1 to 12 carbon atoms such as, for example, 1,1-methanediyl, 1,2-ethanediyl, 1,3-propanediyl, 1,4-butanediyl, 1,5-pentanediyl, 1,6-hexanediyl, 1,2-propanediyl, 2,3-butanediyl, 1,7-heptanediyl, 1,8-octanediyl, 1,9-nonanediyl, 1,10-decanediyl, 1,11-undecanediyl, 1,12-dodecanediyl, 1,1,4,4-tetramethylbutane-1,4-diyl and the like; polyhalo$C_{1-6}$alkyl is defined as polyhalosubstituted $C_{1-6}$alkyl, in particular $C_{1-6}$alkyl substituted with 1 to 6 halogen atoms, more in particular difluoro- or trifluoromethyl; polyhalo$C_{1-12}$alkanediyl is defined as polyhalosubstituted $C_{1-12}$alkanediyl, in particular $C_{1-12}$alkanediyl substituted with 1 to 12 halogen atoms; triazolyl is meant to include 1,2,4-triazolyl and 1,3,4-triazolyl; tetrazolyl is meant to include 1H-tetrazolyl and 2H-tetrazolyl; benzodioxanyl is meant to include 2,3-dihydro-1,4-benzodioxinyl.

The unsaturated heteroaryl group represented by Het may be attached to the remainder of the molecule of formula (I) through any ring carbon or heteroatom as appropriate. Thus, for example, when the heteroaryl group is imidazolyl, it may be a 1-imidazolyl, 2-imidazolyl, 4-imidazolyl and 5-imidazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl.

The pharmaceutically acceptable addition salts as mentioned hereinabove are meant to comprise the therapeutically active non-toxic base and acid addition salt forms which the compounds of formula (I) are able to form. The acid addition salt form of a compound of formula (I) that occurs in its free form as a base can be obtained by treating said free base form with an appropriate acid such as an inorganic acid, for example, hydrohalic acid, e.g. hydrochloric or hydrobromic, sulfuric, nitric, phosphoric and the like acids; or an organic acid, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) containing acidic protons may be converted into their therapeutically active non-toxic base, i.e. metal or amine, addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore and hereinafter defines all the possible stereoisomeric forms in which the compounds of formula (I) exist. Unless otherwise mentioned or indicated, the chemical designation of compounds denotes the mixture, and in particular the racemic mixture, of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (I).

In particular, some of the compounds of formula (I) and some of the intermediates hereinafter have at least one stereogenic center in their structure. This stereogenic center may be present in a R and a S configuration, said R and S notation is used in correspondance with the rules described in Pure Appl. Chem., 1976, 45, 11–30.

Some of the compounds of formula (I) may also exist in their tautomeric forms. Such forms although not explicitly indicated in the above formula are intended to be included within the scope of the present invention. In particular, compounds of formula (I) wherein $R^3$ is hydrogen may exist in their corresponding tautomeric form.

Whenever used hereinafter, the term compounds of formula (I) is meant to include also the N-oxides, the pharmaceutically acceptable addition salts and all stereoisomeric forms.

Whenever used hereinafter, $R^1$ to $R^4$ and Het are defined as under formula (I) unless otherwise indicated.

A special group of compounds are those compounds of formula (I) wherein one or more of the following restrictions apply:

(a) X represents O, S, NH or N(aryl); more in particular X is O or S;

(b) $R^1$ represents hydrogen, hydroxy or $C_{1-6}$alkyl;

(c) $R^2$ represents hydrogen; $C_{1-12}$alkyl; $C_{3-7}$cycloalkyl; $C_{2-8}$alkenyl; aryl; Het$^1$; or $C_{1-12}$alkyl substituted with one or two substituents selected from hydroxy, $C_{1-4}$alkyloxy, cyano, mono- and di($C_{1-4}$alkyl)amino, mono- or di(aryl$C_{1-4}$alkyl)amino, di(aryl$C_{1-4}$alkyl)aminocarbonyloxy, ($C_{1-4}$alkyl)(aryl$C_{1-4}$alkyl)amino, ($C_{1-4}$alkyl)(di($C_{1-4}$alkyl)amino$C_{1-4}$alkyl)amino, piperidinyl, piperazinyl optionally substituted with $C_{1-4}$alkyl, morpholinyl, $C_{1-4}$alkyloxycarbonyl, aryl, aryloxy and arylthio; or
$R^1$ and $R^2$ taken together may form a bivalent radical of formula —$R^1$—$R^2$— wherein —$R^1$—$R^2$— represents —$(CH_2)_n$— wherein n is 2;

(d) $R^3$ represents hydrogen or $C_{1-6}$alkyl; more in particular $R^3$ is hydrogen;

(e) $R^4$ represents hydrogen; $C_{1-6}$alkyloxy; aryloxy; $C_{1-12}$alkyl optionally substituted with one, two or three substituents each independently selected from halo, hydroxy, $C_{1-6}$alkyloxy, $C_{1-6}$alkylthio, aryloxy, arylthio, Het$^1$-thio, $C_{3-7}$cycloalkyl optionally substituted with hydroxycarbonyl$C_{1-6}$alkyl, carboxyl, $C_{1-6}$alkyloxycarbonyl, aryl$C_{1-6}$alkylthio, aryl, Het$^1$; $C_{2-8}$alkenyl optionally substituted with one, two or three substituents selected from halo, $C_{3-7}$cycloalkyl, aryl, Het$^1$; $C_{2-8}$alkynyl optionally substituted with aryl; C$_{3-7}$cycloalkyl optionally substituted with C$_{1-6}$alkyl or aryl; C$_{5-7}$cycloalkenyl; aryl; Het$^1$; or

—Alk—NR$^3$R$^5$ (i)

or

—NR$^3$R$^5$ (ii)

wherein Alk represents C$_{1-6}$alkanediyl; and
R$^5$ represents hydrogen, C$_{1-6}$alkyl, aryl, Het$^1$, arylC$_{1-6}$alkyl, arylcarbonyl or arylC$_{1-6}$alkyloxycarbonyl.

Aryl is suitably indenyl, naphtyl, 5,6,7,8-tetrahydro-naphtalenyl, phenyl; said indenyl, naphtyl or phenyl may be substituted with one, two, three, four or five substituents each independently selected from hydroxy, halo, nitro, amino, azido, C$_{1-6}$alkylcarbonylamino, C$_{1-6}$alkyl, polyhaloC$_{1-6}$alkyl, phenyl, C$_{1-6}$alkyloxy.

Het is suitably imidazolyl, triazolyl and pyridinyl; each of said unsaturated heterocycles may optionally be substituted with C$_{1-6}$alkyl, more in particular, Het is 1H-1-imidazolyl or 1,2,4-triazol-1-yl.

Het$^1$ is suitably pyrrolyl, furanyl, thienyl, isoxazolyl, thiazolyl, piperidinyl, pyridinyl, piperazinyl, pyrimidinyl, pyrazinyl, morpholinyl and dioxanyl; each of said monocyclic heterocycles may be optionally substituted with one or two substituents each independently selected from C$_{1-4}$alkyl, hydroxy, amino, halo, aryl, arylcarbonyl or C$_{1-4}$alkyloxycarbonyl; or indolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, quinoxalinyl, 1,4-benzodioxinyl, benzodioxanyl and benzodioxolanyl; each of said bicyclic heterocycles may be substituted with one or two substituents each independently selected from C$_{1-4}$alkyl, hydroxy, amino, halo, aryl, arylcarbonyl or C$_{1-4}$alkyloxycarbonyl.

Particular compounds are those compounds of formula (I) wherein R$^2$ is C$_{1-12}$alkyl optionally substituted with mono- and di(C$_{1-4}$alkyl)amino, more in particular, R$^2$ is 3-pentyl, 2-propyl, 2-(dimethylamino)-ethyl or 2-(diethylamino)-ethyl.

Other particular compounds are those compounds of formula (I) wherein R$^4$ is C$_{1-12}$alkyl optionally substituted with one, two or three substituents each independently selected from halo, hydroxy, C$_{1-6}$alkyloxy, C$_{1-6}$alkylthio, aryloxy, arylthio, Het$^1$-thio, C$_{3-7}$cycloalkyl optionally substituted with hydroxycarbonylC$_{1-6}$alkyl, carboxyl, C$_{1-6}$alkyloxycarbonyl, arylC$_{1-6}$alkylthio, aryl, Het$^1$; aryl; Het$^1$; or a radical of formula (ii).

Preferred compounds are those compounds of formula (I) wherein R$^3$ is hydrogen; X is O and R$^4$ is aryl or C$_{1-12}$alkyl optionally substituted with one, two or three substituents each independently selected from halo, hydroxy, C$_{1-6}$alkyloxy, C$_{1-6}$alkylthio, aryloxy, arylthio, Het$^1$-thio, C$_{3-7}$cycloalkyl optionally substituted with hydroxycarbonylC$_{1-6}$alkyl, carboxyl, C$_{1-6}$alkyloxycarbonyl, arylC$_{1-6}$alkylthio, aryl, Het$^1$; or a radical of formula (ii).

Other preferred compounds are those compounds of formula (I) wherein R$^3$ is hydrogen, X is S and R$^4$ is a radical of formula (ii).

More preferred are the compounds of formula (I) wherein X is O; Het is 1,2,4-triazol-1-yl; R$^1$ and R$^3$ are hydrogen; R$^2$ is C$_{1-6}$alkyl optionally substituted with dialkylamino; and R$^4$ is C$_{1-4}$alkyl optionally substituted with one, two or three substituents each independently selected from halo, hydroxy, C$_{1-6}$alkyloxy, C$_{1-6}$alkylthio, aryloxy, arylthio, Het$^1$-thio, C$_{3-7}$cycloalkyl optionally substituted with hydroxycarbonylC$_{1-6}$alkyl, carboxyl, C$_{1-6}$alkyloxycarbonyl, arylC$_{1-6}$alkylthio, aryl or Het$^1$.

Most preferred are 4-chloro-N-[4-[2-ethyl-1-(1H-1,2,4-triazol-1-yl)butyl]phenyl]-α-hydroxybenzeneacetamide; the N-oxides, the pharmaceutically acceptable addition salts and stereoisomeric forms thereof.

In general, the compounds of formula (I) can be prepared by reacting an intermediate of formula (II) wherein W$^1$ is an appropriate leaving group such as, for example, a halogen, hydroxy or an alkylsulfonyloxy group, with an intermediate of formula (III) or a functional derivative thereof. For instance, a functional derivative of imidazole may be 1,1'-carbonyldiimidazole.

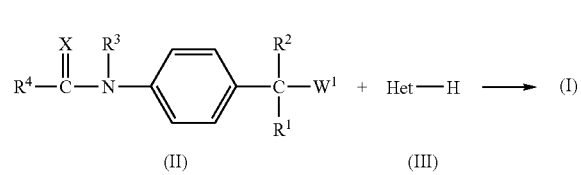

Said reaction may be performed in a reaction-inert solvent such as, for example, acetonitrile, dichloromethane or tetrahydrofuran, in the presence of a suitable base such as, for example, potassium carbonate. In case W$^1$ is an hydroxy group, it may be convenient to perform the above reaction in the presence of triphenylphosphine and diethyl azodicarboxylate or a functional derivative of any of said reagents, or in the presence of 1-hydroxy-1H-benzotriazole and dicyclohexylcarbodiimide.

In this and the following preparations, the reaction products may be isolated from the reaction medium and, if necessary, further purified according to methodologies generally known in the art such as, for example, extraction, crystallization, distillation, trituration and chromatography.

Alternatively, compounds of formula (I) may be prepared by N-alkylation of an intermediate of formula (IV) with an intermediate of formula (V) wherein W$^2$ is an appropriate leaving group such as, for example, hydroxy, a phenoxy group or a halogen, in a reaction-inert solvent such as, for example, water, N,N-dimethylformamide, dichloromethane, 1,2-dichloroethane, chloroform, N,N-dimethylacetamide, 2-propanone, benzene or the like, and optionally in the presence of a suitable base such as, for example, triethylamine, pyridine or sodiumcarbonate.

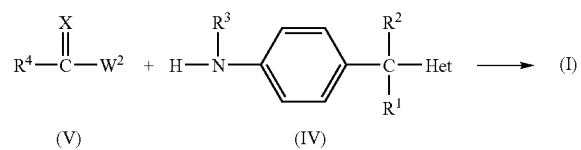

Also functional derivatives of intermediates of formula (V) may be used such as, for example, an anhydride, e.g. glutaric anhydride, dihydro-2H-pyran-2,6(3H)-dione, acetic acid anhydride; a cyanate; a thiocyanate; an isocyanate or an isothiocyanate. In some instances, it may be convenient to add an acid to the reaction medium such as, for instance, acetic acid may be used together with a cyanate.

Compounds of formula (I) wherein R$^4$ is a Het$^1$C$_{1-12}$alkyl or a radical of formula (i), said R$^4$ being represented by R$^{4'}$ and said compounds being represented by formula (I-a), can be prepared by reacting an intermediate of formula (VI) wherein W$^3$ is a suitable leaving group such as, for example, a halogen, with an intermediate of formula $R^{4'}$—H (VII) in a reaction-inert solvent such as, for example, acetonitrile, and in the presence of an appropriate base such as, for example, potassium carbonate.

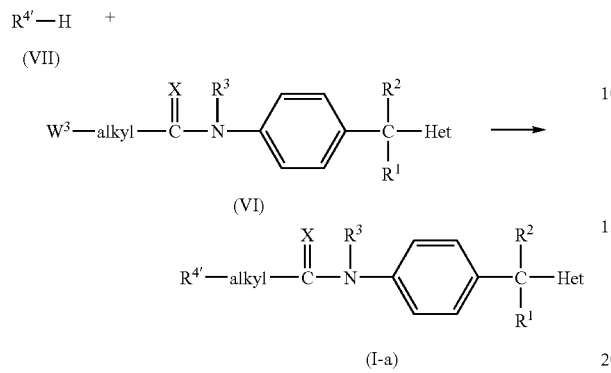

Compounds of formula (I) wherein $R^1$ is hydroxy, said compounds being represented by formula (I-b), may be prepared by reacting an intermediate of formula (VIII) with Het-H (III) or a functional derivative thereof, in the presence of an appropriate reagent such as, for example, n-butyl-lithium, in a reaction-inert solvent such as tetrahydrofuran and diethylether, and optionally in the presence of chlorotriethylsilane.

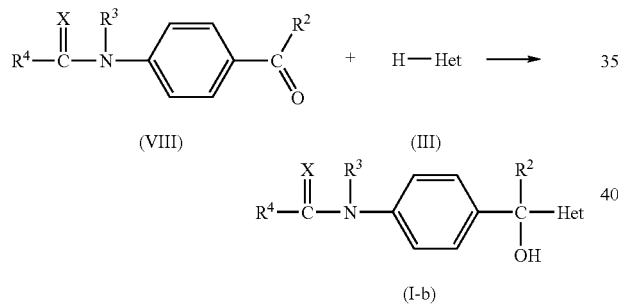

Compounds of formula (I) wherein $R^3$ is hydrogen and $R^4$ is attached by a nitrogen atom to the remainder of the molecule, said compounds being represented by formula (I-c), may be prepared by reacting a primary or secondary amine of formula (VIII) with an intermediate of formula (IX) in a reaction-inert solvent such as, for example, acetonitrile.

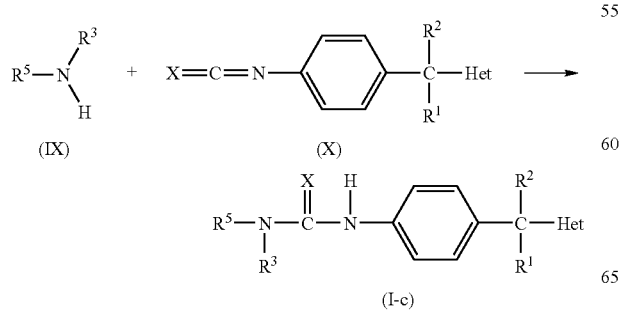

Compounds of formula (I) wherein $R^2$ is optionally substituted hydroxymethyl, being represented by formula (I-d), may be prepared by reacting an intermediate of formula (XI) with Het-H (XII) or a functional derivative thereof, in a reaction-inert solvent such as, for example N,N-dimethylformamide.

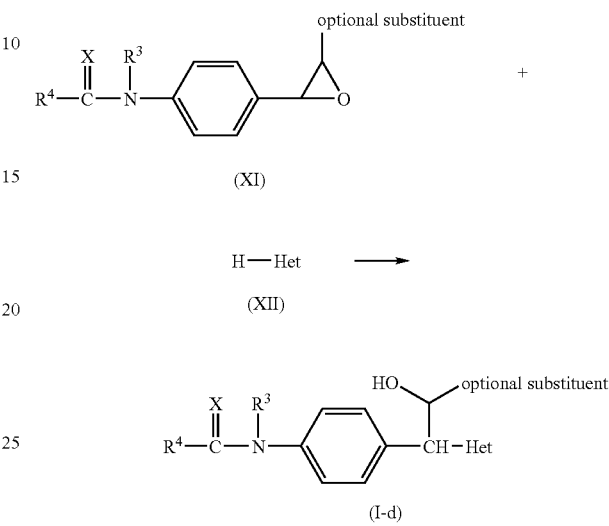

Compounds of formula (I) can also be prepared by reacting an intermediate of formula (XIII) wherein $W^4$ is a suitable leaving group such as, for example, hydroxy, with an intermediate of formula (XIV) in an appropriate solvent such as, for example, acetic acid, and in the presence of an acid such as, for example, concentrated sulfuric acid.

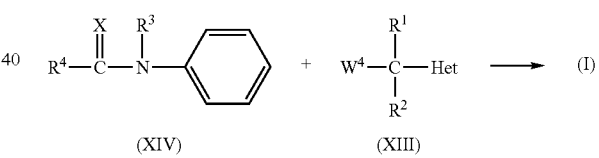

Compounds of formula (I) wherein $R^2$ is $C_{1-4}$alkyloxy $C_{1-12}$alkyl can be prepared by reacting an intermediate corresponding to a compound of formula (I) wherein $R^2$ is LG—$C_{1-12}$alkyl wherein LG is an appropriate leaving group such as, for example, a alkylsulfonyloxy group, with $C_{1-4}$alkylO$^-$M$^+$ wherein M$^+$ is a suitable metal ion such as, for example Na$^+$, in a suitable solvent such as methanol.

Compounds of formula (I) wherein $R^2$ is optionally substituted $C_{1-12}$alkyl, said $R^2$ being represented by $R^{2'}$ and said compounds being represented by formula (I-e), can be prepared by reducing an intermediate of formula (XV) using a suitable reducing agent such as, for example, sodiumborohydride, in a suitable solvent such as methanol.

-continued

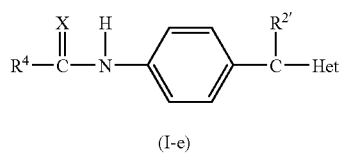

(I-e)

Compounds of formula (I) wherein $R^1$, $R^3$ and $R^4$ are hydrogen, said compounds being represented by formula (I-f), can be prepared by reacting an intermediate of formula (XXIII) with formamide in the presence of an acid such as, for example, acetic acid.

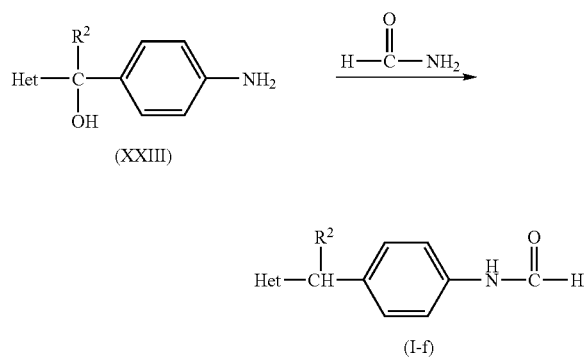

The compounds of formula (I) can also be converted into each other following art-known procedures of functional group transformation.

For example, compounds of formula (I) wherein $R^3$ is hydrogen may be converted to compounds of formula (I) wherein $R^3$ is other than hydrogen using art-known techniques.

Compounds of formula (I) containing an aliphatic double bond may be converted to compounds of formula (I) wherein said aliphatic double bond is reduced to a single bond using art-known hydrogenation techniques such as, for example, a reaction with hydrogen in methanol in the presence of palladium on activated charcoal as catalyst.

Compounds of formula (I) containing a carboxyl group may be esterified using art-known esterification techniques. Conversely, compounds of formula (I) containing ester may be hydrolysed to compounds of formula (I) containing the corresponding carboxyl moiety.

Also, compounds of formula (I) containing a $C_{1-6}$alkyloxycarbonyl substituent, may be transformed to compounds of formula (I) wherein said substituent is reduced to hydroxymethyl using for instance, lithium aluminium hydride in tetrahydrofuran; and if desired, said hydroxymethyl substituent may be further transformed to a formyl group. Said $C_{1-6}$alkyloxycarbonyl may also be entirely removed. Analogously, other moieties which may serve the purpose of protective group such as, for example, phenylmethyl, may also be removed using art-known techniques.

Compounds of formula (I) wherein $R^1$ is hydroxy can be converted to compounds of formula (I) wherein $R^1$ is hydrogen using a suitable reagent such as stannous chloride.

Compounds of formula (I) wherein $R^4$ is a phenoxy group may be converted to the ureum derivatives thereof using art-known replacement techniques. For instance, a primary or secundary amine may be used optionally in the presence of dimethylaminopyridine and a base such as triethylamine, and 1,4-dioxane may be used as solvent.

Compounds of formula (I) wherein X is O may be converted to compounds of formula (I) wherein X is S using art-known techniques such as, for example, the use of phosphorous pentasulfide in pyridine.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase such as, for example, a Chiracel AD column.

Some of the intermediates and starting materials are known compounds, may be commercially available or may be prepared according to art-known procedures.

In particular, intermediates of formula (II) wherein $R^1$ is hydrogen and $W^1$ is hydroxy, said intermediates being represented by formula (II-1), may be prepared by reducing a ketone of formula (VIII). The reduction may be performed in the presence of a suitable reducing agent in an appropriate reaction-inert solvent such as, for example, sodiumborohydride in methanol or lithiumaluminiumhydride in tetrahydrofuran and water.

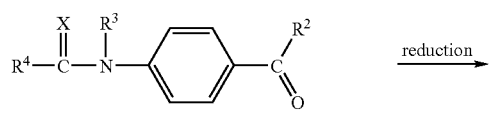

(VIII)

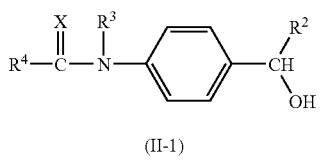

(II-1)

In some instances, it may be convenient to replace the hydroxy group in intermediates of formula (II-1) by another leaving group such as, for example, a halogen or a sulfonyl derivative, e.g. a p-toluenesulfonyloxy group or a alkylsulfonyloxy group, thus forming intermediates of formula (II-2) or (II-3). Said reaction can be performed in a reaction-inert solvent, such as, for example, chloroform, and in the presence of a suitable reagent such as, for example, thionylchloride or methylsulfonyl chloride.

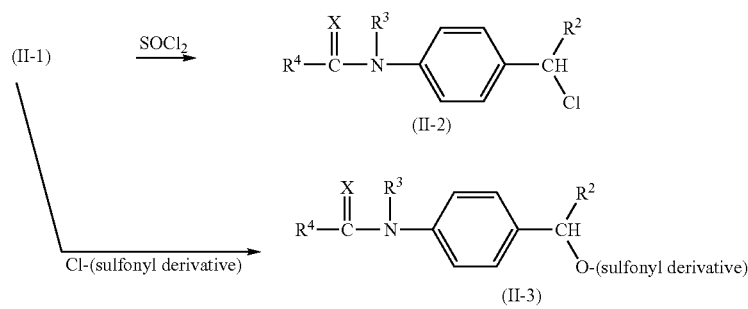

Intermediates of formula (IV) may be prepared by reacting an intermediate of formula (XVI), wherein P is a protective group such as, for example, $C_{1-4}$alkylcarbonyl, benzoyl or $C_{1-4}$alkyloxycarbonyl, with an intermediate of formula (III), and by subsequently reacting the thus formed amide derivative with an acid such as, for example, hydrochloric acid. The preparation of the intermediate amide derivative may be performed using the same procedure as the one used for the preparation of compounds of formula (I) starting from an intermediate of formula (II) and (III).

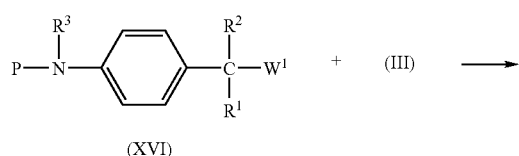

(XVI)

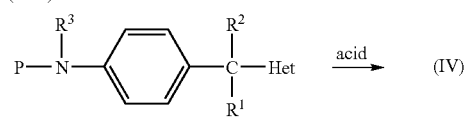

Intermediates of formula (IV) wherein $R^3$ is hydrogen, said intermediates being represented by formula (IV-1), may be prepared by reducing a nitro derivative of formula (XVII). Said reduction may be performed in the presence of a suitable reducing agent such as, for example, hydrogen, in an appropriate solvent such as, for example, methanol and in the presence of a suitable catalyst such as, for example, raney nickel.

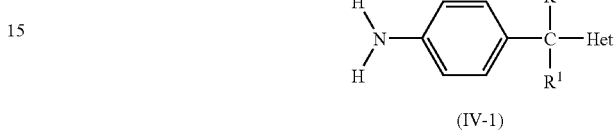

(XVII)

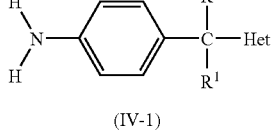

(IV-1)

Intermediates of formula (VI) can be prepared by further reacting an intermediate of formula (IV) with an intermediate of formula (XVIII) wherein $W^3$ is a suitable leaving group such as, for example, a halogen, in a reaction-inert solvent such as, for example, dichloromethane, and in the presence of a base such as, for example, sodium carbonate.

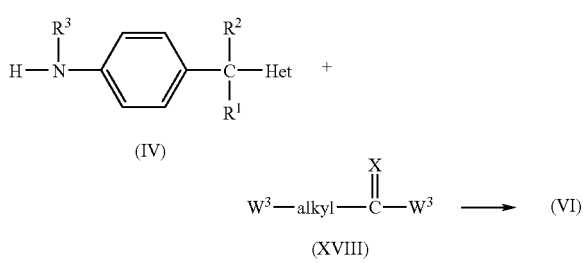

Intermediates of formula (X) may be prepared by reacting an intermediate of formula (IV-1) with a reagent of formula (XIX) in a reaction inert solvent such as, for example, dichloromethane, and in the presence of a suitable base such as, for example, sodium hydroxide.

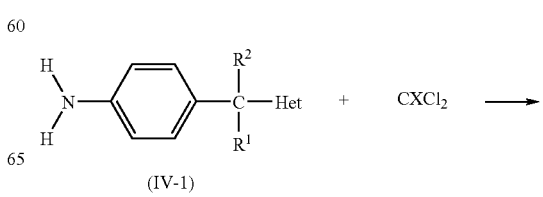

(IV-1)

-continued

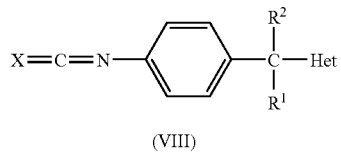

(VIII)

Intermediates of formula (XI) may be prepared by reductively reacting intramolecularly an intermediate of formula (XX) wherein $W^4$ is a suitable leaving group such as, for example, a halogen in the presence of a suitable reagent such as, for example, sodiumborohydride, in a reaction inert solvent such as, for example, methanol, and in the presence of a suitable base such as, for example, sodium hydroxide.

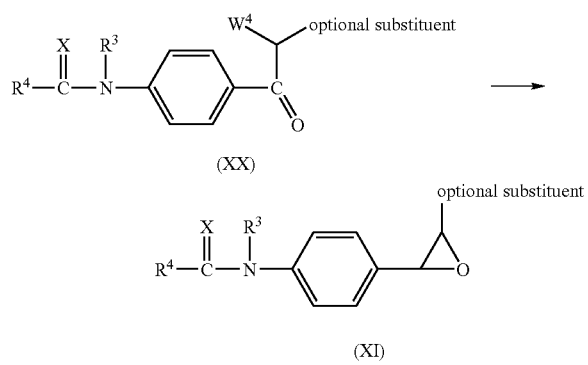

Intermediates of formula (XI) can be prepared by first dehydrating and deprotecting an intermediate of formula (XXI) wherein P is a protecting group such as, for example, $C_{1-4}$alkylcarbonyl, benzoyl or $C_{1-4}$alkyloxycarbonyl, using a suitable reagent such as, for example, an acid, e.g. hydrochloric acid, thus forming an intermediate of formula (XXII). Consequently, said intermediate of formula (XXII) may be further reacted with an intermediate of formula (V) in the same manner as described for the reaction between intermediates (IV) and (V).

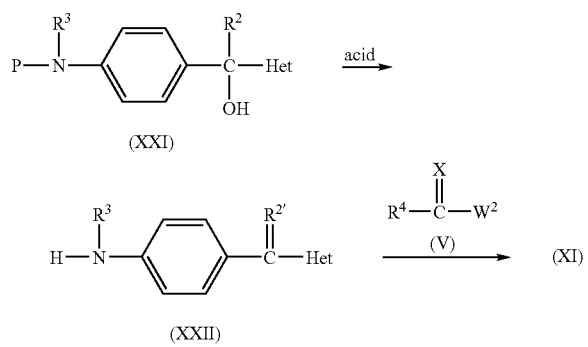

Intermediates of formula (XXIII) can be prepared by first reacting an intermediate of formula (XXIV) with Het-H (III) or a functional derivative thereof, in the presence of an appropriate reagent such as, for example, n-butyllithium, in a reaction-inert solvent such as tetrahydrofuran and diethylether, and optionally in the presence of chlorotriethylsilane. The thus formed nitro derivative of formula (XXV) may then be reduced using for example a 15% solution of $TiCl_3$ in water as reducing agent in a suitable solvent such as, for example, tetrahydrofuran.

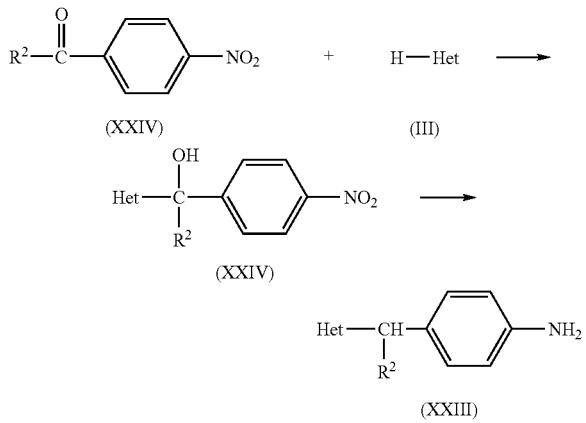

The compounds of formula (I) suppress the plasma elimination of retinoids, such as all-trans-retinoic acid, 13-cis retinoic acid and their derivatives, resulting in more sustained plasma and tissue concentrations of retinoic acid and improved control of the differentiation and growth of various cell types. This action of the present compounds is also called retinoic mimetic activity because administering a compound of formula (I) causes the same effect as if retinoids were administered. As such, the present compounds can be used to control the rate of growth and differentiation of normal, preneoplastic and neoplastic cells, whether they are epithelial or mesenchymal; whether they are of ectodermal, endodermal or mesodermal origin.

The property to delay the metabolism of retinoic acid can be evidenced in various in vitro and in vivo experiments. A particular in vitro procedure is described in example C.1 and tests the inhibitory activity of the compounds of formula (I) on the metabolism of retinoic acid in human breast cancer cells. The compounds of the present invention were also effective in suppressing induced vaginal keratinization effects in ovariectomized rats as is described in example C.2.

In addition, the compounds of formula (I) show little or no endocrinological side-effects and they have good oral availability.

In view of the above described pharmacological properties, in particular their retinoic mimetic activity, the present compounds are useful in the treatment and/or the prevention of disorders characterized by abnormal proliferation and/or abnormal differentiation of cells, in particular of cells of which the growth and differentiation is sensitive to the actions of retinoids. Such disorders are situated in the field of oncology, for example, head- and neck cancer, lung cancer, breast cancer, uterine cervix cancer, gastrointestinal tract cancer, skin cancer, bladder cancer and prostate cancer and similar disorders; and in the field of dermatology, for example, keratinization disorders such as rosacea, acne, psoriasis, severe psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, melasma, hyperpigmentation and similar disorders.

Further, the compounds of formula (I) are useful in suppressing the metabolism of exogenously administered and of endogenously formed 1α,25-dihydroxy-vitamin $D_3$ (calcitriol). The inhibitory activity of the compounds of formula (I) on the metabolic degradation of calcitriol may be evidenced by measuring the impact of said compounds on the calcitriol degradation in human foreskin keratinocytes, pig kidney cells and human hepatoma cells. In view of their inhibitory effect on the calcitriol metabolism, the compounds of formula (I) can be used in the treatment of vitamin D deficiency states. The "classic" application of vitamin D compounds lies in the field of metabolic bone disorders. Calcitriol has also been described to influence the effects and/or production of interleukins. Further, calcitriol is of use in the treatment of diseases characterized by abnormal cell proliferation and/or differentiation, in particular, keratinization disorders such as those described hereinabove (Bouillon et al., Endocrine Reviews, 1995, 16, 200–257).

In view of the above described uses of the compounds of formula (I), it follows that the present invention provides a method of treating warm-blooded animals suffering from diseases which are characterized by an abnormal proliferation and/or abnormal differentiation of normal, preneoplastic or neoplastic cells, whether they are epithelial or mesenchymal; whether they are of ectodermal, endodermal or mesodermal origin. Said method comprises the systemic or topical administration of a retinoic mimetic amount of a compound of formula (I) effective in treating the above described disorders, in particular oncology disorders and keratinization disorders, optionally in the presence of an effective amount of a retinoic acid, a derivative or a stereochemically isomeric form thereof. The present invention further concerns a method of treating patients suffering from a pathological condition which may be beneficially influenced by the administration of calcitriol or a prodrug thereof, in particular oncology disorders and keratinization disorders, said method consisting of administering to a patient (a) an effective amount of calcitriol or a prodrug thereof and (b) an effective amount of a compound of formula (I).

The compounds of formula (I) may conveniently be used in combination with a chemotherapeutic agent, in particular an anti-neoplastic agent such as, e.g. daunorubicin, doxorubicin, vincristine, vinblastine, etoposide, taxol, taxotere, dactinomycin, mitoxantrone, mitomycin, trimetrexate and the like. The combination may be administered separately, simultaneously, concurrently or consecutively, or the combination may also be presented in the form of one pharmaceutical formulation. Thus, the present invention also involves a pharmaceutical product comprising (a) a compound of formula (I) and (b) a chemotherapeutic agent, as a combined preparation for simultaneous, separate or sequential use in the therapeutic or prophylactic treatment of warm-blooded animals suffering from disorders characterized by abnormal proliferation and/or abnormal differentiation of cells. Such a product may comprise a kit comprising a container containing a pharmaceutical composition of a compound of formula (I), and another container comprising a pharmaceutical composition of the chemotherapeutic agent. The product with separate compositions of the two active ingredients has the advantage that appropriate amounts of each component, and timing and sequence of administration can be selected in function of the patient. The present invention further concerns a method of treating patients suffering from disorders characterized by abnormal proliferation and/or abnormal differentiation of cells, said method consisting of administering to a patient (a) an effective amount of a compound of formula (I) and (b) an effective amount of a chemotherapeutic agent.

Thus, the present invention also relates to compounds of formula (I) as defined hereinabove for use as a medicine, in particular, for use in the manufacture of a medicament for the treatment of oncology disorders and keratinization disorders. The present invention further relates to compounds of formula (I) as defined hereinabove in combination with a retinoic acid, a derivative or a stereochemically isomeric form thereof, or in combination with calcitriol or a prodrug thereof, or in combination with a chemotherapeutic agent, in particular an anti-neoplastic agent, for use as a medicine. For ease of administration, the subject compounds may be formulated into various pharmaceutical forms. As appropriate compositions there may be cited all compositions usually employed for systemically or topically administering drugs. To prepare the pharmaceutical compositions of this invention, a retinoic mimetic effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, as a spot-on or as an ointment. Addition salts of compounds of formula (I) due to their increased water solubility over the corresponding base form, are obviously more suitable in the preparation of aqueous compositions.

As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (included scored or coated tablets), capsules, pills, powder packets, wafers, injectable solutions or suspensions, teaspoonfuls, tablespoonfuls and the like, and segregated multiples thereof.

Other such compositons are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflamatory agents, antibacterials, antifungals, disinfectants, vitamins, sunscreens, antibiotics, or other anti-acne agents.

The present invention also provides particular pharmaceutical or cosmetical compositions which comprise a pharmaceutically acceptable carrier, an effective amount of a compound of formula (I) and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin.

Further, the invention also relates to particular pharmaceutical or cosmetical compositions which comprise a pharmaceutically acceptable carrier, an effective amount of a compound of formula (I) and an effective amount of calcitriol or a prodrug thereof. The latter compositions are particularly useful in treating keratinization disorders.

The invention also relates to a product containing retinoic acid or a derivative thereof and a compound of formula (I) as a combined preparation for simultaneous, separate or sequential use in dermatological or oncological disorders. The invention also relates to a product containing calcitriol or a prodrug thereof and a compound of formula (I) as a combined preparation for simultaneous, separate or sequential use in dermatological or oncological disorders. Such products may comprise, for example, a kit comprising a container with a suitable composition containing a compound of formula (I) and another container with a composition containing calcitriol or a retinoid Such a product may have the advantage that a physician can select on the basis of the diagnosis of the patient to be treated the appropriate amounts of each component and the sequence and timing of the administration thereof.

Those of skill in the treatment of the disorders described hereinabove could determine the effective therapeutic daily amount from the test results presented in the experimental part. An effective therapeutic daily amount would be from about 0.01 mg/kg to about 40 mg/kg body weight, more preferably from about 0.1 mg/kg to about 10 mg/kg body weight. It may be appropriate to administer the therapeutically effective dose once daily or as two, three, four or more sub-doses at appropriate intervals throughout the day. Said sub-doses may be formulated as unit dosage forms, for example, containing 0.1 mg to 500 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines. The following examples are intended to illustrate the scope of the present invention.

EXPERIMENTAL PART

Of some compounds of formula (I) the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. Said "A" and "B" forms of those compounds of formula (I) wherein two asymmetric carbon atoms are present were separated in their pure steroechemically isomeric forms and designated as "A1" and "A2", and "B1" and "B2", without further reference to the actual stereochemical configuration.

As used hereinafter, "THF" is defined as tetrahydrofuran, "EtOAc" is defined as ethylacetate, "DIPE" is defined as diisopropyl ether and "RT" is defined as room temperature.

A) PREPARATION OF THE INTERMEDIATE COMPOUNDS

Example A1

Methanesulfonyl chloride (0.308 mol) was added dropwise to a solution of N-[4-(1-hydroxy-2-methylpropyl)phenyl]acetamide (0.1514 mol) and triethylamine (0.308 mol) in $CH_2Cl_2$ (600 ml) and the mixture was stirred at 0° C. for 1 hour. The solvent was evaporated, yielding 44 g (100%) of (±)-4-(acetylamino)-α-(1-methylethyl) benzenemethanol methanesulfonate(ester) (interm. 1).

Example A2

A mixture of (±)-N-[4-[2-methyl-1-(1H-1,2,4-triazol-1-yl)propyl]phenyl]acetamide (0.095 mol) in HCl (3N) (250 ml) was stirred and heated at 60° C. for 5 hours. The mixture was cooled, poured into ice, basified with concentrated $NH_4OH$ and extracted with $CH_2Cl_2$. The organic layer was dried, filtered off and evaporated. The residue was crystallized from 2-propanone/$(C_2H_5)_2O$ and filtered off, yielding 15.5 g (75%) of (±)-4-[2-methyl-1-(1H-1,2,4-triazol-1-yl)propyl]-benzenamine (interm. 2; mp. 117.8° C.).

In a similar manner were also prepared:
(A)-4-[2-ethyl-1-(1H-1,2,4-triazol-1-yl)butyl]benzenamine (interm. 3);
(B)-4-[2-ethyl-1-(1H-1,2,4-triazol-1-yl)butyl]benzenamine (interm. 4); and
(±)-4-[2-ethyl-1-(1H-1,2,4-triazol-1-yl)butyl]benzenamine (interm. 5).

Example A3

1,2-Dichloroethanone (0.027 mol) was added dropwise at RT to a solution of intermediate (5) (0.0246 mol) in sodium carbonate (10%) (450 ml) and $CH_2Cl_2$ (600 ml). The mixture was stirred for 3 hours and then extracted with $CH_2Cl_2$. The organic layer was separated, dried, filtered and the solvent was evaporated, yielding 7 g (89%) of (±)-2-chloro-N-[4-[2-ethyl-1-(1H-1,2,4-triazol-1-yl)butyl]phenyl]acetamide (interm. 6).

Example A4 a) (±)-4-(2-methyl-3-phenylpropyl)pyridine (0.114 mol) was added portionwise at 0° C. to sulfonic acid (63 ml), the mixture was stirred at 0° C. for 1 hour and then at RT for 2 hours. The mixture was poured into ice, basified with $NH_4OH$ and the precipitate was filtered off, yielding 29.31 g (100%) of (±)-4-[2-methyl-1-(4-nitrophenyl)propyl]-pyridine (interm. 7).

b) Intermediate (7) (0.183 mol) in methanol (470 ml), $NH_4OH$ (47 ml) and a solution of thiophene in methanol (4%; 1 ml) was hydrogenated at RT with palladium on activated carbon (10%; 7.7 g) as a catalyst over a 2 hour period under a 3 bar pressure in a Parr apparatus. After uptake of hydrogen, the catalyst was filtered through celite and the filtrate was evaporated, yielding 42.79 g of product. A sample (3 g) was taken up in $CH_2Cl_2$ and purified on a glass filter over silica gel (eluent: $CH_2Cl_2/CH_3OH$ 99.5/0.5). The pure fractions were collected and evaporated. The residue was purified further by column chromatography over silica gel (eluent: $CH_2Cl_2/CH_3OH/NH_4OH$ 97.5/2.5/0.1). The pure fractions were collected and evaporated. The residue was recrystallized from $(C_2H_5)_2O$ and filtered off, yielding 0.86 g of (±)-4-[2-methyl-1-(3-pyridinyl)propyl]benzenamine (interm. 8; mp. 101.5° C.).

Example A5 a) A mixture of N-[4-(2-chloro-1-oxopropyl)phenyl]acetamide (0.19 mol), N-methylmethanamine hydrochloride (1:1)(0.38 mol) and $K_2CO_3$ (78.8 g) in $CH_3CN$ (1400 ml) was stirred and refluxed for 12 hours. The mixture was cooled, poured into water and extracted with $CH_2Cl_2$. The organic layer was dried, filtered and the solvent was evaporated, yielding 39.77 g (89%) of (±)-N-[4-[2-(dimethylamino)-1-oxopropyl]phenyl]-acetamide (interm. 9).

b) Sodium tetrahydroborate (2.6 mol) was added portionwise at 0° C. under $N_2$ flow to a mixture of intermediate (9) (2.18 mol) in methanol (5000 ml). The mixture was stirred for 1 hour, poured out into ice water (5000 ml) and extracted with $CH_2Cl_2$. The organic layer was separated, dried, filtered and the solvent was evaporated. The residue was stirred in DIPE, filtered off and dried, yielding 357 g (70%) of (±)-N-[4-[1-hydroxy-2-(dimethylamino)propyl]phenyl]acetamide (interm. 10).

Example A6

Sodium tetrahydroborate (0.0502 mol) was added portionwise at 0° C. to a mixture of (±)-N-[4-(2-chloro-1-oxopropyl)phenyl]-3,4-dimethoxybenzeneacetamide (0.0502 mol) in methanol (280 ml). The mixture was stirred at 0° C. for 1 hour, then poured out into a mixture of NaOH (280 ml) and ice, stirred for 1 hour and extracted with $CH_2Cl_2$. The organic layer was separated, dried, filtered and the solvent was evaporated, yielding 15.48 g (94%) of (±)-3,4-dimethoxy-N-[4-(3-methyl-2-oxiranyl)phenyl]benzeneacetamide (interm. 11).

Example A7 a) n-Butyl-lithium in hexane (1.6M; 71.6 ml) was added dropwise at −70° C. under $N_2$ flow to a mixture of 1-methylimidazole (0.1146 mol) in THF (195 ml). The mixture was stirred at −70° C. for 30 minutes. Chlorotrietylsilane (0.1146 mol) was added. The mixture was brought slowly to 10° C. and cooled again to −70° C. n-Butyl-lithium in hexane (1.6M; 71.6 ml) was added dropwise. The mixture was stirred at −70° C. for 1 hour, brought to −15° C. and cooled again to −70° C. A mixture of 4-chlorophenyl-4-nitrophenylmethanone (0.095 mol) in THF (150 ml) was added dropwise. The mixture was stirred at −70° C. for 30 minutes, hydrolized and extracted with EtOAc. The organic layer was separated, dried, filtered and the solvent was evaporated. The residue was purified by column chromatography over silica gel (eluent: $CH_2Cl_2/CH_3OH/NH_4OH$ 96/4/0.1). The desired fractions were collected and their solvents were evaporated, yielding 6.5 g (20%) of (±)-α-(4-chlorophenyl)-1-methyl-α-(4-nitrophenyl)-1H-imidazole-2-methanol (interm 12), 8.7 g (26.6%) of (±)-α-(4-chlorophenyl)-1-methyl-α-(4-nitrophenyl)-1H-imidazole-5-methanol (interm 13) and 18 g (53%) of the mixture of intermediate 12 and 13.

b) A mixture of intermediate 12 and 13 (0.09 mol) in THF (600 ml) was cooled on an ice bath. $TiCl_3$ in $H_2O$ (15%; 400 ml) was added dropwise quickly. The mixture was stirred at RT for 90 minutes, poured out on ice, alkalized with NaOH 10N, then filtered over celite, pasted up and extracted with $CH_2Cl_2$. The organic layer was separated, dried, filtered and the solvent was evaporated. The residue was purified by column chromatography over silica gel (eluent: $CH_2Cl_2/CH_3OH$ 94/6). Two pure fractions were collected and their solvents were evaporated. Both residues were crystallized from $CH_3CN$ and DIPE. Each phe precipitate was filtered off and dried, yielding 2 g (7.1%) of (±)-α-(4-aminophenyl)-α-(4-chlorophenyl)-1-methyl-1H-imidazole-2-methanol (interm. 14) and 1.5 g (5.3%) of (±)-α-(4-aminophenyl)-α-(4-chlorophenyl)-1-methyl-1H-imidazole-5-methanol (interm. 15).

B) PREPARATION OF THE COMPOUNDS OF FORMULA (I)

Example B1

A mixture of (±)-4-(acetylamino)-α-(1-methylethyl)benzenemethanol methane sulfonate (ester) (0.1541 mol), 1H-1,2,4-triazole (0.308 mol) and $K_2CO_3$ (0.308 mol) in $CH_3CN$ (500 ml) was stirred and refluxed for 12 hours. The solvent was evaporated and the residue was taken up in water/$CH_2Cl_2$. The organic layer was dried, filtered off and the solvent evaporated. The residue was purified by column chromatography over silica gel (eluent: $CH_2Cl_2/CH_3OH$ 97/3). The pure fractions were collected and evaporated, yielding 10 g (25%) of (±)-N-[4-[2-methyl-1-(1H-1,2,4-triazol-1-yl)propyl]-phenyl]acetamide (compound 153).

Example B2

A solution of 2-methyl-3-phenyl-2-propenoyl chloride (0.0554 mol) in $CH_2Cl_2$ (50 ml) was added dropwise to a solution of (±)-4-[2-methyl-1-(1H-1,2,4-triazol-1-yl)propyl]-benzenamine (0.037 mol) in pyridine (8 ml) and CH$_2$Cl$_2$ (100 ml) and the mixture was stirred at RT for 4 hours. The solvent was evaporated and the residue was taken up in water/EtOAc. The organic layer was dried, filtered and the solvent evaporated. The residue was purified by column chromatography over silica gel (eluent: CH$_2$Cl$_2$/CH$_3$OH/ NH$_4$OH 99/1/0.1). The pure fractions were collected and evaporated. The residue was crystallized from (C$_2$H$_5$)$_2$O/ methylethylketone, yielding 2.7 g (21%) of (±)-(E)-2-methyl-N-[4-[2-methyl-1-(1H-1,2,4-triazol-1-yl)propyl]phenyl]-3-phenyl-2-propenamide (compound 154).

Example B3

A mixture of 1-hydroxy-1H-benzotriazole (0.0227 mol) in THF (90 ml) was added dropwise at 5° C. under N$_2$ flow to a solution of (A)-4-[2-ethyl-1-(1H-1,2,4-triazol-1-yl)butyl] benzenamine (0.015 mol) and (±)-4-chloro-α-hydroxybenzeneacetic acid (0.0227 mol) in THF (95 ml). A mixture of N,N-methanetetraylbis[cyclohexanamine] (0.0227 mol) in CH$_2$Cl$_2$ (37 ml) was added dropwise at 5° C. under N$_2$ flow. The mixture was stirred at RT for 15 hours. The precipitate was filtered off and washed with CH$_2$Cl$_2$. The filtrate was taken up in K$_2$CO$_3$ 10% and extracted with CH$_2$Cl$_2$. The organic layer was separated, dried, filtered and the solvent was evaporated. The residue (9.25 g) was purified by column chromatography over silica gel (eluent: CH$_2$Cl$_2$/CH$_3$OH 96/4). The pure fractions were collected and the solvent was evaporated, yielding 4.8 g (78%) of (±)-(A)-4-chloro-N-[4-[2-ethyl-1-(1H-1,2,4-triazol-1-yl)butyl]-phenyl]-α-hydroxybenzeneacetamide (compound 16).

Example B4

(±)-(E)-N-[4-[1-(1H-imidazol-1-yl)-2-methylpropyl]phenyl]-2-methyl-3-phenyl-2-propenamide (0.0144 mol) in methanol (200 ml) was hydrogenated with palladium-on-charcoal 10% (0.52 g) as a catalyst at RT over a 5 hour period under a 1 bar pressure in a Parr apparatus. After uptake of hydrogen, the catalyst was filtered through celite and the solvent was evaporated. The residue was crystallized from 2-butanone/DIPE, yielding 4.9 g (94%) of (±)-N-[4-[1-(1H-imidazol-1-yl)-2-methylpropyl]phenyl]-α-methylbenzenepropanamide (compound 164).

Example B5

A mixture of 4-[1-(1H-imidazol-1-yl)-2-methylpropyl] benzenamine (0.0185 mol) in formic acid (20 ml) was stirred and heated at 120° C. for 15 minutes. The mixture was poured into water, basified with NaOH 3N and extracted with EtOAc. The organic layer was dried, filtered off and the solvent evaporated, yielding 3.9 g (86.6%) of (±)-N-[4-[1-(1H-imidazol-1-yl)-2-methylpropyl]phenyl]formamide (compound 177).

Example B6 a) A mixture of 4-[1-(1H-imidazol-1-yl)-2-methylpropyl] benzenamine (0.023 mol) and dihydro-2H-pyran-2,6(3H)-dione (0.03 mol) in THF (200 ml) was stirred and refluxed for 12 hours. When the reaction was complete, the solvent was evaporated, yielding 7.5 g (±)-5-[[4-[1-(1H-imidazol-1-yl)-2-methylpropyl]phenyl]amino]-5-oxopentanoic acid (compound 218).

b) A mixture of (compound 218) (0.023 mol) in ethanol (200 ml) and H$_2$SO$_4$ (3 ml) was stirred and refluxed for 12 hours. When the reaction was complete, the solvent was evaporated, the residue was taken up in water and extracted with CH$_2$Cl$_2$. The organic layer was dried, filtered and the solvent evaporated. The residue was purified by column chromatography over silica gel (eluent: CH$_2$Cl$_2$/CH$_3$OH/ NH$_4$OH 97/3/0.1). The pure fractions were collected and evaporated. The residue was crystallized from 2-butanone and DIPE, yielding 1.45 g (18%) of (±)-ethyl 5-[[4-[1-(1H-imidazol-1-yl)-2-methylpropyl]phenyl]amino]-5-oxopentanoate (compound 219).

Example B7

A mixture of (A)-N-[4-[1-(1H-imidazol-1-yl)-2-methylpropyl]phenyl]-4-nitrobenzeneacetamide (0.0005 mol) in methanol (50 ml) was hydrogenated at RT (p=2 bar) for 4 hours with Raney Nickel (0.2 g) as a catalyst. After uptake of hydrogen, the catalyst was filtered off over celite, washed with CH$_3$OH and the solvent was evaporated. The residue (0.12 g) was purified by column chromatography over silica gel (eluent: CH$_2$Cl$_2$/CH$_3$OH/NH$_4$OH 96.5/3.5/0.1). The pure fractions were collected and the solvent was evaporated. The residue was crystallized from diethyl ether. The precipitate was filtered off and dried, yielding 0.035 g (19%) of (A)-4-amino-N-[4-[1-(1H-imidazol-1-yl)-2-methylpropyl]phenyl]benzeneacetamide (compound 145).

Example B8

A solution of NaNO$_2$ (0.0023 mol) in water (6 ml) was added at 0° C./–5° C. to a solution of (B)$_4$-amino-N-[4-[1-[(1H-imidazol-1-yl)-2-methylpropyl]phenyl]-3-iodobenzeneacetamide (0.0021 mol) in HCl 2N (17 ml). The mixture was stirred at 0° C. for 15 minutes. A solution of NaN$_3$ (0.0023 mol) in water (6 ml) was added. The mixture was stirred at 0° C. for 2 hours, then neutralized with K$_2$CO$_3$ 10% and extracted with CH$_2$Cl$_2$. The organic layer was separated, dried, filtered and the solvent was evaporated. The residue was purified by column chromatography over silica gel (eluent: CH$_2$Cl$_2$/CH$_3$OH/NH$_4$OH 97/3/0.1). The pure fractions were collected and the solvent was evaporated. The residue was crystallized from 2-butanone and DIPE. The precipitate was filtered off and dried, yielding 0.46 g (44%) (B)-4-azido-N-[4-[1-(1H-imidazol-1-yl)-2-methylpropyl]phenyl]-3-iodobenzenacetamide (compound 259).

Example B9

A mixture of (±)-2-chloro-N-[4-[2-ethyl-1-(1H-1,2,4-triazol-1-yl)butyl]phenyl]acetamide (0.0218 mol), 1-methylpiperazine (0.0436 mol) and K$_2$CO$_3$ (0.0436 mol) in CH$_3$CN (150 ml) was stirred and refluxed for 4 hours. The mixture was cooled, poured out into water and extracted with CH$_2$Cl$_2$. The organic layer was separated, dried, filtered and the solvent was evaporated. The residue (8.13 g) was purified by column chromatography over silica gel (eluent: CH$_2$Cl$_2$/CH$_3$OH/NH$_4$OH 96/4/0.5). The pure fractions were collected and the solvent was evaporated. The residue was crystallized from diethyl ether. The precipitate was filtered off and dried, yielding 3 g (35.8%) (±)-N-[4-[2-ethyl-1-(1H-1,2,4-triazol-1-yl)butyl]phenyl]-4-methyl-1-piperazineacetamide (compound 15).

Example B10

Compound (16) (0.0116 mol) was separated into its enantiomers by column chromatography (eluent: hexane/2- propanol 50/50; column: CHIRACEL OD 20 μm). Two pure fractions were collected and their solvents were evaporated. The residue was crystallized from diethyl ether. The precipitate was filtered off and dried, yielding 1.77 g (35%) (±)-A1-4-chloro-N-[4-[2-ethyl-1-(1H-1,2,4-triazol-1-yl)butyl]phenyl]-α-hydroxybenzeneacetamide (compound 17) and 1.72 g (42%) (±)-(A2)-4-chloro-N-[4-[2-ethyl-1-(1H-1,2,4-triazol-1-yl)butyl]phenyl]-α-hydroxybenzeneacetamide (compound 18).

Example B11

HCl conc. (3.6 ml) was added at RT to a mixture of (±)-1,1-dimethylethyl 4-[[[4-[2-ethyl-1-(1H-imidazol-1-yl)butyl]phenyl]amino]carbonyl]-1-piperidinecarboxylate (0.0032 mol) in EtOAc (30 ml). The mixture was stirred at RT for 4 hours, then basified with a concentrated NaOH solution and extracted with EtOAc and then $CH_2Cl_2$. The organic layer was separated, dried, filtered and the solvent was evaporated. The residue (1 g) was converted into the hydrochloric acid salt (1:1) in 2-propanol. The precipitate was filtered off and dried, yielding 0.85 g (68%) (±)-N-[4-[2-ethyl-1-(1H-imidazol-1-yl)butyl]-phenyl]4-piperidinecarboxamide monohydrochloride (compound 57).

Example B12

A mixture of α-(4-chlorophenyl)-3-pyridinemethanol (0.364 mol) and N-phenyl acetamide (0.364 mol) in HOAc (360 ml) and $H_2SO_4$ 36N (38.6 ml) was stirred and refluxed for 6 days. The solvent was evaporated, yielding 122.6 g (±)-N-[4-[(4-chlorophenyl)(3-pyridinyl)methyl]phenyl]acetamide (compound 673).

Example B13

Butyllithium, 1.6M in hexane (146 ml) was added dropwise at −78° C. under $N_2$ flow to a solution of 2-bromopyridine (0.1348 mol) in THF (300 ml). The mixture was stirred at −78° C. for 20 minutes. A solution of N-(4-formylphenyl)acetamide (0.1226 mol) in THF (300 ml) was added at −60° C./−70° C. The mixture was stirred at −60° C./−70° C. for 1 hour, then poured out into ice water and extracted with EtOAc. The organic layer was separated, dried, filtered and the solvent was evaporated. The residue (27 g) was purified by column chromatography over silica gel (eluent: $CH_2Cl_2/CH_3OH/NH_4OH$ 96/4/0.1). The pure fractions were collected and the solvent was evaporated. The residue was crystallized from diethyl ether and 2-propanone. The precipitate was filtered off and dried, yielding 5.09 g (17%) (±)-N-[4-[hydroxy(2-pyridinyl)methyl]phenyl]-acetamide (compound 688).

Example B14

To a solution of 4-[2-methyl-1-(3-pyridinyl)propyl]benzenamine (0.187 mol) into $CH_2Cl_2$ (400 ml) was added dropwise $Al_2O$ (100 ml). The mixture was stirred for 24 hours at RT. The mixture was hydrolyzed by $H_2O$ and neutralized by $NH_4OH$. The organic layer was washed with water and dried. The filtrate was evaporated, yielding 50 g of N-[4-[2-methyl-1-(3-pyridinyl)propyl]phenyl]acetamide (compound 671).

Example B15

1H-1,2,4-triazole (0.19 mol) and triphenylphosphine (0.19 mol) were added to a mixture of (±)-N-[4-[1-hydroxy-2-(dimethylamino)propyl]phenyl]acetamide (0.1269 mol) in THF (300 ml). The mixture was cooled to 0° C. Diethyl 1,2-hydrazinedicarboxylate (0.19 mol) was added dropwise. The mixture was stirred at RT overnight. The solvent was evaporated and the residue was taken up in EtOAc and HCl 1N was added. The mixture was separated into its layers. The aqueous layer was washed with EtOAc, basified with a $K_2CO_3$ solution and extracted with $CH_2Cl_2$. The organic layer was separated, dried, filtered and the solvent was evaporated. The residue was purified by column chromatography over silica gel (eluent: $CH_2Cl_2/CH_3OH/NH_4OH$ 93/7/0.1 and 80/20/0.1). Two pure fractions were collected and their solvents were evaporated. The desired fraction was recrystallized from 2-propanone/EtOAc. The precipitate was filtered off and dried, yielding 1.2 g of (±)-(B)-N-[4-[2-(dimethylamino)-1-(1H-1,2,4-triazol-1-yl)propyl]phenyl]acetamide (compound 631).

Example B16

A mixture of (±)-(E)-N-[4-[1-(1H-imidazol-1-yl)-2-methylpropyl]phenyl]-2-[(4-nitrophenyl)-methylene]propanamide (0.00742 mol) in THF (80 ml) and $TiCl_3$ (30 ml) was stirred at 0° C. for 15 minutes. The mixture was poured into water, ice and NaOH 3N and extracted with $CH_2Cl_2$ (2×100 ml). The combined organic layers were dried, filtered and the solvent evaporated. The residue was taken up in $CH_2Cl_2$ and $(C_2H_5)_2O$. The precipitate was filtered off and stirred $K_2CO_3$ 10% and $CH_2Cl_2$, dried, filtered off and evaporated. The residue was crystallized from 2-propanone. The precipitate was filtered off, taken up in $Na_2CO_3$ 10% and $CH_2Cl_2$. The organic layer was dried, filtered off and evaproated. The residue was purified by column chromatography over silica gel (eluent: $CH_2Cl_2/CH_3OH/NH_4OH$ 96/4/0.1). The pure fractions were collected and evaporated. The residue was crystallized from $(C_2H_5)_2O$, yielding 1.5 g (±)-(E)-2-[(4-aminophenyl)methylene]-N-[4-[1-(1H-imidazol-1-yl)-2-methylpropyl]phenyl]propanamide (compound 611).

Example B17

1,1'-Carbonyldiimidazole (0.236 mol) was added at 60° C. to a solution of (±)-N-[4-[1-hydroxy-2-methylpropyl]phenyl]acetamide (0.115 mol) in tetrahydrofuran (240 ml) and the mixture was stirred at 60° C. for 12 hours. The solvent was evaporated and the residue was taken up in water/$CH_2Cl_2$. The organic layer was dried, filtered and the solvent evaporated. The residue was purified by column chromatography over silica gel (eluent: $CH_2Cl_2/CH_3OH$ 95/5). The pure fractions were collected and evaporated. The residue was crystallized from 2-propanone, yielding 28.27 g (67%) (±)-N-[4-[1-(1H-imidazol-1-yl)-2-methylpropyl]phenyl]acetamide (compound 521).

Example B18

$LiAlH_4$ (0.0117 mol) was added portionwise at 0° C. to a solution of (±)-ethyl (A)-β-[4-[[(3,4-dimethoxyphenyl)acetyl]amino]phenyl]-α-methyl-1H-imidazol-1-propanoate (0.0117 mol) in THF (78 ml). The mixture was allowed to warm to RT overnight and then cooled to 0° C. $LiAlH_4$ (0.0117 mol) was added portionwise at 0° C. The mixture was allowed to warm to RT, then stirred at RT for 2 hours, poured out on ice and filtered over celite. The filtrate was extracted with EtOAc. The organic layer was separated, dried, filtered and the solvent was evaporated. The residue was purified by column chromatography over silica gel (eluent: $CH_2Cl_2/CH_3OH/NH_4OH$ 95/5/0.1 and 90/10/0.2). Two pure fractions (F1 and F2) were collected and their solvents were evaporated. F1 was crystallized from 2-propanone. The precipitate was filtered off and dried, yielding 0.9 g (±)-(A)-3,4-dimethoxy-N-[4-[1-(1H-imidazol-1-yl)-2-(hydroxymethyl)propyl]phenyl]benzeneacetamide (19%) (compound 386). F2 was purified by column chromatography over silica gel (eluent: $CH_2Cl_2/CH_3OH/NH_4OH$ 95/5/0.2). The pure fractions were collected and the solvent was evaporated. The residue was purified by column chromatography over amino phase (eluent: $CH_2Cl_2/CH_3OH$ 95/5). The pure fractions were collected and the solvent was evaporated, yielding 0.5 g (±)-(B)-3,4-dimethoxy-N-[4-[1-(1H-imidazol-1-yl)-2-(hydroxymethyl)propyl]phenyl]-benzeneacetamide (10%) (compound 394).

Example B19

A mixture of (±)-3,4-dimethoxy-N-[4-[1-(1H-imidazol-1-yl)-2-[methyl(phenylmethyl)amino]propyl]phenyl]benzeneacetamide (0.0066 mol) in ethanol (150 ml) was hydrogenated (p=3 bar) for 90 minutes with palladium-on-charcoal 10% (3.3 g) as a catalyst. After uptake of hydrogen, the catalyst was filtered off over celite, washed with $CH_3OH$ and the solvent was evaporated. The residue (2.72 g) was purified by column chromatography over silica gel (eluent: $CH_2Cl_2/CH_3OH/NH_4OH$ 92/8/1). Two pure fractions were collected and their solvents were evaporated. Each residue was crystallized from 2-butanone and diethyl ether. The precipitate was filtered off and dried, yielding 0.39 g (14.5%) of (±)-(A)-3,4-dimethoxy-N-[4-[1-(1H-imidazol-1-yl)-2-(methylamino)propyl]phenyl]benzeneacetamide (compound 400).

Example B20

A mixture of (±)-3,4-dimethoxy-N-[4-(3-methyl-2-oxiranyl)phenyl]benzeneacetamide (0.0442 mol) and 1H-imidazole (0.221 mol) in DMF (116 ml) was stirred and refluxed for 6 hours. The mixture was poured out into water and extracted with EtOAc. The organic layer was separated, dried, filtered and the solvent was evaporated. The residue was purified by column chromatography over silica gel (eluent: $CH_2Cl_2/CH_3OH/NH_4OH$ 96/4/0.3). The desired fraction was taken up in $CH_2Cl_2$, washed with a saturated NaCl solution, dried, filtered and the solvent was evaporated. The residue was purified by column chromatography over silica gel (eluent: $CH_2Cl_2/CH_3OH/NH_4OH$ 93/7/1). The pure fractions were collected and the solvent was evaporated. The residue was crystallized from 2-propanone. The precipitate was filtered off and dried, yielding 1.53 g (9%) of (±)-(B)-3,4-dimethoxy-N-[4-[2-hydroxy-1-(1H-imidazol-1-yl)propyl]phenyl]benzeneacetamide monohydrate (compound 402).

Example B21

A mixture of (±)-(A)-3-[4-[[(3,4-dimethoxyphenyl)acetyl]amino]phenyl]-3-(1H-imidazol-1-yl)-2-methylpropyl methanesulfonate (0.0011 mol) in $NaOCH_3$ (1 ml) and methanol (5 ml) was stirred at 80° C. for 3 hours. The mixture was poured out on ice and extracted with $CH_2Cl_2$. The organic layer was separated, dried, filtered and the solvent was evaporated. The residue (0.56 g) was purified by column chromatography over silica gel (eluent: $CH_2Cl_2/CH_3OH/NH_4OH$ 97.5/2.5/0.1). The pure fractions were collected and the solvent was evaporated. The residue was crystallized from diethyl ether. The precipitate was filtered off and dried, yielding 0.2 g (43%) of (±)-(A)-3,4-dimethoxy-N-[4-[1-(1H-imidazol-1-yl)-3-methoxy-2-methylpropyl]phenyl]benzeneacetamide (compound 404).

Example B22 a) A mixture of compound (698) (0.0329 mol) in NaOH 3N (300 ml) was stirred and refluxed for 2 hours. The mixture was cooled, poured into ice, neutralized with concentrated HCl and extracted with $CH_2Cl_2$. The organic layer was dried, filtered and the solvent evaporated, yielding 7.91 g (88%) of (±)-4-[1-(1H-imidazol-1-yl)-2-methylpropyl]phenylthiourea (compound 699).

b) An alternative reaction procedure is the following: A solution of trifluoroacetic acid (0.0715 mol) in benzene (5 ml) was added dropwise to a solution of 4-[1-(1H-imidazol-1-yl)-2-methylpropyl]benzenamine (0.0511 mol) and NaSCN (0.102 mol) in benzene (70 ml), the mixture was stirred at RT for 1 hour and stirred further at 60° C. for 24 hours. The mixture was cooled to 30° C., and extracted with $CH_2Cl_2$ and $K_2CO_3$ 10%. The organic layer was washed with water, dried, filtered and the solvent evaporated. The residue was purified by column chromatography over silica gel (eluent: $CH_2Cl_2/CH_3OH/NH_4OH$ 95/5/0.5 to 90/10/0.5) (35–70 µm) and purified further by column chromatography over silica gel (eluent: $CH_2Cl_2/CH_3OH/NH_4OH$ 92/8/0.5) (15–40 µm). The pure fractions were collected and evaporated. The residue was recrystallized from 2-propanone and $(C_2H_5)_2O$ and filtered off. The product was taken up in $CH_2Cl_2$, $CH_3OH$ and norit. The product was recrystallized from 2-propanone and $(C_2H_5)_2O$ and filtered off, yielding 1.42 g (±)-4-[1-(1H-imidazol-1-yl)-2-methylpropyl]-phenylthiourea (10%) (compound 699).

Example B23

A mixture of compound (206) (0.0104 mol), 2-pyridinamine (0.0104 mol) and N,N-dimethyl-4-pyridinamine (0.0052 mol) in 1,4-dioxane (100 ml) was stirred and refluxed overnight. The solvent was evaporated. The residue was dissolved in $CH_2Cl_2$. The organic solution was washed with a 10% aqueous $K_2CO_3$ solution, with water, dried, filtered and the solvent was evaporated. The residue was purified by column chromatography over silica gel (eluent: $CH_2Cl_2/CH_3OH/NH_4OH$ 97/3/0.1). The pure fractions were collected and the solvent was evaporated. The residue was crystallized from 2-propanone and DIPE. The precipitate was filtered off and dried, yielding 1.10 g (34.3%) (±)-N-(2-pyridinyl)-N'-[4-[1-(1H-imidazol-1-yl)-2-methylpropyl]phenyl]urea (compound 274).

Example B24 n-Butyllithium 1.6M in hexane (101.5 ml) was added dropwise at −70° C. under $N_2$ flow to a mixture of 1-methyl-1H-imidazole (0.162 mol) in THF (244 ml). The mixture was stirred at −70° C. for 30 minutes. Chlorotriethylsilane (0.162 mol) was added. The mixture was allowed to warm to RT. n-Butyllithium 1.6M in hexane (101.5 ml) was added dropwise at −70° C. The mixture was stirred at −70° C. for 1 hour and brought to −15° C. A mixture of intermediate (9)

(0.065 mol) in THF (152 ml) was added dropwise at −70° C. The mixture was allowed to warm to RT, stirred overnight, then poured out into a saturated $NH_4Cl$ solution and extracted with EtOAc. The organic layer was separated, dried, filtered and the solvent was evaporated. The residue was purified by column chromatography over silica gel (eluent: $CH_2Cl_2/CH_3OH/NH_4OH$ 96/4/0.5 and 80/20/2). The pure fractions were collected and the solvent was evaporated. The residue was crystallized from 2-propanone. The precipitate was filtered off and dried, yielding 1.5 g (±)-N-[4-[2-(dimethylamino)-1-hydroxy-1-(3-methyl-3H-imidazol-4-yl)propyl]phenyl]acetamide (compound 771).

Example B25

Benzoylchloride (0.067 mol) was added to a solution of $NH_4SCN$ (5.09 g) in 2-propanone (150 ml) and the mixture was stirred and refluxed for 20 minutes. A solution of 4-[1-(1H-imidazol-1-yl)-2-methylpropyl]benzenamine (0.0557 mol) in 2-propanone (150 ml) was added and the mixture was stirred and refluxed at 80° C. overnight. The mixture was cooled, filtered through celite and the filtrate was evaporated. The residue was taken up in $CH_2Cl_2$. The organic layer was dried, filtered and the solvent evaporated. The residue was purified by column chromatography over silica gel (eluent: $CH_2Cl_2/CH_3OH/NH_4OH$ 98/2/0.1). The pure fractions were collected and evaporated. The residue was recrystallized from 2-propanone and DIPE, yielding (±)-N-benzoyl-N'-[4-[1-(1H-imidazol-1-yl)-2-methylpropyl]phenyl]thiourea (compound 698).

Example B26

A mixture of compound (689) (0.0309 mol) and iodomethane (0.062 mol) in acetonitrile (100 ml) was stirred at 50° C. for 2 hours. The solvent was evaporated, yielding 10.9 g (91%) (±)-N-[4-[1-hydroxy-1-(3-pyridinium)methyl]phenyl]acetamide iodide (compound 770).

Example B27

A mixture of 1-[2-ethyl-1-(4-isothiocyanatophenyl)butyl]-1H-imidazole (0.0123 mol) and 2-benzothiazolamine (0.0148 mol) in acetonitrile (80 ml) was stirred and refluxed for 12 hours. The solvent was evaporated and the residue was taken up in $H_2O$ and $CH_2Cl_2$. The organic layer was separated, dried, filtered and the solvent was evaporated. The residue was purified by column chromatography over silica gel (eluent: $CH_2Cl_2/CH_3OH/NH_4OH$ 97.5/2.5/0.1). The desired fractions were collected and the solvent was evaporated. The residue was purified again by column chromatography over silica gel (eluent: $CH_2Cl_2/CH_3OH/NH_4OH$ 85/15/0.1). The pure fractions were collected and the solvent was evaporated. The residue was crystallized from 2-butanone and DIPE. The precipitate was filtered off and dried, yielding 0.44 g (9%) (±)-N-(2-benzothiazolyl)-N'-[4-[1-(1H-imidazol-1-yl)-2-ethylbutyl]phenyl]-thiourea (compound 705).

Example B28

A mixture of compound (651) (0.0136 mol) and phosphorous pentasulfide (0.0136 mol) in pyridine (200 ml) was stirred and heated at 120° C. for 12 hours. The solvent was evaporated, the residue was taken up in water, $NH_4OH$, $CH_2Cl_2$ and $CH_3OH$ (10%), and the mixture was stirred at RT for 15 minutes. The organic layer was decanted off, dried, filtered and evaporated. The residue was purified by column chromatography over silica gel (eluent: $CH_2Cl_2/CH_3OH/NH_4OH$ 97/3/0.1). The desired fractions were collected and evaporated. The residue was recrystallized from 2-propanone and DIPE, filtered off and dried, yielding (22%) 1.15 g 4-chloro-N-[4-[1-(1H-imidazol-1-yl)-2-methylpropyl]phenyl]benzenethane-thioamide (compound 764).

Example B29

A solution of methyl N'-(3-fluorophenyl)-N-[4-[1-(1H-imidazol-1-yl)-2-methylpropyl]-phenyl]carbamimidothioate (0.0094 mol) in $NH_3/CH_3OH$ (60 ml) was stirred and heated in autoclave at 40° C. for 3 days. The solvent was evaporated and the residue was purified by column chromatography over silica gel (eluent: $CH_2Cl_2/CH_3OH/NH_4OH$ 94/6/0.2 to 90.10/0.5). The pure fractions were collected and evaporated. The residue was crystallized from 2-propanone and $(C_2H_5)_2O$ and filtered off, yielding 0.89 g (46%) N'-(3-fluorophenyl)-N-[4-[1-(1H-imidazol-1-yl)-2-methylpropyl]phenyl]guanidine (compound 744).

Example B30

A solution of KOCN (2.25 g) in water was added dropwise at RT to a mixture of 4-[1-(1H-imidazol-1-yl)-2-methylpropyl]benzenamine (0.0278 mol) in acetic acid (4 ml) and water (50 ml) and the mixture was stirred at RT for 1 hour. The mixture was neutralized with NaOH 3N and extracted with $CH_2Cl_2$ and $CH_3OH$. The organic layer was washed with water, dried, filtered and the solvent evaporated. The residue was purified by column chromatography over silica gel (eluent: $CH_2Cl_2/CH_3OH/NH_4OH$ 96/4/0.3). The pure fractions were collected and evaporated. The residue was recrystallized from 2-propanone, yielding 2.7 g (51.4%) (±)-4-[1-(1H-imidazol-1-yl)-2-methylpropyl]phenylurea (compound 266).

Example B31

4-Fluorophenylisocyanate (0.017 mol) was added to a solution of 4-[1-(1H-imidazol-1-yl)-2-methylpropyl]benzenamine (0.014 mol) in dry THF (100 ml) and the mixture was stirred and refluxed for 2 hours. The mixture was cooled, the precipitate was filtered off and recrystallized from 2-propanone and $CH_3OH$, yielding 1.6 g (32%) (±)-N-(4-fluorophenyl)-N'-[4-[1-(1H-imidazol-1-yl)-2-methylpropyl]phenyl]urea (compound 740).

Example B32

$CH_3I$ (0.00814 mol) was added at RT to a mixture of compound 792 (0.00814 mol) in 2-propanone (30 ml). The mixture was stirred at RT for 6 hours, poured out into $H_2O$ and a concentrated $NH_4OH$ solution and extracted with $CH_2Cl_2$. The organic layer was separated, dried, filtered and the solvent was evaporated, yielding 3.18 g of methyl [4-[(2,5-dichlorophenyl)(1H-imidazol-1-yl)methyl]phenyl]carbamimidothioate (comp. 796).

Example B33

Formamide (130 ml) was added to a mixture of intermediate 15 (0.043 mol) in acetic acid (130 ml). The mixture was stirred at 150° C. for 2 hours, cooled, poured out into ice water and basified with a concentrated $NH_4OH$ solution. The precipitate was filtered off, washed with $H_2O$ and taken up in CH$_2$Cl$_2$ and a small amount of CH$_3$OH. The organic solution was dried, filtered and the solvent was evaporated. This fraction was crystallized from CH$_2$Cl$_2$, CH$_3$OH and DIPE. The precipitate was filtered off and dried, yielding 2.2 g (15.1%) of (±)-N-[4-[(4-chlorophenyl)(1-methyl-1H-imidazol-5-yl)methyl]-phenyl]formamide (comp. 793).

Example B34

Compound (779) (0.0132 mol) was separated into its enantiomers by column chromatography over silica gel (eluent: hexane/C$_2$H$_5$OH 80/20; column: CHIRACEL OD 20 μm). Two pure fractions were collected and their solvents were evaporated. The residue was dissolved in 2-propanone and 2-propanol and converted into the oxalic acid salt (1:1). The precipitate was filtered off and dried, yielding 2.55 g of (A)-N-[4-[2-ethyl-1-(1H-imidazol-1-yl)butyl]phenyl]-3-hydroxybenzeneacetamide ethanedioate (1:1) (comp. 780) and 2.95 g of (B)-N-[4-[2-ethyl-1-(1H-imidazol-1-yl)butyl]phenyl]-3-hydroxy-benzeneacetamide ethanedioate (1:1) (comp. 781).

Tables 1 to 20 list the compounds of formula (I) which were prepared analogous to one of the above examples.

TABLE 1

| Co. No. (Ex No) | X; R$^4$; stereochemistry descriptor if not racemic and/or addition salt |
|---|---|
| 1 (B1) | N; CH$_3$ |
| 2 (B2) | N; C(CH$_3$)=CHC$_6$H$_5$; (E) |
| 3 (B2) | N; C$_6$H$_5$ |
| 4 (B3) | N; CH(OH)(4-Cl—C$_6$H$_4$) |
| 5 (B2) | N; (1,3-benzodioxolan-5-yl)methyl |
| 6 (B2) | N; (3,4-diOCH$_3$)C$_6$H$_3$ |
| 7 (B2) | N; (2,3-dihydro-1,4-benzodioxin-6-yl)methyl |
| 8 (B3) | N; (CH$_2$)$_3$(3,4-diOCH$_3$—C$_6$H$_3$) |
| 9 (B2) | N; OC$_6$H$_5$ |
| 10 (B3) | N; (CH$_2$)$_2$(3,4-diOCH$_3$—C$_6$H$_3$) |
| 11 (B3) | N; CH(OH)(3,4-diCH$_3$—C$_6$H$_3$) |
| 12 (B2) | N; CH$_2$O(2-OCH$_3$—C$_6$H$_4$) |
| 13 (B3) | N; (2-NH$_2$-benzothiazol-6-yl)-CH$_2$ |
| 14 (B2) | N; CH$_2$Cl |
| 15 (B9) | N; (4-CH$_3$-1-piperazinyl)-CH$_2$ |
| 16 (B3) | N; CH(OH)(4-Cl—C$_6$H$_4$); (A) |
| 17 (B10) | N; CH(OH)(4-Cl—C$_6$H$_4$); (A, A) |
| 18 (B10) | N; CH(OH)(4-Cl—C$_6$H$_4$); (A, B) |
| 19 (B3) | N; CH(OH)(4-Cl—C$_6$H$_4$); (B) |
| 20 (B10) | N; CH(OH)(4-Cl—C$_6$H$_4$); (B, A) |
| 21 (B10) | N; CH(OH)(4-Cl—C$_6$H$_4$); (B, B) |
| 22 (B2) | CH; phenyl |
| 23 (B2) | CH; 2,3-dihydro-1,4-benzodioxin-2-yl |
| 24 (B3) | CH; C(OH)(CH$_3$)$_2$ |
| 25 (B2) | CH; 1,4-benzodioxin-2-yl |
| 26 (B2) | CH; (2,3-dihydro-1,4-benzodioxin-2-yl)-CH$_2$ |
| 27 (B2) | CH; 2-pyrazinyl |
| 28 (B2) | CH; (1,3-benzodioxolan-5-yl)-CH$_2$ |
| 29 (B2) | CH; 3,4-dihydro-2H-1-benzopyran-2-yl |
| 30 (B2) | CH; 5,5,8,8-tetramethyl-5,6,7,8-tetrahydro-2-naphthalenyl |
| 31 (B2) | CH; 2H-1-benzopyran-3-yl |
| 32 (B2) | CH; (CH$_2$)$_2$(3,4-diOCH$_3$—C$_6$H$_4$) |

TABLE 1-continued

| Co. No. (Ex No) | X; R$^4$; stereochemistry descriptor if not racemic and/or addition salt |
|---|---|
| 33 (B2) | CH; 3,4-dihydro-2H-1-benzopyran-3-yl |
| 34 (B2) | CH; 1,3-benzodioxolan-2-yl |
| 35 (B2) | CH; 4-OC$_2$H$_5$—C$_6$H$_4$ |
| 36 (B2) | CH; (2,3-dihydro-1,4-benzodioxin-6-yl)-CH$_2$ |
| 37 (B2) | CH; CH$_2$O(2-OCH$_3$—C$_6$H$_4$) |
| 38 (B2) | CH; (5,5,8,8-tetramethyl-5,6,7,8-tetrahydro-2-naphthalenyl)-CH$_2$ |
| 39 (B2) | CH; (CH$_2$)$_2$(4-OC$_2$H$_5$—C$_6$H$_4$) |
| 40 (B5) | CH; H |
| 41 (B2) | CH; CH$_2$-(4-C$_6$H$_5$—C$_6$H$_4$) |
| 42 (B2) | CH; CH$_2$Cl |
| 43 (B9) | CH; (1-piperidinyl)methyl |
| 44 (B9) | CH; (4-CH$_3$-1-piperazinyl)-CH$_2$ |
| 45 (B3) | CH; 2-methoxy-5-pyridinyl |
| 46 (B3) | CH; 1-(C$_6$H$_5$—CO)-4-piperidinyl |
| 47 (B9) | CH; (4-morpholinyl)-CH$_2$ |
| 48 (B3) | CH; (CH$_2$)$_3$(4-OC$_2$H$_5$—C$_6$H$_4$) |
| 49 (B3) | CH; CH$_2$O(2-OH—C$_6$H$_4$) |
| 50 (B2) | CH; CH(SCH$_3$)(C$_6$H$_5$) |
| 51 (B3) | CH; (2-OCH$_3$-5-pyridinyl)-CH$_2$ |
| 52 (B3) | CH; (CH$_2$)$_3$(3,4-diOCH$_3$—C$_6$H$_3$) |
| 53 (B3) | CH; 1-(tert-butoxy-carbonyl)-4-piperidinyl |
| 54 (B3) | CH; CH(OH)(4-Cl—C$_6$H$_4$) |
| 55 (B3) | CH; CH$_2$N(CH$_3$)$_2$ |
| 56 (B3) | CH; CH(OH)(3,4-diOCH$_3$—C$_6$H$_3$) |
| 57 (B11) | CH; 4-piperidinyl |
| 58 (B3) | CH; (2-NH$_2$-6-benzothiazolyl)-CH$_2$ |
| 59 (B3) | CH; 1-methyl-4-piperidinyl |
| 60 (B2) | CH; OC$_6$H$_5$ |
| 61 (B10) | CH; (CH$_2$)$_2$(4-OC$_2$H$_5$—C$_6$H$_4$); (A) |
| 62 (B10) | CH; (CH$_2$)$_2$(4-OC$_2$H$_5$—C$_6$H$_4$); (B) |
| 63 (B23) | N; 2-benzothiazolyl-NH— |
| 64 (B23) | CH; 2-benzothiazolyl-NH— |
| 777 (B3) | N; 2-benzothiazolyl |
| 778 (B3) | CH; 2-benzothiazolyl; oxalic acid (1:1) |

TABLE 2

| Co. No. | Ex. No. | X | (R$^b$)$_n$; stereochemical descriptor if not racemic and/or addition salt |
|---|---|---|---|
| 65 | B2 | N | 4-CH$_3$ |
| 66 | B2 | N | 4-Cl |
| 67 | B3 | N | 3-OH |
| 68 | B2 | N | 4-F |
| 69 | B3 | N | 4-OH |
| 70 | B2 | N | 3-OCH$_3$ |
| 71 | B2 | N | 4-OC$_2$H$_5$ |
| 72 | B3 | N | 3-OCH$_3$; 4-OH |
| 73 | B2 | N | 3-OCH$_3$; 4-OCH$_3$ |

TABLE 2-continued

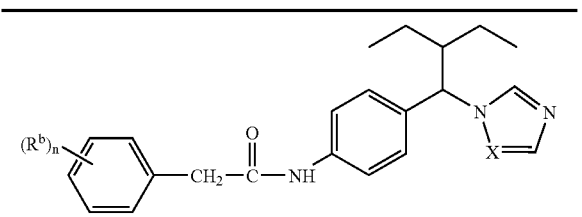

| Co. No. | Ex. No. | X | (R^b)_n; stereochemical descriptor if not racemic and/or addition salt |
|---|---|---|---|
| 74 | B2 | N | 3-Cl; 4-OCH₃ |
| 75 | B2 | N | 3-Cl; 4-OC₂H₅ |
| 76 | B2 | N | 3-CH₃; 4-OC₂H₅ |
| 77 | B2 | N | 3-CH₃; 4-CH₃ |
| 78 | B3 | N | 3-CH₃; 4-OCH₃ |
| 79 | B3 | N | 3-Cl; 4-OH |
| 80 | B2 | N | 3-OCH₃; 4-OCH₃; 5-OCH₃ |
| 81 | B2 | N | 3-CH₃; 4-CH₃; 5-CH₃ |
| 82 | B3 | N | 3-OC₂H₅; 4-OC₂H₅ |
| 83 | B3 | N | 3-OCH₃; 4-Cl |
| 84 | B3 | N | 3-OCH₃; 4-CH₃ |
| 85 | B10 | N | 3-CH₃; 4-OCH₃; (A) |
| 86 | B10 | N | 3-CH₃; 4-OCH₃; (B) |
| 87 | B2 | CH | 4-Cl |
| 88 | B2 | CH | 4-F |
| 89 | B2 | CH | 2-OCH₃ |
| 90 | B2 | CH | 3-OCH₃ |
| 91 | B2 | CH | 3-OCH₃; 4-OCH₃ |
| 92 | B2 | CH | 4-OCH(CH₃)₂ |
| 93 | B2 | CH | 4-O(CH₂)₂CH₃ |
| 94 | B2 | CH | 4-CH₃ |
| 95 | B2 | CH | 4-OC₂H₅ |
| 96 | B2 | CH | 4-O(CH₂)₃CH₃ |
| 97 | B3 | CH | 3-OCH₃; 4-OH; oxalic acid (1:1) |
| 98 | B2 | CH | 2-OCH₃; 5-OCH₃ |
| 99 | B3 | CH | 4-N(CH₃)₂ |
| 100 | B2 | CH | 3-CH₃ |
| 101 | B2 | CH | 3-OC₂H₅; 4-OC₂H₅ |
| 102 | B2 | CH | 2-OCH₃; 3-OCH₃ |
| 103 | B2 | CH | 4-OC₆H₅ |
| 104 | B2 | CH | 2-CH₃ |
| 105 | B2 | CH | 4-OCH₃ |
| 106 | B2 | CH | 2-CH₃; 5-CH₃ |
| 107 | B3 | CH | 2-OH |
| 108 | B3 | CH | 3-OH; 4-OCH₃ |
| 109 | B3 | CH | 3-OH; oxalic acid (1:1) |
| 110 | B2 | CH | 3-OCH₃; 4-CH₃ |
| 111 | B3 | CH | 4-OH |
| 112 | B3 | CH | 3-CH₃; 4-CH₃ |
| 113 | B2 | CH | 2-OCH₃; 4-Cl |
| 114 | B2 | CH | 2-OCH₃; 6-OCH₃ |
| 115 | B2 | CH | 2-OCH₂C₆H₅; 3-OCH₃ |
| 116 | B2 | CH | 3-Cl; 4-OCH₃ |
| 117 | B3 | CH | 3-Cl; 4-OH |
| 118 | B2 | CH | 3-Cl; 4-OC₂H₅ |
| 119 | B2 | CH | 3-OCH₃; 5-OCH₃ |
| 120 | B2 | CH | 2-OCH₂C₆H₅; 5-OCH₃ |
| 121 | B3 | CH | 4-(2-pyridinylmethoxy) |
| 122 | B2 | CH | 2-OCH₃; 5-CH₃ |
| 123 | B2 | CH | 3-CH₃; 4-OCH₃ |
| 124 | B3 | CH | 2-OH; 5-CH₃ |
| 125 | B2 | CH | 3-CH₃; 4-OC₂H₅ |
| 126 | B3 | CH | 2-OCH₃; 4-OCH₃ |
| 127 | B3 | CH | 4-(4-pyridinylmethoxy) |
| 128 | B3 | CH | 3-OC₂H₅; 4-OCH₂C₆H₅ |
| 129 | B3 | CH | 2-CH₃; 4-OH |
| 130 | B3 | CH | 4-(3-pyridinylmethoxy) |
| 779 | B3 | CH | 3-OH |
| 780 | B34 | CH | 3-OH; (A); oxalic acid (1:1) |
| 781 | B34 | CH | 3-OH; (B); oxalic acid (1:1) |
| 782 | B34 | N | 3-OCH₃; 4-CH₃; (A) |
| 783 | B34 | N | 3-OCH₃; 4-CH₃; (B) |

TABLE 3

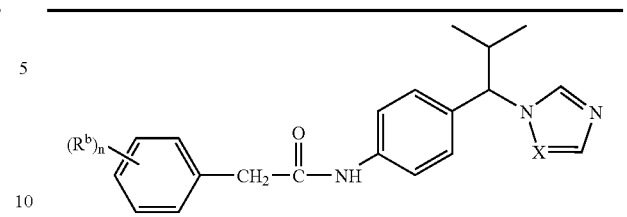

| Co. No. | Ex. No. | X | (R^b)_n; stereochemical descriptor of not racemic and/or addition salt |
|---|---|---|---|
| 131 | B2 | N | 4-Cl |
| 132 | B2 | N | 4-F |
| 133 | B2 | N | 4-CH₃ |
| 134 | B3 | N | 4-OH |
| 135 | B2 | N | 4-OC₂H₅ |
| 136 | B2 | N | 3-OCH₃; 4-OCH₃; hydrate (1:1) |
| 137 | B3 | N | 3-OH |
| 138 | B3 | N | 3-OCH₃; 4-OH |
| 139 | B2 | CH | 3-OCH₃; 4-OCH₃; 5-OCH₃ |
| 140 | B2 | CH | 3-OCH₃; 4-OCH₃ |
| 141 | B3 | CH | 2-Cl; 4-Cl |
| 142 | B3 | CH | 3-OCH₃; 4-OH |
| 143 | B3 | CH | 3-Cl; 4-Cl |
| 144 | B2 | CH | 4-NO₂; (A) |
| 145 | B7 | CH | 4-NH₂; (A) |
| 146 | B2 | CH | 4-NO₂; (B) |
| 147 | B7 | CH | 4-NH₂; (B) |
| 148 | B3 | CH | 3-I; 4-NH₂ |
| 149 | B3 | CH | 3-I; 4-NH₂; (B) |
| 150 | B3 | CH | 3-I; 4-NH₂; (A) |
| 151 | B2 | CH | 4-NO₂ |
| 152 | B7 | CH | 4-NH₂ |

TABLE 4

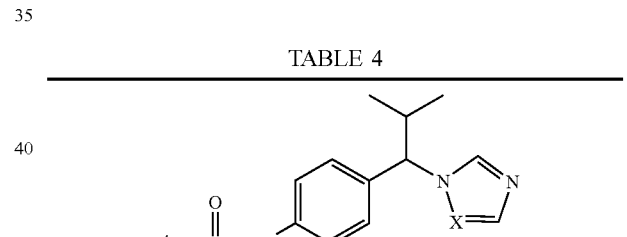

| Co No (Ex No) | X; R⁴; stereochemical descriptor if not racemic and/or addition salt |
|---|---|
| 153 (B1) | N; CH₃ |
| 154 (B2) | N; C(CH₃)=CHC₆H₅; (E) |
| 155 (B2) | N; CH=CHC₆H₅; (E) |
| 156 (B2) | N; C(CH₃)=CH(3-Cl—C₆H₄); (E) |
| 157 (B2) | N; C(CH₃)=CH(4-F—C₆H₄); (E) |
| 158 (B2) | N; C(CH₃)=CH(4-pyridinyl); (E) |
| 159 (B2) | N; C(CH₃)=CH(4-CF₃—C₆H₄); (E) |
| 160 (B2) | N; CF=CHC₆H₅; (Z) |
| 161 (B2) | N; 1,3-benzodioxolan-2-yl |
| 162 (B2) | N; (2,3-dihydro-1,4-benzodioxin-2-yl)methyl |
| 163 (B2) | CH; C₂H₅ |
| 164 (B4) | CH; CH(CH₃)—CH₂(C₆H₅) |
| 165 (B2) | CH; CH(CH₃)—CH=CHC₆H₅; (E) |
| 166 (B2) | CH; C₆H₅ |
| 167 (B2) | CH; 2-benzofuranyl |
| 168 (B2) | CH; 2-benzothienyl |
| 169 (B2) | CH; 2-furanyl |
| 170 (B2) | CH; 2-pyrazinyl |
| 171 (B2) | CH; C(CH₃)=C(C₆H₅)(3-pyridinyl); (E + Z) |
| 172 (B2) | CH; 3-furanyl |
| 173 (B2) | CH; 3-thienyl |
| 174 (B2) | CH; 1-cyclohexyl |

TABLE 4-continued

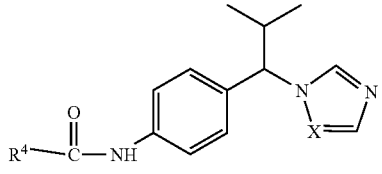

| Co No (Ex No) | X; R⁴; stereochemical descriptor if not racemic and/or addition salt |
|---|---|
| 175 (B2) | CH; 2,3-dihydro-1,4-benzodioxin-2-yl |
| 176 (B2) | CH; C(CH₃)=C(C₆H₅)(CH₃); (E) |
| 177 (B5) | CH; H |
| 178 (B2) | CH; 2-indolyl |
| 179 (B2) | CH; 2-naphthalenyl |
| 180 (B2) | CH; 1-methyl-2-indenyl |
| 181 (B2) | CH; 2-oxolanyl |
| 182 (B2) | CH; 1-naphthalenyl |
| 183 (B2) | CH; OC₂H₅ |
| 184 (B2) | CH; 1-methylbenzotriazol-6-yl |
| 185 (B2) | CH; 3-oxolanyl |
| 186 (B2) | CH; 2-phenyl-4-thiazolyl |
| 187 (B2) | CH; 2-thienyl |
| 188 (B2) | CH; (CH₂)₂CH₂Cl |
| 189 (B2) | CH; C(CH₃)(C₆H₅)₂ |
| 190 (B2) | CH; 1-C₆H₅-cyclopropyl |
| 191 (B2) | CH; 1-C₆H₅-cyclopentyl |
| 192 (B2) | CH; cyclopentyl |
| 193 (B2) | CH; cyclohexyl |
| 194 (B3) | CH; 4-pyridinyl |
| 195 (B3) | CH; 1-methyl-2-pyrrolyl |
| 196 (B3) | CH; 3-pyridinyl |
| 197 (B2) | CH; 2-methylcyclopropyl |
| 198 (B3) | CH; C≡C(C₆H₅) |
| 199 (B3) | CH; cyclopropyl |
| 200 (B2) | CH; 1-C₆H₅-cyclohexyl |
| 201 (B2) | CH; 1-methylcyclohexyl |
| 202 (B2) | CH; 2-methylcyclohexyl |
| 203 (B3) | CH; C(CH₃)=C(C₆H₅)—C₂H₅; (Z) |
| 204 (B2) | CH; 2-phenylcyclopropyl; oxalic acid (1:1) |
| 205 (B2) | CH; 3,4-dihydro-2(1H)-quinolinone-6-yl |
| 206 (B2) | CH; OC₆H₅ |
| 207 (B3) | CH; C(CH₃)=C(C₆H₅)(2-furanyl); (E) |
| 208 (B3) | CH; 2-pyridinyl |
| 209 (B2) | CH; CH(CH₃)CH₃ |
| 210 (B3) | CH; CH₂—S—CH₂C₆H₅ |
| 211 (B3) | CH; CH₂—OC₆H₅ |
| 212 (B3) | CH; CH₂—OCH₃ |
| 213 (B3) | CH; CH₂—NH—C₆H₅ |
| 214 (B3) | CH; 6-quinoxalinyl |
| 215 (B3) | CH; 2-quinolinyl |
| 216 (B3) | CH; 2-quinoxalinyl |
| 217 (B2) | CH; 3,4-dihydro-2H-1-benzopyran-2-yl |
| 218 (B6a) | CH; (CH₂)₃C(=O)OH |
| 219 (B6b) | CH; (CH₂)₃C(=O)OC₂H₅ |
| 220 (B2) | CH; 5-bromo-2-furanyl |
| 221 (B2) | CH; 3-F—C₆H₄ |
| 222 (B3) | CH; C(CH₃)₂[O(4-Cl—C₆H₄)] |
| 223 (B3) | CH; CH₂—S—C₆H₅ |
| 224 (B3) | CH; (2-pyrimidinylthio)methyl |
| 225 (B3) | CH; 5-methyl-2-pyrazinyl |
| 226 (B2) | CH; 3-methyl-2-furanyl |
| 227 (B3) | CH; 4-quinolinyl |

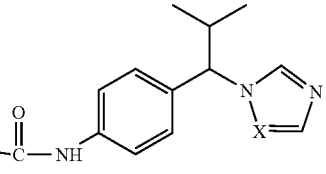

| Co No (Ex No) | X; R⁴; stereochemical descriptor if not racemic and/or addition salt |
|---|---|
| 228 (B3) | CH; 1,2-dihydro-2(1H)-pyridinone-3-yl |
| 229 (B3) | CH; 1-isoquinolinyl |
| 230 (B2) | CH; 2,3-dihydro-1,4-benzodioxin-5-yl |
| 231 (B2) | CH; 3,4-(OCH₃)₂—C₆H₃ |
| 232 (B2 | CH; 1,3-benzodioxolan-5-yl |
| 233 (B3) | CH; 5-quinoxalinyl |
| 234 (B2) | CH; 1,4-benzodioxin-2-yl |
| 235 (B2) | CH; 2-furanylmethyl |
| 236 (B3) | CH; C(OH)(CH₃)₂ |
| 237 (B2) | CH; (2,3-dihydro-1,4-benzodioxin-2-yl)methyl |
| 238 (B2) | CH; 4-(C₆H₅)—C₆H₄ |
| 239 (B3) | CH; (4-pyridinylthio)methyl |
| 240 (B3) | CH; (2-naphtalenyl)methyl |
| 241 (B3) | CH; 3-quinolinyl |
| 242 (B3) | CH; 3,5-dimethyl-4-isoxazolyl |
| 243 (B2) | CH; 2,3-dihydro-1,4-benzoxathiin-2-yl |
| 244 (B3) | CH; 2-thienylmethyl |
| 245 (B3) | CH; 3-thienylmethyl |
| 246 (B3) | CH; 1-naphtalenylmethyl |
| 247 (B3) | CH; 2-pridinylmethyl |
| 248 (B2) | CH; 1,3-benzodioxolan-2-yl |
| 249 (B3) | CH; CH(OH)—CH₃ |
| 250 (B3) | CH; 5-methyl-3-phenyl-4-isoxazolyl |
| 251 (B3) | CH; 3-pyridinylmethyl |
| 252 (B2) | CH; 5,6,7,8-tetrahydro-5,5,8,8-tetramethyl-2-naphtalenyl |
| 253 (B2) | CH; 3,4-dihydro-2H-1-benzopyran-3-yl |
| 254 (B2) | CH; 2H-1-benzopyran-3-yl |
| 255 (B2) | CH; (2,3-dihydro-1,4-benzodioxin-6-yl)methyl |
| 256 (B2) | CH; (5,6,7,8-tetrahydro-5,5,8,8-tetramethyl-22-naphtalenyl)methyl |
| 257 (B1) | CH; CH₃; (A) |
| 258 (B1) | CH; CH₃; (B) |
| 259 (B8) | CH; CH₂(3-iodo-4-azido-C₆H₃); (B) |
| 260 (B8) | CH; CH₂(3-iodo-4-azido-C₆H₃); (A) |
| 261 (B3) | CH; CH₂—NH—C(=O)—C₆H₅ |
| 262 (B3) | CH; CH₂—NH—C(=O)—O—CH₂—C₆H₅ |
| 263 (B23) | CH; N(CH₃)—CH₂—C₆H₅ |
| 264 (B6a) | CH; CH₂-[1-(CH₂COOH)cyclopentyl] |
| 265 (B6a) | CH; (CH₂)₂—C(=O)—OH |
| 266 (B30) | CH; NH₂ |
| 267 (B23) | CH; NH—CH₃ |
| 268 (B23) | CH; NH—C(CH₃)₂ |
| 269 (B23) | CH; NH—CH₂—C₆H₅ |
| 270 (B23) | CH; NH-(3-pyridinyl) |
| 271 (B23) | CH; NH-(2-pyrazinyl) |
| 272 (B31) | CH; NH-(1-naphtalenyl) |
| 273 (B23) | CH; NH—CH₂-(4-Cl—C₆H₄) |
| 274 (B23) | CH; NH-(2-pyridinyl) |
| 275 (B23) | CH; NH-(4-pyridinyl) |

TABLE 4-continued

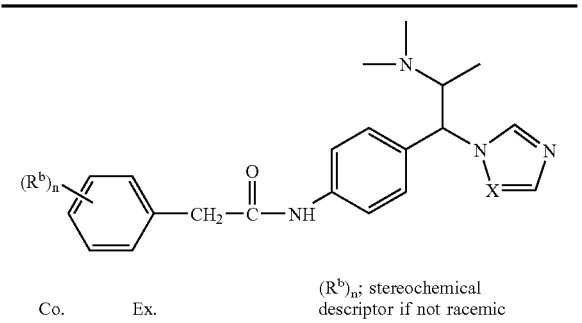

| Co No (Ex No) | X; R⁴; stereochemical descriptor if not racemic and/or addition salt |
|---|---|
| 276 (B23) | CH; NNH-(6-benzodioxanyl) |
| 277 (B23) | CH; NH-(1-CH₃-2-benzimidazolyl) |

TABLE 5

| Co. No. | Ex. No. | X | (Rᵇ)ₙ; stereochemical descriptor if not racemic and/or addition salt |
|---|---|---|---|
| 278 | B2 | N | 3-OCH₃; 4-OCH₃; (A) |
| 279 | B3 | N | 3-Cl; 4-OCH₃; (A) |
| 280 | B3 | N | 3-CH₃; 4-CH₃; (B) |
| 281 | B3 | N | 4-OCH₃; 3-CH₃; (B) |
| 282 | B3 | N | 3-CH₃; 4-CH₃; (A) |
| 283 | B3 | N | 4-Cl; (B) |
| 284 | B3 | N | 3-Cl; 4-OH; (A) |
| 285 | B3 | N | 3-OC₂H₅; 4-OC₂H₅; (A) |
| 286 | B3 | N | 3-CH₃; 4-OCH₃; (A) |
| 287 | B3 | N | 3-OCH₃; 4-OCH₃; (B) |
| 288 | B3 | N | 3-Cl; 4-OCH₃; (B) |
| 289 | B3 | N | 3-Cl; 4-OH; (B) |
| 290 | B3 | N | 3-CH₃; 4-CH₃; 5-CH₃; (A) |
| 291 | B3 | N | 3-CH₃; 4-CH₃; 5-CH₃; (B) |
| 292 | B3 | N | 3,4,5-(OCH₃)₃; (B) |
| 293 | B3 | N | 3-OC₂H₅; 4-OC₂H₅; (B) |
| 294 | B3 | N | 3-OCH₃; 4-CH₃; (A) |
| 295 | B3 | N | 3-OCH₃; 4-CH₃; (B) |
| 296 | B3 | N | 3-OCH₃; 4-Cl; (A) |
| 297 | B3 | N | 3-OCH₃; 4-Cl; (B) |
| 298 | B10 | N | 3-Cl; 4-OH; (A, A) |
| 299 | B10 | N | 3-Cl; 4-OH; (A, B) |
| 300 | B3 | CH | 3-OC₂H₅; 4-OC₂H₅; (A) |
| 301 | B3 | CH | 3-OC₂H₅; 4-OC₂H₅; (B) |
| 302 | B3 | CH | 3,4,5-(OCH₃)₃; (A) |
| 303 | B3 | CH | 3-Cl; 4-OH; (A) |
| 304 | B2 | CH | 3-Cl; 4-OCH₃; (A) |
| 305 | B3 | CH | 3-Cl; 4-OCH₃; (B) |
| 306 | B3 | CH | 3-CH₃; 4-CH₃; (B) |
| 307 | B3 | CH | 3-Cl; 4-OH; (B) |
| 308 | B3 | CH | 3-CH₃; 4-CH₃; 5-CH₃; (A) |
| 309 | B3 | CH | 3-CH₃; 4-CH₃; 5-CH₃; (B) |
| 310 | B3 | CH | 3-OCH₃; 4-Cl; (A) |
| 311 | B3 | CH | 3-OCH₃; 4-Cl; (B) |
| 312 | B3 | CH | 3-CH₃; 4-OCH₃; (A) |
| 313 | B3 | CH | 3-CH₃; 4-OCH₃; (B) |
| 314 | B3 | CH | 3-OCH₃; 4-CH₃; (A) |
| 315 | B3 | CH | 3-OCH₃; 4-CH₃; (B) |

TABLE 5-continued

| Co. No. | Ex. No. | X | (Rᵇ)ₙ; stereochemical descriptor if not racemic and/or addition salt |
|---|---|---|---|
| 316 | B3 | CH | 4-OCH(CH₃)₂; (B) |
| 317 | B3 | CH | 4-N(CH₃)₂; (A) |
| 318 | B3 | CH | 3-OCH₃; 4-OCH₃; (A) |
| 319 | B3 | CH | 4-O(CH₂)₃CH₃; (A) |
| 320 | B3 | CH | 4-O(CH₂)₃CH₃; (B) |
| 321 | B3 | CH | 4-OCH(CH₃)₂; (A) |
| 784 | B34 | N | 4-Cl; (B, A) |
| 785 | B34 | N | 4-Cl; (B, B) |

TABLE 6

| Co No (Ex No) | X; R⁴; stereochemical descriptor if not racemic and/or addition salt |
|---|---|
| 322 (B3) | N; (2,3-dihydro-1,4-benzodioxin-6-yl)methyl; (A) |
| 323 (B2) | N; OC₆H₅; (A) |
| 324 (B2) | N; 3,4-diOCH₃—C₆H₃; (A) |
| 325 (B2) | N; (1,3-benzodioxolan-5-yl)-methyl; (A) |
| 326 (B3) | N; (CH₂)₃(3,4-diOCH₃—C₆H₃); (A) |
| 327 (B3) | N; 3,4-diOCH₃—C₆H₃; (B) |
| 328 (B3) | N; (CH₂)₂(3,4-diOCH₃—C₆H₃); (B) |
| 329 (B3) | N; (CH₂)₃(3,4-diOCH₃—C₆H₃); (B) |
| 330 (B3) | N; (1,3-benzodioxolan-5-yl)methyl; (B) |
| 331 (B5) | N; H; (B) |
| 332 (B3) | N; (C(CH₃)=CH(C₆H₅); [B-(E)] |
| 333 (B3) | N; (2,3-dihydro-1,4-benzodioxin-6-yl)methyl; (B) |
| 334 (B2) | N; OC₆H₅; (B) |
| 335 (B5) | N, H; (A) |
| 336 (B3) | CH; (CH₂)₃(3,4-diOCH₃—C₆H₃); (B) |
| 337 (B3) | CH; (1,3-benzodioxolan-5-yl)-methyl; (B) |
| 338 (B3) | CH; (2,3-dihydro-1,4-benzodioxin-6-yl)methyl; (A) |
| 339 (B3) | CH; (2,3-dihydro-1,4-benzodioxin-6-yl)methyl; (B) |
| 340 (B2) | CH; (1,3-benzodioxolan-5-yl)methyl; (A) |

TABLE 6-continued

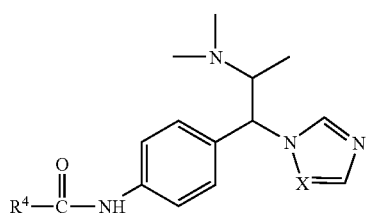

| Co No (Ex No) | X; R⁴; stereochemical descriptor if not racemic and/or addition salt |
|---|---|
| 341 (B3) | CH; 3,4-diOCH₃—C₆H₃; (A) |
| 342 (B3) | CH; 3,4-diOCH₃—C₆H₃; (B) |
| 343 (B2) | CH; OC₆H₅; (A) |
| 344 (B2) | CH; OC₆H₅ |
| 345 (B5) | CH; H; (A) |
| 346 (B3) | CH; (CH₂)₂(4-OC₂H₅—C₆H₄); (A) |
| 347 (B9) | CH; 4-methylpiperazinyl; (A) |
| 348 (B3) | CH; (CH₂)₂(4-OC₂H₅—C₆H₄) |
| 349 (B9) | CH; 4-methylpiperazinyl; (B) |
| 350 (B3) | CH; CH[O(2-OCH₃—C₆H₄)]; (A) |
| 351 (B3) | CH; CH[O(2-OCH₃—C₆H₄)]; (B) |
| 352 (B3) | CH; (4-CH₃-piperazinyl)methyl; (A) |
| 353 (B3) | CH; (4-CH₃-piperazinyl)methyl; (B) |
| 354 (B3) | CH; (4-CH₃-piperazinyl)ethyl |

TABLE 7

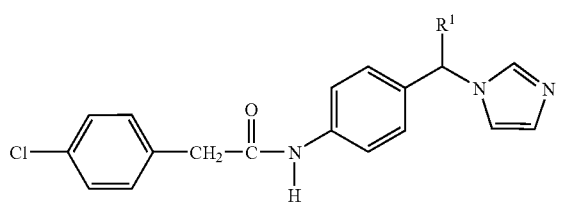

| Co No (Ex No) | R¹; stereochemical descriptor if not racemic and/or addition salt |
|---|---|
| 355 (B2) | (CH₂)₂CH(CH₃)₂ |
| 356 (B3) | 4-Cl—C₆H₄ |
| 357 (B2) | C₆H₅ |
| 358 (B2) | CH₃ |
| 359 (B2) | CH₂CH(CH₃)₂ |
| 360 (B2) | CH₂—C(CH₃)₃ |
| 361 (B2) | 3-CF₃—C₆H₄ |
| 362 (B2) | cyclohexyl |
| 363 (B2) | (CH₂)₂CH₃ |
| 364 (B2) | CH(CH₃)CH₂CH₃ |
| 365 (B2) | C(CH₃)₃ |
| 366 (B3) | 1-(1-piperidinyl)ethyl; (A) |
| 367 (B2) | CH[N(CH₃)₂]CH₃; (A) |
| 368 (B2) | CH[N(CH₃)₂]CH₃; (B) |
| 369 (B2) | CH(S—C₆H₅)CH₃; (B) |
| 370 (B2) | CH(O—C₆H₅)CH₃; (A) |
| 371 (B2) | CH(CH₃)CH₂CN; (A + B) |
| 372 (B2) | C₂H₅ |
| 373 (B2) | 5,6,7,8-tetrahydro-5,5,8,8-tetramethyl-2-naphtalenyl |
| 374 (B2) | CH(CH₃)C₃H₇; (B) |
| 375 (B2) | CH₂[N(CH₃)₂] |
| 376 (B2) | CH(S—C₆H₅)CH₃; (A) |
| 377 (B2) | CH(CH₃)CH₂C₆H₅ |

TABLE 8

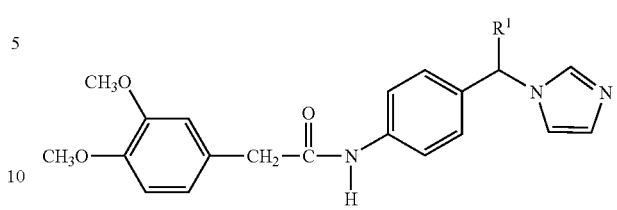

| Co No (Ex No) | R¹; stereochemical descriptor if not racemic and/or addition salt |
|---|---|
| 378 (B2) | CH(C₃H₇)₂ |
| 379 (B3) | CH(CH₃)[N(CH₃)₂]; (B) |
| 380 (B3) | CH₂[N(CH₃)₂] |
| 381 (B3) | CH[C(=O)OC₂H₅]CH₃; (A) |
| 382 (B3) | CH[C(=O)OC₂H₅]CH₃; (B) |
| 383 (B3) | CH[N(C₂H₅)₂]CH₃; (B) |
| 384 (B3) | CH(CH₃)C₅H₁₁; (A) |
| 385 (B3) | CH(CH₃)C₅H₁₁; (B) |
| 386 (B18) | CH(CH₃)CH₂OH; (A) |
| 387 (B3) | CH[N(C₂H₅)₂]CH₃; (A) |
| 388 (B3) | CH[N(CH₃)₂]C₂H₅; (B) |
| 389 (B3) | [1-CH₃-2-(1-piperidinyl)]C₂H₅; (B) |
| 390 (B3) | [1-CH₃-2-(1-piperidinyl)]C₂H₅; (A) |
| 391 (B3) | CH(CH₃)[CH₂[N(CH₃)₂]]; (B) |
| 392 (B3) | CH(CH₃)[CH₂[N(CH₃)₂]]; (A) |
| 393 (B3) | [1-N(CH₃)₂]C₃H₇; (A) |
| 394 (B18) | (1-CH₃)C₂H₅OH; (B) |
| 395 (B3) | CH₂C(=O)OC₂H₅ |
| 396 (B3) | CH[N(CH₃)(CH₂C₆H₅)]CH₃; (B) |
| 397 (B17) | CH₂OCH₃ |
| 398 (B3) | CH[N(CH₃)(CH₂C₆H₅)]CH₃; (A) |
| 399 (B3) | CH[N(CH₃)(CH₂C₆H₅)]CH₃ |
| 400 (B19) | CH[NH(CH₃)]CH₃; (A) |
| 401 (B19) | CH[NH(CH₃)]CH₃; (B); hydrate (1:1) |
| 402 (B20) | CH(OH)CH₃; (B); hydrate (1:1) |
| 403 (B18) | (CH₂)₂(OH) |
| 404 (B21) | CH(CH₃)CH₂OCH₃; (A) |
| 405 (B21) | CH(CH₃)CH₂OCH₃; (B) |
| 406 (B3) | CH[N(CH₃)(C₄H₉)]CH₃; (A) |
| 407 (B3) | CH[N(CH₃)[(CH₂)₂N(CH₃)₂]]CH₃; (A) |
| 408 (B3) | 1-(4-morpholinyl)ethyl; (A) |
| 409 (B3) | 1-(4-morpholinyl)ethyl; (B) |
| 410 (B3) | 1-methyl-3-piperidinyl; (A) |
| 411 (B3) | 1-methyl-2-piperidinyl; (A) |
| 412 (B3) | 1-(4-methyl-1-piperazinyl)ethyl; (A); hydrate (1:1) |
| 413 (B3) | CH[N(CH₃)(C₃H₇)]CH₃; (A) |
| 414 (B3) | CH[N(CH₃)(C₃H₇)]CH₃; (B) |
| 415 (B3) | CH[N(CH₃)[(CH₂)₂C₆H₅]]CH₃ |
| 416 (B3) | CH[N(CH₃)(C₂H₅)]CH₃; (A) |
| 417 (B3) | CH[OC(=O)N(CH₂C₆H₅)₂]CH₃; (A) |
| 418 (B3) | CH[N(CH₂C₆H₅)₂]CH₃; (B) |
| 419 (B3) | CH[N(CH₂C₆H₅)₂]CH₃; (A) |

TABLE 9

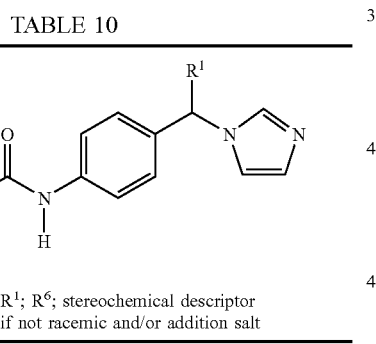

| Co. No. | Ex. No. | X | R¹ | R³ | R⁴; stereochemical descriptor if not racemic and/or addition salt |
|---|---|---|---|---|---|
| 420 | B3 | CH | $C_6H_5$ | H | $CH(OH)C_6H_5$ |
| 421 | B2 | CH | $CH(CH_3)_2$ | $CH_3$ | $C(CH_3)=CHC_6H_5$; (E) |
| 422 | B2 | CH | $CH(CH_3)_2$ | $C_2H_5$ | $C(CH_3)=CHC_6H_5$; (E) |
| 423 | B3 | CH | 4-Cl—$C_6H_4$ | H | $CH(OH)C_6H_5$ |
| 424 | B2 | CH | $C_6H_5$ | H | 2-pyrazinyl |
| 425 | B2 | CH | $C_6H_5$ | H | 2,3-dihydro-1,4-benzodioxin-2-yl |
| 426 | B2 | CH | $C_6H_5$ | H | (2,3-dihydro-1,4-benzodioxin-2-yl)-methyl |
| 427 | HB2 | CH | $CH(C_2H_5)_2$ | $CH_3$ | $CH_2(3,4\text{-diOCH}_3\text{—}C_6H_3)$ |
| 428 | B3 | CH | $CH[N(CH_3)_2]CH_3$ | H | $CH_2(3,4,5\text{-triOCH}_3\text{—}C_6H_2)$; (B) |
| 429 | B3 | CH | $CH[N(CH_3)_2]CH_3$ | H | $(CH_2)_2(3,4\text{-diOCH}_3\text{—}C_6H_3)$; (B) |
| 430 | B3 | CH | $CH[N(CH_3)_2]CH_3$ | H | $(CH_2)_2(3,4\text{-diOCH}_3\text{—}C_6H_3)$; (A) |
| 431 | B3 | CH | $CH[N(CH_3)_2]CH_3$ | H | $(CH_2)_3(3,4\text{-diOCH}_3\text{—}C_6H_3)$; (A); oxalic acid (1:1) |
| 432 | B3 | CH | 2-butyl | H | $CH_2(3\text{-OCH}_3\text{-4-OH}\text{—}C_6H_3)$ |
| 433 | B3 | CH | $CH_2[N(CH_3)_2]$ | H | $CH_2(3,4\text{-diOCH}_3\text{—}C_6H_3)$ |
| 434 | B3 | CH | $CH_2[N(CH_3)_2]$ | H | 3,4-diOCH$_3$—$C_6H_3$ |
| 435 | B2 | CH | $CH_2[N(CH_3)_2]$ | H | $OC_6H_5$ |
| 436 | B9 | CH | $CH_2[N(CH_3)_2]$ | H | 4-methyl-1-piperazinyl |
| 437 | B2 | N | $CH(CH_3)[N(CH_3)_2]$ | $CH_3$ | $CH_2(3,4\text{-diOCH}_3\text{—}C_6H_3)$; (B) |
| 438 | B2 | N | $CH(CH_3)[N(CH_3)_2]$ | $CH_3$ | $CH_2(3,4\text{-diOCH}_3\text{—}C_6H_3)$; (A) |
| 439 | B2 | CH | $CH(CH_3)[N(CH_3)_2]$ | $CH_3$ | $CH_2(3,4\text{-diOCH}_3\text{—}C_6H_3)$; (A) |

TABLE 10

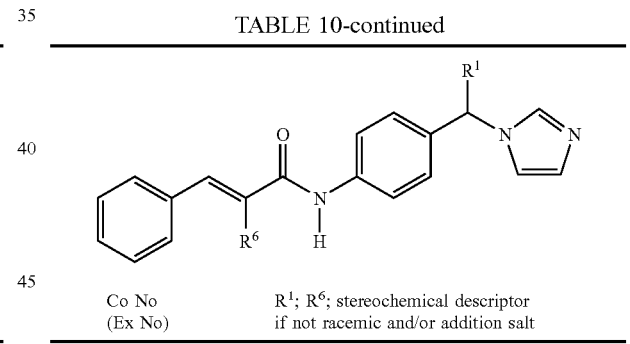

| Co No (Ex No) | R¹; R⁶; stereochemical descriptor if not racemic and/or addition salt |
|---|---|
| 440 (B2) | 4-Cl—$C_6H_4$; H |
| 441 (B2) | 3-Cl—$C_6H_4$; H |
| 442 (B2) | 3-F—$C_6H_4$; H |
| 443 (B2) | 4-F—$C_6H_4$; H |
| 444 (B2) | $C_6H_5$; $C_6H_5$ |
| 445 (B2) | $C_6H_5$; $CH_3$ |
| 446 (B2) | 4-F—$C_6H_4$; $CH_3$ |
| 447 (B2) | 4-Cl—$C_6H_4$; $C_6H_5$ |
| 448 (B2) | 3-Cl—$C_6H_4$; $CH_3$ |
| 449 (B2) | 3-Cl—$C_6H_4$; $C_6H_5$ |
| 450 (B2) | 4-F—$C_6H_4$; $C_6H_5$ |
| 451 (B2) | 4-Cl—$C_6H_4$; $CH_3$ |
| 452 (B2) | $C_6H_5$; $C_6H_5$ |
| 453 (B2) | $C_6H_5$; $C_3H_7$ |
| 454 (B2) | $CH(CH_3)_2$; $C_6H_5$ |
| 455 (B2) | $CH(CH_3)_2$; $CH_3$; (E) |
| 456 (B2) | $CH(CH_3)_2$; 2-$CH_3$—$C_6H_4$ |
| 457 (B2) | $CH(CH_3)_2$; $C_2H_5$ |
| 458 (B10) | $CH(CH_3)_2$; $CH_3$; (+)-[A-(E)] |
| 459 (B10) | $CH(CH_3)_2$; $CH_3$; (−)-[B-(E)] |
| 460 (B2) | $C_2H_5$; $CH_3$; (E) |
| 461 (B2) | $CH(CH_3)_2$; F; (E) |
| 462 (B2) | $C_4H_9$; $CH_3$; (E) |
| 463 (B2) | cyclohexyl; $CH_3$; (E) |
| 464 (B2) | $CH(CH_3)_2$; $C_3H_7$; (E) |
| 465 (B2) | $CH(CH_3)_2$; $C_4H_9$; (E) |
| 466 (B2) | $CH_3$; $CH_3$; (E) |
| 467 (B2) | $C_3H_7$; $CH_3$; (E) |
| 468 (B2) | cyclohexyl; $C_6H_5$; (E) |
| 469 (B2) | cyclopropyl; $CH_3$; (E) |
| 470 (B2) | cyclopentyl; $CH_3$; (E) |
| 471 (B3) | $CH(CH_3)_2$; $CH(CH_3)_2$; (E) |
| 472 (B3) | $CH(CH_3)_2$; cyclopentyl; (E) |
| 473 (B3) | $CH(CH_3)_2$; cyclohexyl; (E) |
| 474 (B2) | $CH_2CH(CH_3)_2$; $CH_3$; (E) |
| 475 (B2) | $(CH_2)_2CH(CH_3)_2$; $CH_3$; (E) |
| 476 (B2) | $CH_2C(CH_3)_3$; $CH_3$; (E); hydrate (2:1) |
| 477 (B2) | 1,3-dioxan-5-yl; $CH_3$; (E) |
| 478 (B2) | $CH(C_2H_5)_2$; $CH_3$; (E) |
| 479 (B2) | $CH=CH\text{—}CH(CH_3)_2$; $CH_3$; (E, E) |
| 480 (B2) | $CH(CH_3)C_2H_5$; $CH_3$; (E) |
| 481 (B2) | $C(CH_3)_3$; $CH_3$; (E) |
| 482 (B2) | $CH(CH_3)C_3H_7$; $CH_3$; [A-(E)] |
| 483 (B2) | $CH(S\text{—}C_6H_5)CH_3$; $CH_3$; (A) |
| 484 (B2) | $CH(S\text{—}C_6H_5)CH_3$; $CH_3$; (B) |

TABLE 10-continued

[Structure: cinnamide with R⁶ substituent, N-H linked to para-substituted phenyl bearing CHR¹-imidazolyl group]

| Co No (Ex No) | R¹; R⁶; stereochemical descriptor if not racemic and/or addition salt |
|---|---|
| 485 (B2) | CH(C₆H₅)₂; CH₃; (E) |
| 486 (B2) | CH(C₃H₇)₂; CH₃; (E) |
| 487 (B2) | CH(CH₃)C₅H₁₁; CH₃; [A-(E)] |
| 488 (B2) | CH(CH₃)C₅H₁₁; CH₃; [B-(E)] |
| 489 (B2) | CH(C₆H₅)CH₃; CH₃; [A-(E)] |
| 490 (B2) | CH(C₆H₅)CH₃; CH₃; [B-(E)] |
| 491 (B2) | 5,5,8,8-tetramethyl-5,6,7,8-tetrahydro-2-naphtalenyl; CH₃; (E) |
| 492 (B2) | CH(C₂H₅)C₅H₁₁; CH₃; [A-(E)] |
| 493 (B2) | CH(C₂H₅)C₄H₉; CH₃; (E) |
| 494 (B2) | CH(C₂H₅)C₅H₁₁; CH₃; [B-(E)] |
| 496 (B3) | CH[N(CH₃)₂]CH₃; CH₃; [B-(E)] |
| 497 (B2) | C₆H₅; H |
| 498 (B2) | H; H |
| 499 (B2) | CH(CH₃)₂; H |
| 500 (B2) | 4-Br—C₆H₄; H |
| 501 (B2) | 4-CH₃—C₆H₄; H |
| 502 (B2) | CH(CH₃)₂; H; (E) |
| 786 (B3) | 2,5-diCl—C₆H₃; CH₃; (E) |

TABLE 11

[Structure: cinnamide with R⁶ and R⁷ substituents, N-H linked to para-substituted phenyl bearing CHR¹-imidazolyl group]

| Co No (Ex No) | R¹; R⁶; R⁷; stereochemical descriptor if not racemic and/or addition salt |
|---|---|
| 503 (B2) | C₆H₅; H; C₆H₅ |
| 504 (B2) | 4-Cl—C₆H₄; H; C₆H₅ |
| 505 (B2) | 3-Cl—C₆H₄; H; C₆H₅ |
| 506 (B2) | 4-F—C₆H₄; H; C₆H₅ |
| 507 (B2) | 4-Cl—C₆H₄; H; C₂H₅ |
| 508 (B2) | 4-F—C₆H₄; H; CH₃ |
| 509 (B2) | H; H; C₆H₅ |
| 510 (B2) | CH₃; H; C₆H₅ |
| 511 (B2) | CH(CH₃)₂; H; C₆H₅ |
| 512 (B2) | 4-Cl—C₆H₄; H; CH₃ |
| 513 (B3) | 4-Cl—C₆H₄; H; C₄H₉ |
| 514 (B3) | 4-Cl—C₆H₄; H; cyclohexyl; (E + Z) |
| 515 (B3) | 4-Cl—C₆H₄; H; CH(CH₃)₂; (E + Z) |
| 516 (B2) | 4-Cl—C₆H₄; H; 3-pyridinyl |
| 517 (B2) | 4-F—C₆H₄; H; 3-pyridinyl |
| 518 (B3) | CH(CH₃)₂; CH₃; 3-thienyl; (E + Z) |
| 519 (B3) | CH(CH₃)₂; CH₃; C₃H₇; (E + Z) |
| 520 (B3) | 4-Cl—C₆H₄; H; 3,5-diCl—C₆H₃ |

TABLE 12

[Structure: acetamide CH₃—C(=O)—NH linked to para-substituted phenyl bearing CHR¹-imidazolyl group]

| Co No (Ex No) | R¹; stereochemical descriptor if not racemic and/or addition salt |
|---|---|
| 521 (B17) | CH(CH₃)₂ |
| 522 (B1) | 3-Cl—C₆H₄ |
| 523 (B1) | 3-F—C₆H₄ |
| 524 (B1) | 3-CF₃—C₆H₄ |
| 525 (B1) | cyclohexyl |
| 526 (B17) | cyclopropyl |
| 527 (B17) | cyclopentyl |
| 528 (B17) | (CH₂)₂CH(CH₃)₂ |
| 529 (B17) | CH₂C(CH₃)₃ |
| 530 (B17) | 1,3-dioxan-5-yl |
| 531 (B1) | CH(C₅H₅)₂ |
| 532 (B17) | CH=CH—CH(CH₃)₂ |
| 533 (B1) | CH(CH₃)C₂H₅ |
| 534 (B1) | C(CH₃)₃ |
| 535 (B1) | CH[N(CH₃)₂]CH₃; hydrate (1:1) |
| 536 (B1) | CH(CH₃)(n-C₃H₇) |
| 537 (B1) | 1-(1-piperidinyl)ethyl |
| 538 (B1) | CH(S—C₆H₅)CH₃; (A + B) |
| 539 (B1) | CH(O—C₆H₅)CH₃ |
| 540 (B1) | CH(CH₃)CH₂CN |
| 541 (B1) | CH(C₆H₅)₂ |
| 542 (B1) | CH(C₂H₅)(n-C₃H₇) |
| 543 (B1) | CH(n-C₃H₇)₂ |
| 544 (B17) | CH(C₆H₅)CH₃ |
| 545 (B17) | 5,5,8,8-tetramethyl-5,6,7,8-tetrahydro-2-naphtalenyl |
| 546 (B17) | CH(CH₃)(n-C₅H₁₁) |
| 547 (B17) | CH(C₂H₅)(n-C₅H₁₁) |
| 548 (B1) | CH₂N(CH₃)₂ |
| 549 (B1) | CH(C₂H₅)(n-C₄H₉) |
| 550 (B17) | 1-(ethoxycarbonyl)ethyl |
| 551 (B1) | CH[N(CH₃)₂]CH₃; (A); hydrate (1:1) |
| 552 (B1) | CH[N(CH₃)₂]CH₃; (B) |
| 553 (B1) | CH(CH₃)[CH₂(C₆H₅)] |
| 554 (B1) | CH[N(C₂H₅)₂]CH₃; (A) |
| 555 (B1) | CH[N(C₂H₅)₂]CH₃; (B) |
| 556 (B1) | CH[N(C₂H₅)₂]CH₃ |
| 557 (B1) | CH[N(CH₃)₂]C₂H₅; (A) |
| 558 (B1) | CH[N(CH₃)₂]C₂H₅; (B) |
| 559 (B1) | CH[N(CH₃)₂]C₂H₅ |
| 560 (B1) | (ethoxycarbonyl)methyl |
| 561 (B17) | CH[N(CH₃)(CH₂—C₆H₅)]CH₃ |
| 562 (B1) | CH[N(CH₃)(n-C₄H₉)]CH₃ |
| 563 (B1) | CH[N(CH₃)[(CH₂)₂N(CH₃)₂]]CH₃ |
| 564 (B17) | 1-(4-morpholinyl)ethyl |
| 565 (B1) | CH[N(CH₃)₂]C₂H₅ |
| 566 (B1) | CH[N(CH₃)(C₂H₅)]CH₃ |
| 567 (B1) | 1-methyl-3-piperidinyl |
| 568 (B1) | 1-methyl-2-piperidinyl; (A) |
| 569 (B1) | 1-(4-methyl-1-piperazinyl)ethyl |
| 570 (B1) | CH[N(CH₃)(n-C₃H₇)]CH₃ |
| 571 (B1) | CH[N(CH₃)(C₂H₅—C₆H₅)]CH₃ |
| 572 (B1) | CH[N(CH₂—C₆H₅)₂]CH₃ |
| 573 (B1) | CH[OC(=O)N(CH₂—C₆H₅)₂]CH₃ |
| 787 (B17) | 2,5-diCl—C₆H₃ |

TABLE 13

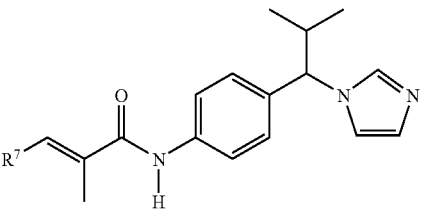

| Co No (Ex No) | R⁷; stereochemical descriptor if not racemic and/or addition salt |
|---|---|
| 574 (B2) | $CH_3$; (E) |
| 575 (B3) | 3-pyridinyl; (E) |
| 576 (B3) | 4-pyridinyl; (E) |
| 577 (B2) | 3-Cl—$C_6H_4$; (E) |
| 578 (B2) | 3-$CF_3$—$C_6H_4$ |
| 579 (B2) | 4-Cl—$C_6H_4$; (E) |
| 580 (B2) | 4-$CF_3$—$C_6H_4$; (E) |
| 581 (B2) | cyclohexyl; (E) |
| 582 (B2) | 4-$OCH_3$—$C_6H_4$; (E) |
| 583 (B2) | 4-F—$C_6H_4$; (E) |
| 584 (B2) | 3-$OCH_3$—$C_6H_4$; (E) |
| 585 (B2) | 2-F—$C_6H_4$; (E) |
| 586 (B2) | 3-F—$C_6H_4$; (E) |
| 587 (B2) | $(CH_2)_2C_6H_5$; (E) |
| 588 (B2) | $CH(CH_3)_2$; (E) |
| 589 (B2) | $CH_2C_6H_5$; (E) |
| 590 (B2) | 6-quinolinyl; (E) |
| 591 (B2) | 2-naphtalenyl; (E) |
| 592 (B2) | 4-quinolinyl; (E); hydrate (2:1) |
| 593 (B2) | 1-naphtalenyl; (E) |
| 594 (B2) | 2-furanyl; (E) |
| 595 (B2) | 2-thienyl; (E) |
| 596 (B2) | 3-thienyl; (E) |
| 597 (B3) | H |
| 598 (B2) | 2(1H)-quinolinone-6-yl; (E); hydrate (2:1) |
| 599 (B2) | 2-methyl-2H-benzotriazole-5-yl; (E) |
| 600 (B2) | 2-benzofuranyl; (E) |
| 601 (B2) | 5-methyl-2-furanyl; (E) |
| 602 (B2) | 1-methyl-1H-benzotriazole-6-yl; (E) |
| 603 (B2) | 2(1H)-quinolinone-4-yl; (E) |
| 604 (B3) | 2-pyridinyl; (E) |
| 605 (B3) | 1-methyl-2-pyrrolyl |
| 606 (B2) | 2,3,5,6-tetra(F)-4-($OC_2H_5$)phenyl; (E) |
| 607 (B2) | 2,4-di(F)—$C_6H_3$; (E) |
| 608 (B2) | 3-Br-4-F—$C_6H_3$; (E) |
| 609 (B2) | 2-F-4-$CF_3$—$C_6H_3$; (E) |
| 610 (B3) | 4-$NO_2$—$C_6H_4$; (E) |
| 611 (B16) | 4-$NH_2$—$C_6H_4$; (E) |
| 612 (B3) | 4-(NHC(=O)$CH_3$)—$C_6H_4$; (E) |

TABLE 14

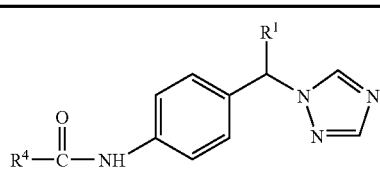

| Co No (Ex No) | R¹, R⁴; stereochemical descriptor if not racemic and/or addition salt |
|---|---|
| 613 (B1) | 3-$CF_3$—$C_6H_4$; $CH_3$ |
| 614 (B2) | 3-$CF_3$—$C_6H_4$; $CH_2C_6H_5$ |
| 615 (B1) | 3-F—$C_6H_4$; $CH_3$ |
| 616 (B1) | 3-F—$C_6H_4$; $CH_3$ |
| 617 (B2) | 3-$CF_3$—$C_6H_4$; CH=$CHC_6H_5$; (E) |
| 618 (B2) | 3-F—$C_6H_4$; CH=$CHC_6H_5$; (E) |
| 619 (B2) | 3-F—$C_6H_4$; $CH_2C_6H_5$ |
| 620 (B2) | 3-F—$C_6H_4$; $C(CH_3)$=$CHC_6H_5$; (E); nitrate (1:1) |

TABLE 14-continued

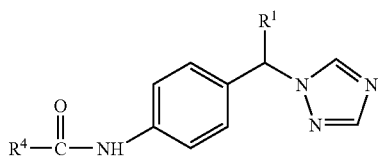

| Co No (Ex No) | R¹, R⁴; stereochemical descriptor if not racemic and/or addition salt |
|---|---|
| 621 (B2) | $CH(C_2H_5)_2$; 1,3-benzodioxolan-2-yl |
| 622 (B1) | $CH_2C(CH_3)_3$; $CH_3$ |
| 623 (B2) | $CH_2C(CH_3)_3$; $CH_2$(4-Cl—$C_6H_4$) |
| 624 (B2) | CH[C(=O)$OC_2H_5$]$CH_3$; $CH_2$(4-Cl—$C_6H_4$) |
| 625 (B1) | $CH(CH_3)C_2H_5$; $CH_3$ |
| 626 (B2) | $CH(CH_3)C_2H_5$; $CH_2$(4-Cl—$C_6H_4$) |
| 627 (B1) | $CH[N(CH_3)_2]CH_3$; $CH_3$; (A) |
| 628 (B2) | $CH[N(CH_3)_2]CH_3$; $CH_2$(4-Cl—$C_6H_4$); (A) |
| 629 (B3) | $CH[N(CH_3)_2]CH_3$; $(CH_2)_2$(3,4-di$OCH_3$—$C_6H_3$); (A) |
| 630 (B3) | $CH[N(CH_3)_2]CH_3$; $CH_2$(3,4,5-tri$OCH_3$—$C_6H_2$); (A) |
| 631 (B15) | $CH[N(CH_3)_2]CH_3$; $CH_3$; (B) |
| 632 (B2) | $CH[N(CH_3)_2]CH_3$; $C(CH_3)$=$CHC_6H_5$; [A-(E)] |
| 633 (B1) | $CH(CH_3)CH_2C_6H_5$; $CH_3$ |
| 634 (B2) | $CH(CH_3)CH_2C_6H_5$; $CH_2$(4-Cl—$C_6H_4$) |
| 635 (B15) | 1-(methyl-1-piperidinyl)ethyl; $CH_3$ |
| 636 (B2) | 1-(methyl-1-piperidinyl)ethyl; $CH_2$(4-Cl—$C_6H_4$) |
| 637 (B1) | $CH(CH_3)(n$-$C_3H_7)$; $CH_3$ |
| 638 (B2) | $CH(CH_3)(n$-$C_3H_7)$; $CH_2$(4-Cl—$C_6H_4$) |
| 639 (B3) | $CH(CH_3)(n$-$C_3H_7)$; $CH_2$(3,4-di$OCH_3$—$C_6H_3$) |
| 640 (B3) | $CH(CH_3)C_2H_5$; $CH_2$(3,4-di$OCH_3$—$C_6H_3$) |
| 641 (B1) | $C(CH_3)_3$; $CH_3$ |
| 642 (B3) | $C(CH_3)_3$; $CH_2$(3,4-di$OCH_3$—$C_6H_3$); hydrate (1;1) |
| 643 (B1) | $CH(n$-$C_3H_7)_2$; $CH_3$ |
| 644 (B2) | $CH(n$-$C_3H_7)_2$; $CH_2$(3,4-di$OCH_3$—$C_6H_3$) |
| 645 (B1) | $CH[N(CH_3)_2]C_2H_5$; $CH_3$; (A) |
| 646 (B3) | $CH[N(CH_3)_2]C_2H_5$; $CH_2$(3,4-di$OCH_3$—$C_6H_3$); (A) |
| 647 (B1) | $CH[N(C_2H_5)_2]CH_3$; $CH_3$; (A) |
| 648 (B1) | $CH[N(C_2H_5)_2]CH_3$; $CH_3$; (A + B) |
| 649 (B3) | $CH[N(C_2H_5)_2]CH_3$; $CH_2$(3,4-di$OCH_3$—$C_6H_3$); (A) |

TABLE 15

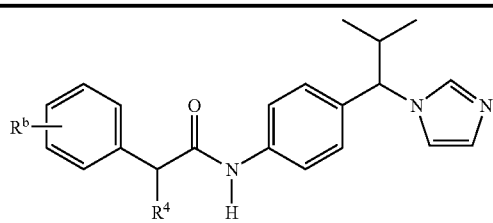

| Co No (Ex No) | R⁴, Rᵇ; stereochemical descriptor if not racemic and/or addition salt |
|---|---|
| 650 (B2) | H; H |
| 651 (B2) | H; 4-Cl |
| 652 (B2) | H; 3-Cl |
| 653 (B2) | H; 4-F |
| 654 (B2) | H; 3-$CF_3$ |
| 655 (B2) | $C_6H_5$; H |
| 656 (B2) | H; 3-F |

TABLE 15-continued

Structure: R^b-substituted phenyl-CH(R^4)-C(=O)-NH-phenyl-CH(CH(CH3)2)-N(imidazole)

| Co No (Ex No) | R^4, R^b; stereochemical descriptor if not racemic and/or addition salt |
|---|---|
| 657 (B2) | CH_3; H |
| 658 (B2) | CH(CH_3)_2; H |
| 659 (B2) | cyclopentyl; H |
| 660 (B2) | C_2H_5; H |
| 661 (B2) | cyclohexyl; H |
| 662 (B2) | H; 4-OCH_3 |
| 663 (B2) | H; 4-OC_2H_5 |
| 664 (B2) | H; 2-Cl |
| 665 (B2) | H; 3-OCH_3 |
| 666 (B2) | H; 4-CH_3 |
| 667 (B3) | H; 3-OH |
| 668 (B3) | H; 4-OH |
| 669 (B3) | OH; 4-Cl |
| 670 (B3) | OCH_3; H; [R-(R*, R*)] + [R-(R*, S*)] |

TABLE 16

Structure: R^4-C(=O)-NH-phenyl-CH(R^1)-pyridinyl

| Co No (Ex No) | pyridinyl position | R^1, R^4; stereochemical descriptor if not racemic and/or addition salt |
|---|---|---|
| 671 (B14) | 3 | CH(CH_3)_2; CH_3 |
| 672 (B2) | 3 | C_6H_5; CH=CH—C_6H_5 |
| 673 (B12) | 3 | 4-Cl—C_6H_4; CH_3 |
| 674 (B2) | 3 | 4-Cl—C_6H_4; CH=CH—C_6H_5 |
| 675 (B2) | 3 | C_6H_5; C(CH_3)=CH—C_6H_5 |
| 676 (B2) | 3 | 4-Cl—C_6H_4; CH=C(C_6H_5)_2 |
| 677 (B3) | 4 | 4-Cl—C_6H_4; CH=CC_6H_5)_2 |
| 678 (B2) | 3 | 3-F—C_6H_4; CH=CH—C_6H_5 |
| 679 (B2) | 3 | CH(CH_3)_2; C(CH_3)=CH—C_6H_5; (E) |
| 680 (B3) | 2 | 4-Cl—C_6H_4; CH=C(C_6H_5)_2 |
| 681 (B2) | 4 | CH(CH_3)_2; C(CH_3)=CH—C_6H_5; (E) |
| 682 (B2) | 2 | CH(CH_3)_2; C(CH_3)=CH—C_6H_5; (E) |
| 683 (B3) | 3 | 4-Cl—C_6H_4; CH=CH(3-Cl—C_6H_4)_2 |
| 684 (B3) | 3 | 4-Cl—C_6H_4; CH=C(C_6H_5)(3-Cl—C_6H_4) |
| 685 (B2) | 4 | CH(CH_3)_2; CH_2(4-Cl—C_6H_4) |
| 686 (B3) | 3 | CH(CH_3)_2; CH_2(4-Cl—C_6H_4) |
| 687 (B2) | 2 | CH(CH_3)_2; CH_2(4-Cl—C_6H_4) |
| 688 (B13) | 2 | OH; CH_3 |
| 689 (B13) | 3 | OH; CH_3 |
| 690 (B31) | 3 | CH(CH_3)_2; NH(3-F—C_6H_4) |
| 691 (B31) | 2 | CH(CH_3)_2; NH(3-F—C_6H_4) |
| 692 (B31) | 4 | CH(CH_3)_2; NH(3-F—C_6H_4) |
| 788 (B3) | 4 | H; CH=C(C_6H_5)(3-Cl—C_6H_4) |
| 789 (B3) | 4 | CH(CH_3)_2; CH=C(C_6H_5)(3-Cl—C_6H_4) |
| 790 (B3) | 4 | cyclohexyl; CH=C(C_6H_5)(3-Cl—C_6H_4) |

TABLE 17

Structure: R^4-C(=O)-NH-phenyl-CH(R^1)-N(imidazole with CH_3)

| Co No (Ex No) | methyl position | R^1, R^4; stereochemical descriptor if not racemic and/or addition salt |
|---|---|---|
| 693 (B2) | 5 | 4-Cl—C_6H_4; CH=C(C_6H_5)(3-Cl—C_6H_4); (E + Z) |
| 694 (B1) | 2 | CH(CH_3)_2; CH_3 |
| 695 (B2) | 2 | CH(CH_3)_2; CH_2(4-Cl—C_6H_4) |

TABLE 18

Structure: R^4-NH-C(=S)-NH-phenyl-CH(R^1)-N(imidazole with X)

| Co. No. | Ex. No. | R^1 | R^4 | X | Stereochemical descriptor if not racemic and/or addition salt |
|---|---|---|---|---|---|
| 696 | B31 | CH(CH_3)_2 | CH_3 | CH | |
| 697 | B31 | CH(CH_3)_2 | C_6H_5 | CH | |
| 698 | B25 | CH(CH_3)_2 | C_6H_5—C(=O)— | CH | |
| 699 | B22a B22b | CH(CH_3)_2 | H | CH | |

TABLE 18-continued

R⁴—NH—C(=S)—NH—C₆H₄—CH(R¹)—N(imidazole with X)

| Co. No. | Ex. No. | R¹ | R⁴ | X | Stereochemical descriptor if not racemic and/or addition salt |
|---|---|---|---|---|---|
| 700 | B31 | CH(CH₃)₂ | 2F—C₆H₄ | CH | |
| 701 | B31 | CH(CH₃)₂ | 3F—C₆H₄ | CH | |
| 702 | B25 | CH(C₂H₅)₂ | C₆H₅—C(=O)— | CH | |
| 703 | B22a | CH(C₂H₅)₂ | H | CH | |
| 704 | B27 | CH(CH₃)[N(CH₃)₂] | 2-benzothiazolyl | CH | (A) |
| 705 | B27 | CH(C₂H₅)₂ | 2-benzothiazolyl | CH | |
| 706 | B27 | CH(C₂H₅)₂ | 2-benzothiazolyl | N | |
| 791 | B25 | 2,5-diCl—C₆H₃ | C₆H₅—C(=O)— | CH | |
| 792 | B22a | 2,5-diCl—C₆H₃ | H | H | |

TABLE 19

(Rᵃ)ₙ—C₆H₄—NH—C(=O)—NH—C₆H₄—CH(R¹)—N(imidazole with X)

| Co. No. | Ex. No. | (Rᵃ)ₙ | R¹ | X | Stereochemical descriptor if not racemic |
|---|---|---|---|---|---|
| 707 | B31 | 4-(O—C₂H₅) | CH(CH₃)₂ | CH | |
| 708 | B23 | 3,4-di(OCH₃) | CH(CH₃)₂ | CH | |
| 709 | B31 | 2,5-di(F) | 3-(CF₃)—C₆H₄ | CH | |
| 710 | B31 | 2,5-di(F) | CH(C₂H₅)₂ | CH | |
| 711 | B31 | 3-F | 3-(CF₃)—C₆H₄ | N | |
| 712 | B31 | 2,5-di(F) | CH(C₂H₅)₂ | N | |
| 713 | B31 | 2-F | CH(C₂H₅)₂ | CH | |
| 714 | B31 | 2-F | 3-(CF₃)—C₆H₄ | CH | |
| 715 | B31 | 2-F | CH(C₂H₅)₂ | N | |
| 716 | B31 | 4-OCH₃ | 3-(CF₃)—C₆H₄ | CH | |
| 717 | B23 | 3,4-di(OCH₃) | CH(CH₃)[N(CH₃)₂] | N | (A) |
| 718 | B23 | 3,4-di(OCH₃) | CH(C₂H₅)₂ | N | |
| 719 | B23 | 3,4-di(OCH₃) | CH(CH₃)[N(CH₃)₂] | CH | (A) |
| 720 | B23 | 3,4-di(OCH₃) | CH(CH₃)[N(CH₃)₂] | N | (B) |
| 721 | B23 | 3,4-di(OCH₃) | CH₂—N(CH₃)₂ | CH | |
| 722 | B31 | 4-OCH₃ | CH(CH₃)₂ | CH | |
| 723 | B31 | 3-F | CH(C₂H₅)₂ | N | |
| 724 | B31 | 3-F | CH(C₂H₅)₂ | CH | |
| 725 | B31 | 3-F | CH(CH₃)₂ | N | |
| 726 | B31 | 2-F | CH(CH₃)₂ | CH | |
| 727 | B7 | 3-NH₂ | CH(CH₃)₂ | CH | |
| 728 | B31 | 2,5-di(F) | CH(CH₃)₂ | CH | |
| 729 | B31 | 3-F | 3-(CF₃)—C₆H₄ | CH | |
| 730 | B31 | 3-CF₃ | CH(CH₃)₂ | CH | |
| 731 | B31 | 3-F | 4-Cl—C₆H₄ | CH | |
| 732 | B31 | 3,4-di(Cl) | CH(CH₃)₂ | CH | |
| 733 | B31 | 3-OCH₃ | CH(CH₃)₂ | CH | |
| 734 | B31 | 2,4-di(F) | CH(CH₃)₂ | CH | |
| 735 | B31 | 3-F | C₆H₅ | CH | |
| 736 | B31 | 3-CH₃ | CH(CH₃)₂ | CH | |
| 737 | B31 | 3-NO₂ | CH(CH₃)₂ | CH | |
| 738 | B31 | 3-Cl | CH(CH₃)₂ | CH | |
| 739 | B31 | 4-Cl | CH(CH₃)₂ | CH | |
| 740 | B31 | 4-F | CH(CH₃)₂ | CH | |
| 741 | B31 | 3-F | CH(CH₃)₂ | CH | |
| 742 | B31 | H | CH(CH₃)₂ | CH | |

TABLE 20

-NH-C6H4-C(R1)(R2)-Het)

| Co. No. (Ex. No.) | R¹ | R² | R⁴ | X | Het | Stereochemical descriptor if not racemic |
|---|---|---|---|---|---|---|
| 743 (B29) | $CH(CH_3)_2$ | H | $NH_2$ | $N-C_6H_5$ | 1H-1-imidazolyl | |
| 744 (B29) | $CH(CH_3)_2$ | H | $NH_2$ | $N-(3F-C_6H_4)$ | 1H-1-imidazolyl | |
| 745 (B2) | $CH(CH_3)_2$ | $CH(CH_3)_2$ | $-CH_2-(4-Cl-C_6H_4)$ | O | 1,2,4-triazol-1-yl | |
| 746 (B31) | $CH(CH_3)_2$ | $CH(CH_3)_2$ | $-NH-(3-F-C_6H_4)$ | O | 1H-1-imidazolyl | |
| 747 (B1) | $CH(CH_3)_2$ | $CH(CH_3)_2$ | $CH_3$ | O | 1,2,4-triazol-1-yl | |
| 748 (B1) | $CH(CH_3)_2$ | H | $CH_3$ | O | 1,2,4-triazol-4-yl | |
| 749 (B2) | $CH(CH_3)_2$ | H | $-C(CH_3)=CH-C_6H_5$ | O | 1,2,4-triazol-4-yl | |
| 750 (B1) | $CH(CH_3)_2$ | $CH(CH_3)_2$ | $CH_3$ | O | 1H-1-imidazolyl | |
| 751 (B2) | $CH(CH_3)_2$ | $CH(CH_3)_2$ | $-C(CH_3)=CH-C_6H_5$ | O | 1H-1-imidazolyl | (E) |
| 752 (B17) | $CH_3$ | $CH_3$ | $CH_3$ | O | 1H-1-imidazolyl | |
| 753 (B2) | $CH_3$ | $CH_3$ | $-C(CH_3)=CH-C_6H_5$ | O | 1H-1-imidazolyl | |
| 754 (B1) | $CH(CH_3)_2$ | $C_2H_5$ | $CH_3$ | O | 1H-1-imidazolyl | |
| 755 (B2) | $CH(CH_3)_2$ | $C_2H_5$ | $(4-Cl-C_6H_4)-CH_2-$ | O | 1H-1-imidazolyl | |
| 756 (B1) | $C_2H_5$ | $C_2H_5$ | $CH_3$ | O | 1H-1-imidazolyl | |
| 757 (B1) | $CH(C_2H_5)_2$ | $CH(CH_3)_2$ | $CH_3$ | O | 1H-1-imidazolyl | |
| 758 (B2) | $CH(CH_3)_2$ | $C_2H_5$ | $-C(CH_3)=CH-C_6H_5$ | O | 1H-1-imidazolyl | (E) |
| 759 (B1) | $CH(CH_3)_2$ | $CH_3$ | $CH_3$ | O | 1H-1-imidazolyl | |
| 760 (B1) | $CH(CH_3)_2$ | $n-C_4H_9$ | $CH_3$ | O | 1H-1-imidazolyl | |
| 761 (B2) | $CH(CH_3)_2$ | $n-C_4H_9$ | $-C(CH_3)=CH-C_6H_5$ | O | 1H-1-imidazolyl | (E) |
| 762 (B2) | $CH(CH_3)_2$ | $CH(CH_3)_2$ | $CH_2-[3,4-di-(OCH_3)-C_6H_3]$ | O | 1H-1-imidazolyl | |
| 763 (B2) | $CH(CH_3)_2$ | $CH(CH_3)_2$ | $-CH_2-(4-Cl-C_6H_4)$ | O | 1H-1-imidazolyl | |
| 764 (B28) | $CH(CH_3)_2$ | H | $-CH_2-(4-Cl-C_6H_4)$ | S | 1H-1-imidazolyl | |
| 765 (B9) | $CH(C_2H_5)_2$ | $n-C_3H_7$ | $CH_3$ | O | 1H-1-imidazolyl | |
| 766 (B2) | $CH(C_2H_5)_2$ | $n-C_3H_7$ | $-CH_2-(4-Cl-C_6H_4)$ | O | 1H-1-imidazolyl | |
| 767 (B1) | $CH(C_2H_5)_2$ | $C_2H_5$ | $CH_3$ | O | 1H-1-imidazolyl | |
| 768 (B2) | $CH(C_2H_5)_2$ | $C_2H_5$ | $-CH_2-(4-Cl-C_6H_4)$ | O | 1H-1-imidazolyl | |
| 769 (B25) | OH | H | $CH_3$ | O | 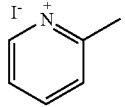 | |
| 770 (B25) | OH | H | $CH_3$ | O | 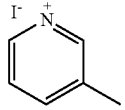 | |
| 771 (B24) | OH | $CH(CH_3)-N(CH_3)_2$ | $CH_3$ | O | 1-methyl-5-imidazolyl | |
| 772 (B24) | OH | $CH(C_2H_5)_2$ | $CH_3$ | O | 1-methyl-5-imidazolyl | |
| 773 (B31) | $CH(CH_3)_2$ | H | $-NH-(3-F-C_6H_4)$ | O | 2-methyl-1-imidazolyl | |
| 793 (B33) | $4-Cl-C_6H_4$ | H | H | O | 1-methyl-5-imidazolyl | |
| 794 (B3) | $4-Cl-C_6H_4$ | OH | $CH(OH)(3-Cl-C_6H_4)$ | O | 1-methyl-5-imidazolyl | |
| 795 (B3) | $4-Cl-C_6H_4$ | H | $CH(OH)(3-Cl-C_6H_4)$ | O | 1-methyl-5-imidazolyl | |
| 796 (32) | $2,5-diCl-C_6H_3$ | H | $-S-CH_3$ | NH | 1H-1-imidazolyl | |
| 797 (B29) | $2,5-diCl-C_6H_3$ | H | $-NH-CH_3$ | NH | 1H-1-imidazolyl | HCl (1:2) |

TABLE 20

R⁴—C(=O)—NH—C₆H₄—C(H₂C—(CH₂)ₙ)(imidazole)

| Co.No. (Ex.No.) | R⁴ | n |
|---|---|---|
| 774 (B17) | —CH₂—(4-Cl—C₆H₄) | 3 |
| 775 (B17) | CH₃ | 3 |
| 776 (B17) | CH₃ | 4 |

Table 21 lists the experimental analysis values for carbon, hydrogen and nitrogen of some of the compounds as prepared in the experimental part hereinabove.

TABLE 21

| Comp No. | C | H | N |
|---|---|---|---|
| 17 | 64.0 | 6.2 | 12.7 |
| 18 | 63.8 | 6.3 | 13.0 |
| 20 | 63.5 | 6.7 | 12.8 |
| 21 | 64.2 | 6.6 | 12.8 |
| 30 | 72.3 | 8.3 | 8.4 |
| 52 | 72.0 | 8.1 | 9.3 |
| 53 | 68.7 | 8.6 | 12.2 |
| 61 | 74.2 | 8.2 | 10.0 |
| 64 | 65.9 | 5.8 | 16.3 |
| 85 | 70.8 | 7.7 | 13.8 |
| 86 | 70.7 | 7.8 | 13.9 |
| 87 | 69.6 | 6.7 | 10.6 |
| 119 | 71.3 | 7.5 | 10.0 |
| 120 | 75.1 | 7.0 | 8.4 |
| 121 | 74.4 | 6.9 | 11.9 |
| 122 | 73.9 | 7.9 | 10.2 |
| 123 | 74.0 | 7.9 | 10.3 |
| 125 | 74.3 | 8.1 | 10.0 |
| 131 | 64.7 | 5.7 | 15.2 |
| 142 | 69.6 | 6.8 | 11.0 |
| 143 | 62.7 | 5.2 | 10.3 |
| 145 | 71.4 | 7.0 | 15.2 |
| 147 | 72.1 | 7.0 | 15.4 |
| 148 | 52.6 | 5.0 | 11.5 |
| 152 | 72.3 | 7.2 | 16.0 |
| 154 | 73.5 | 6.8 | 15.7 |
| 162 | 66.9 | 5.9 | 14.0 |
| 163 | 70.2 | 7.8 | 15.3 |
| 164 | 76.9 | 7.6 | 11.6 |
| 194 | 71.0 | 6.4 | 17.5 |
| 237 | 70.6 | 6.5 | 10.7 |
| 247 | 71.7 | 6.6 | 16.6 |
| 248 | 69.4 | 5.6 | 11.5 |
| 259 | 50.5 | 4.3 | 16.5 |
| 260 | 50.6 | 4.4 | 16.6 |
| 298 | 60.1 | 6.0 | 16.5 |
| 299 | 60.7 | 6.0 | 16.5 |
| 318 | 68.2 | 7.3 | 13.5 |
| 343 | 68.9 | 6.5 | 14.8 |
| 348 | 69.6 | 7.5 | 12.7 |
| 349 | 65.1 | 8.2 | 22.5 |
| 360 | 69.3 | 6.6 | 10.5 |
| 367 | 67.0 | 6.2 | 14.3 |
| 368 | 65.1 | 6.2 | 13.8 |
| 369 | 67.5 | 5.1 | 8.9 |
| 376 | 62.7 | 4.5 | 8.3 |
| 383 | 69.4 | 7.6 | 12.1 |
| 389 | 69.5 | 7.5 | 11.0 |
| 391 | 67.2 | 7.1 | 11.7 |
| 392 | 68.3 | 7.4 | 12.7 |
| 394 | 64.8 | 6.2 | 9.0 |
| 397 | 66.2 | 6.3 | 10.3 |
| 402 | 64.6 | 6.5 | 9.6 |
| 404 | 67.9 | 6.9 | 9.8 |
| 405 | 67.9 | 7.0 | 9.7 |
| 410 | 66.9 | 7.2 | 11.8 |
| 411 | 69.8 | 7.1 | 12.1 |
| 414 | 68.9 | 7.6 | 12.1 |
| 415 | 71.6 | 7.2 | 10.8 |
| 417 | 71.2 | 6.0 | 9.0 |
| 419 | 75.1 | 6.4 | 9.5 |
| 420 | 75.2 | 5.5 | 11.0 |
| 425 | 72.9 | 5.1 | 10.2 |
| 426 | 72.9 | 5.5 | 9.6 |
| 438 | 65.5 | 7.2 | 16.1 |
| 445 | 79.6 | 5.9 | 10.7 |
| 454 | 79.9 | 6.3 | 10.0 |
| 455 | 77.0 | 7.0 | 11.7 |
| 456 | 79.5 | 6.7 | 9.5 |
| 457 | 77.3 | 7.4 | 11.2 |
| 458 | 76.5 | 7.1 | 11.5 |
| 459 | 76.3 | 7.1 | 11.5 |
| 460 | 75.4 | 6.6 | 12.0 |
| 461 | 72.0 | 6.0 | 11.3 |
| 462 | 77.0 | 7.3 | 11.2 |
| 463 | 78.1 | 7.4 | 10.4 |
| 464 | 77.1 | 7.6 | 10.7 |
| 465 | 77.5 | 7.8 | 10.4 |
| 466 | 75.6 | 6.3 | 12.6 |
| 467 | 76.9 | 7.0 | 11.7 |
| 468 | 80.8 | 6.8 | 9.0 |
| 469 | 77.4 | 6.5 | 11.7 |
| 470 | 77.8 | 7.1 | 10.8 |
| 471 | 77.6 | 7.7 | 10.9 |
| 472 | 78.2 | 7.5 | 10.1 |
| 482 | 77.2 | 7.6 | 10.8 |
| 483 | 73.5 | 6.0 | 9.1 |
| 484 | 73.7 | 6.2 | 9.1 |
| 485 | 81.8 | 5.9 | 8.6 |
| 497 | 78.7 | 5.6 | 10.8 |
| 502 | 75.9 | 6.6 | 12.0 |
| 511 | 79.7 | 6.4 | 9.9 |
| 512 | 72.8 | 5.2 | 9.6 |
| 513 | 74.8 | 6.2 | 8.9 |
| 514 | 75.2 | 6.2 | 8.4 |
| 515 | 73.7 | 5.8 | 9.1 |
| 521 | 69.9 | 7.4 | 16.3 |
| 523 | 70.0 | 5.2 | 13.6 |
| 524 | 63.4 | 4.5 | 11.7 |
| 566 | 67.6 | 8.1 | 18.6 |
| 572 | 76.2 | 7.1 | 12.7 |
| 574 | 71.4 | 7.7 | 14.0 |
| 575 | 73.3 | 6.8 | 15.6 |
| 576 | 73.2 | 6.7 | 15.6 |
| 577 | 69.5 | 6.0 | 10.6 |
| 578 | 67.3 | 5.6 | 9.8 |
| 579 | 69.7 | 6.1 | 10.5 |
| 580 | 67.4 | 5.6 | 9.8 |
| 581 | 75.6 | 8.6 | 11.4 |
| 582 | 73.7 | 7.0 | 10.7 |
| 583 | 73.3 | 6.4 | 11.1 |
| 584 | 73.4 | 7.0 | 10.5 |
| 585 | 72.9 | 6.4 | 11.1 |
| 586 | 72.9 | 6.4 | 11.1 |
| 587 | 76.4 | 7.5 | 10.6 |
| 588 | 74.1 | 8.6 | 13.2 |
| 589 | 77.2 | 7.4 | 11.2 |
| 602 | 68.6 | 6.2 | 19.8 |
| 612 | 71.9 | 6.8 | 13.5 |
| 613 | 59.8 | 4.2 | 15.3 |
| 614 | 65.9 | 4.4 | 12.7 |
| 615 | 65.8 | 4.9 | 18.2 |
| 616 | 65.7 | 4.7 | 18.2 |
| 617 | 66.9 | 4.1 | 12.4 |
| 618 | 72.1 | 4.7 | 14.0 |
| 619 | 71.3 | 4.9 | 14.6 |
| 620 | 64.5 | 4.7 | 14.2 |
| 636 | 66.0 | 6.6 | 14.9 |
| 644 | 67.4 | 7.3 | 11.5 |
| 650 | 75.1 | 6.8 | 12.5 |
| 666 | 76.1 | 7.4 | 11.9 |
| 667 | 71.9 | 6.5 | 11.9 |

TABLE 21-continued

| Comp No. | C | H | N |
|---|---|---|---|
| 676 | 79.3 | 5.1 | 5.5 |
| 677 | 79.8 | 5.1 | 5.5 |
| 679 | 80.8 | 7.0 | 7.4 |
| 680 | 78.9 | 5.0 | 5.6 |
| 681 | 81.4 | 7.2 | 7.5 |
| 682 | 80.8 | 7.1 | 7.5 |
| 695 | 68.0 | 6.2 | 10.7 |
| 704 | 60.3 | 5.7 | 18.7 |
| 705 | 63.3 | 6.2 | 15.7 |
| 706 | 60.5 | 5.4 | 19.2 |
| 720 | 61.5 | 6.6 | 19.3 |
| 734 | 64.8 | 5.4 | 15.2 |
| 749 | 73.4 | 6.7 | 15.6 |
| 771 | 63.9 | 7.7 | 17.2 |
| 777 | 65.1 | 5.6 | 17.2 |
| 782 | 70.6 | 7.7 | 13.9 |
| 783 | 70.5 | 7.7 | 13.8 |
| 786 | 67.0 | 4.5 | 8.9 |
| 788 | 76.0 | 4.9 | 6.5 |
| 789 | 76.9 | 5.8 | 5.9 |
| 793 | 66.1 | 4.9 | 12.7 |
| 794 | 61.8 | 4.4 | 8.4 |
| 795 | 63.5 | 4.6 | 8.6 |
| 797 | 46.9 | 4.6 | 14.5 |

C. PHARMACOLOGICAL EXAMPLES

Example C.1

Inhibition of Retinoic Acid (RA) Metabolism

MCF-7 human breast cancer cells were grown as stock cultures according to art-known protocols. One day before the experiment, RA is added to the stock cultures to stimulate RA-metabolism. At the start of the experiment, cell suspensions were incubated in a tissue culture medium containing $^3$H-RA as the substrate. Different concentrations of the test compound (dissolved in 1% DMSO) were added to the incubation mixtures, and at the end of the incubation, the unmetabolized RA is separated from its polar metabolites. The fraction containing the polar $^3$H-labelled metabolites was collected and counted in a scintillation counter. For each experiment, a control and a blank incubation were run in parallel. Table 22 list the $IC_{50}$ value (defined as the concentration in M needed to reduce the amount of metabolites to 50% of the control).

TABLE 22

| Co. No. | $IC_{50}$ (in M) |
|---|---|
| 1 | 1.38E−10 |
| 2 | 3.00E−11 |
| 4 | 2.11E−09 |
| 5 | 2.70E−10 |
| 6 | 1.65E−09 |
| 7 | 7.90E−10 |
| 8 | 9.37E−11 |
| 10 | 1.55E−09 |
| 11 | 2.63E−09 |
| 12 | 3.65E−11 |
| 13 | 3.57E−11 |
| 17 | 9.99E−10 |
| 18 | 8.72E−10 |
| 21 | 2.89E−09 |
| 22 | 1.04E−09 |
| 23 | 5.03E−10 |
| 24 | 1.37E−09 |
| 25 | 6.10E−08 |
| 26 | 2.01E−10 |

TABLE 22-continued

| Co. No. | $IC_{50}$ (in M) |
|---|---|
| 27 | 2.32E−10 |
| 28 | 2.76E−09 |
| 29 | 8.12E−09 |
| 30 | 2.58E−08 |
| 31 | 2.63E−09 |
| 32 | 6.97E−10 |
| 33 | 1.01E−09 |
| 34 | 1.03E−09 |
| 35 | 2.24E−09 |
| 36 | 1.43E−09 |
| 37 | 1.00E−09 |
| 38 | 1.04E−09 |
| 39 | 1.04E−10 |
| 41 | 1.98E−09 |
| 45 | 1.72E−10 |
| 46 | 1.95E−09 |
| 47 | 1.33E−09 |
| 48 | 5.69E−10 |
| 49 | 4.33E−10 |
| 50 | 7.44E−09 |
| 51 | 8.95E−10 |
| 52 | 9.07E−10 |
| 53 | 2.12E−09 |
| 54 | 4.86E−09 |
| 56 | 2.51E−11 |
| 58 | <1.00E−11 |
| 61 | 7.34E−10 |
| 63 | 6.70E−09 |
| 64 | 6.60E−09 |
| 65 | 3.79E−10 |
| 66 | 3.56E−10 |
| 67 | 3.34E−10 |
| 68 | 1.72E−09 |
| 69 | 2.50E−10 |
| 70 | 2.95E−10 |
| 71 | 2.62E−10 |
| 72 | 1.66E−09 |
| 73 | 4.63E−10 |
| 75 | 4.17E−10 |
| 76 | 5.88E−10 |
| 77 | 3.32E−10 |
| 78 | 2.27E−10 |
| 79 | 3.42E−11 |
| 80 | 4.83E−11 |
| 81 | 2.31E−10 |
| 82 | 1.16E−09 |
| 83 | 1.62E−10 |
| 84 | 1.74E−09 |
| 85 | 3.92E−09 |
| 86 | 4.97E−10 |
| 87 | 2.80E−10 |
| 88 | 1.48E−10 |
| 89 | 1.31E−10 |
| 90 | 2.36E−09 |
| 91 | 9.35E−10 |
| 92 | 2.21E−09 |
| 93 | 1.59E−09 |
| 94 | 1.06E−09 |
| 95 | 1.48E−09 |
| 96 | 1.09E−09 |
| 97 | 1.32E−09 |
| 98 | 1.64E−09 |
| 99 | 5.77E−09 |
| 102 | 6.78E−11 |
| 103 | 7.11E−09 |
| 104 | 4.07E−11 |
| 105 | 5.16E−11 |
| 106 | 1.69E−09 |
| 107 | 1.44E−09 |
| 108 | 2.34E−11 |
| 109 | 3.21E−10 |
| 110 | 9.53E−10 |
| 111 | 1.03E−09 |
| 112 | 9.89E−10 |
| 113 | 8.52E−10 |
| 115 | 8.17E−09 |
| 116 | 6.78E−10 |

TABLE 22-continued

| Co. No. | IC$_{50}$ (in M) |
|---|---|
| 117 | 2.55E−10 |
| 118 | 2.24E−09 |
| 119 | 9.40E−10 |
| 120 | 3.88E−09 |
| 121 | 9.14E−10 |
| 122 | 2.40E−09 |
| 123 | 2.47E−11 |
| 124 | 3.97E−11 |
| 125 | 1.94E−10 |
| 126 | <1.00E−11 |
| 127 | 2.85E−11 |
| 128 | 1.81E−11 |
| 129 | 2.36E−11 |
| 130 | 1.09E−11 |
| 131 | 4.10E−09 |
| 132 | 4.49E−09 |
| 133 | 4.56E−09 |
| 134 | 2.98E−09 |
| 135 | 1.43E−09 |
| 136 | 4.83E−09 |
| 137 | 1.85E−09 |
| 138 | 6.38E−09 |
| 139 | 1.75E−09 |
| 140 | 2.15E−08 |
| 141 | 1.31E−09 |
| 142 | 3.11E−08 |
| 143 | 4.08E−09 |
| 145 | 3.03E−09 |
| 147 | 3.30E−08 |
| 148 | 1.86E−09 |
| 151 | 2.11E−09 |
| 152 | 5.18E−09 |
| 154 | 4.14E−09 |
| 155 | 5.01E−08 |
| 156 | 3.10E−08 |
| 157 | 8.48E−08 |
| 158 | >1.00E−07 |
| 159 | >1.00E−07 |
| 160 | 8.65E−08 |
| 161 | 1.87E−09 |
| 162 | 2.88E−09 |
| 163 | 2.36E−09 |
| 164 | 8.15E−09 |
| 165 | 1.08E−08 |
| 166 | 1.75E−09 |
| 167 | 4.16E−09 |
| 168 | 2.36E−09 |
| 169 | 5.31E−10 |
| 170 | 1.22E−08 |
| 171 | 8.58E−08 |
| 172 | 3.41E−09 |
| 173 | 5.17E−09 |
| 174 | 1.60E−09 |
| 175 | 4.83E−09 |
| 176 | 1.87E−08 |
| 179 | 3.69E−08 |
| 180 | 5.69E−08 |
| 181 | 1.41E−08 |
| 182 | 1.31E−08 |
| 183 | 7.40E−09 |
| 184 | 5.15E−09 |
| 185 | 3.97E−08 |
| 186 | >1.00E−07 |
| 187 | 1.88E−08 |
| 189 | >1.00E−07 |
| 190 | >1.00E−07 |
| 191 | >1.00E−07 |
| 192 | 3.34E−09 |
| 193 | 1.21E−08 |
| 194 | 7.07E−09 |
| 195 | 3.51E−08 |
| 196 | 2.23E−08 |
| 197 | 5.61E−09 |
| 198 | 1.07E−08 |
| 199 | 7.82E−09 |
| 200 | 4.43E−08 |
| 201 | 3.58E−09 |

TABLE 22-continued

| Co. No. | IC$_{50}$ (in M) |
|---|---|
| 202 | 1.84E−09 |
| 203 | 2.28E−08 |
| 204 | 4.58E−09 |
| 205 | 1.17E−08 |
| 207 | 2.54E−08 |
| 208 | 6.43E−08 |
| 209 | 8.27E−09 |
| 210 | 2.90E−08 |
| 212 | 4.07E−09 |
| 213 | 2.07E−09 |
| 214 | 3.37E−09 |
| 215 | 3.60E−08 |
| 216 | 1.17E−08 |
| 217 | 5.14E−09 |
| 219 | 3.20E−09 |
| 220 | 1.48E−09 |
| 221 | 1.08E−09 |
| 222 | 3.32E−09 |
| 223 | 1.20E−09 |
| 224 | 4.73E−09 |
| 225 | 8.28E−08 |
| 226 | 1.69E−08 |
| 227 | 7.80E−09 |
| 228 | 7.30E−08 |
| 229 | 1.64E−09 |
| 230 | 3.89E−09 |
| 231 | 1.86E−09 |
| 232 | 1.51E−09 |
| 233 | 2.43E−09 |
| 234 | 3.01E−09 |
| 235 | 6.94E−09 |
| 236 | 9.84E−08 |
| 237 | 1.82E−08 |
| 238 | >1.00E−07 |
| 239 | 7.28E−10 |
| 240 | 1.34E−09 |
| 241 | 2.59E−09 |
| 242 | 2.82E−09 |
| 243 | 3.59E−08 |
| 244 | 2.30E−09 |
| 245 | 2.79E−09 |
| 246 | 2.10E−09 |
| 247 | 3.55E−08 |
| 248 | 1.79E−09 |
| 249 | 7.58E−08 |
| 250 | 1.49E−08 |
| 251 | 3.93E−09 |
| 252 | 2.59E−09 |
| 253 | 5.55E−09 |
| 254 | 6.47E−09 |
| 255 | 6.24E−09 |
| 256 | 3.20E−09 |
| 259 | 9.29E−09 |
| 260 | 2.43E−09 |
| 261 | 2.22E−09 |
| 262 | 7.48E−09 |
| 263 | 4.66E−09 |
| 264 | 2.71E−09 |
| 266 | 3.11E−08 |
| 267 | 7.75E−09 |
| 268 | 7.79E−09 |
| 269 | 2.66E−09 |
| 270 | 5.61E−09 |
| 271 | 2.45E−09 |
| 272 | 4.81E−09 |
| 273 | 5.27E−08 |
| 274 | 6.64E−09 |
| 275 | 4.28E−09 |
| 276 | 1.60E−08 |
| 277 | 1.17E−09 |
| 288 | 1.28E−09 |
| 289 | 5.07E−10 |
| 290 | 1.14E−09 |
| 291 | 4.23E−09 |
| 292 | 1.37E−10 |
| 293 | 6.53E−09 |
| 297 | 7.86E−10 |

TABLE 22-continued

| Co. No. | IC$_{50}$ (in M) |
|---|---|
| 299 | 7.72E−10 |
| 301 | 6.05E−09 |
| 303 | 3.26E−09 |
| 305 | 8.29E−11 |
| 306 | 1.26E−09 |
| 307 | 7.01E−10 |
| 309 | 3.65E−09 |
| 311 | 6.64E−10 |
| 313 | 2.00E−11 |
| 316 | 4.06E−09 |
| 330 | 1.82E−09 |
| 332 | 1.50E−09 |
| 336 | 1.91E−09 |
| 339 | 1.23E−09 |
| 346 | 2.04E−09 |
| 351 | 5.69E−09 |
| 352 | 2.57E−10 |
| 353 | 1.97E−09 |
| 355 | >1.00E−07 |
| 356 | >1.00E−07 |
| 357 | >1.00E−07 |
| 358 | >1.00E−07 |
| 359 | 6.25E−09 |
| 360 | 1.08E−09 |
| 361 | >1.00E−07 |
| 362 | 1.43E−08 |
| 363 | 1.42E−09 |
| 364 | 1.41E−09 |
| 365 | 1.08E−09 |
| 366 | 3.05E−09 |
| 367 | 1.25E−09 |
| 368 | 5.83E−10 |
| 369 | 8.22E−08 |
| 370 | 8.34E−08 |
| 371 | 3.59E−09 |
| 372 | 1.97E−09 |
| 376 | <1.00E−10 |
| 378 | 1.74E−09 |
| 383 | 7.29E−10 |
| 385 | 6.75E−09 |
| 388 | 8.29E−10 |
| 389 | 5.67E−11 |
| 393 | 9.55E−10 |
| 404 | 1.35E−09 |
| 405 | 3.68E−09 |
| 412 | 3.99E−09 |
| 413 | 5.27E−09 |
| 415 | 2.64E−09 |
| 416 | 3.67E−10 |
| 420 | 8.38E−08 |
| 421 | >1.00E−07 |
| 422 | >1.00E−08 |
| 423 | 4.08E−08 |
| 424 | >1.00E−07 |
| 425 | 3.81E−08 |
| 426 | >1.00E−07 |
| 427 | 8.34E−09 |
| 432 | 8.10E−10 |
| 435 | 2.80E−09 |
| 445 | 1.92E−07 |
| 454 | 5.25E−08 |
| 455 | 2.87E−09 |
| 456 | 1.40E−07 |
| 457 | 2.50E−08 |
| 458 | 3.22E−09 |
| 459 | 1.77E−08 |
| 460 | 3.63E−08 |
| 461 | 1.69E−08 |
| 462 | >1.00E−06 |
| 463 | 2.45E−08 |
| 464 | 1.49E−07 |
| 465 | 5.04E−08 |
| 466 | >1.00E−06 |
| 467 | 2.58E−09 |
| 468 | >1.00E−07 |
| 469 | >1.00E−07 |
| 470 | 1.87E−08 |
| 471 | >1.00E−07 |
| 472 | 9.51E−08 |
| 473 | >1.00E−07 |
| 474 | 1.59E−08 |
| 475 | >1.00E−07 |
| 476 | 3.55E−08 |
| 477 | >1.00E−06 |
| 478 | 1.63E−09 |
| 479 | >1.00E−07 |
| 480 | 4.25E−09 |
| 481 | 2.83E−09 |
| 482 | 1.95E−09 |
| 483 | 1.98E−08 |
| 484 | 3.43E−09 |
| 485 | >1.00E−07 |
| 486 | 2.77E−08 |
| 488 | >1.00E−07 |
| 489 | >1.00E−07 |
| 490 | >1.00E−07 |
| 491 | 1.84E−09 |
| 492 | 4.07E−09 |
| 493 | 8.77E−09 |
| 497 | 3.76E−08 |
| 502 | 3.29E−08 |
| 511 | 1.05E−08 |
| 512 | 6.16E−07 |
| 513 | 8.60E−07 |
| 514 | >1.00E−06 |
| 515 | >1.00E−06 |
| 516 | >1.00E−06 |
| 517 | 3.69E−08 |
| 518 | >1.00E−07 |
| 519 | 3.80E−09 |
| 524 | >1.00E−06 |
| 558 | 1.32E−09 |
| 574 | 1.78E−09 |
| 575 | 2.57E−08 |
| 576 | 2.01E−08 |
| 577 | 4.23E−08 |
| 578 | 7.67E−09 |
| 579 | 1.24E−08 |
| 580 | 3.13E−08 |
| 581 | >1.00E−07 |
| 582 | 1.58E−09 |
| 583 | 2.78E−09 |
| 584 | 6.51E−09 |
| 585 | 7.21E−09 |
| 586 | 3.74E−09 |
| 587 | 3.16E−08 |
| 588 | 4.88E−08 |
| 589 | 2.75E−09 |
| 590 | 2.78E−09 |
| 591 | 4.01E−08 |
| 592 | 4.15E−09 |
| 593 | 2.70E−09 |
| 594 | 4.81E−09 |
| 595 | 3.83E−09 |
| 596 | 7.92E−09 |
| 597 | 5.00E−09 |
| 598 | 2.39E−08 |
| 599 | 6.36E−09 |
| 600 | 3.67E−08 |
| 601 | 2.00E−08 |
| 602 | 2.57E−08 |
| 603 | >1.00E−07 |
| 604 | 2.89E−09 |
| 605 | 1.40E−08 |
| 606 | 1.36E−08 |
| 608 | 6.61E−09 |
| 609 | 1.09E−08 |
| 610 | 6.53E−09 |
| 611 | 3.42E−09 |
| 612 | 1.68E−08 |
| 613 | 1.80E−06 |
| 614 | 2.78E−07 |
| 615 | >1.00E−06 |
| 616 | >1.00E−06 |

TABLE 22-continued

| Co. No. | IC$_{50}$ (in M) |
|---|---|
| 617 | 1.51E−07 |
| 618 | 1.57E−08 |
| 619 | 3.57E−08 |
| 620 | >1.00E−06 |
| 621 | 1.25E−09 |
| 623 | 1.38E−09 |
| 639 | 1.68E−09 |
| 640 | 2.17E−09 |
| 642 | 1.16E−09 |
| 644 | 2.96E−10 |
| 645 | 8.02E−09 |
| 646 | 3.07E−09 |
| 649 | 7.32E−09 |
| 650 | 4.86E−09 |
| 651 | 1.05E−08 |
| 652 | >1.00E−07 |
| 653 | 1.34E−09 |
| 654 | 2.34E−09 |
| 655 | 1.61E−08 |
| 656 | 1.47E−09 |
| 657 | 5.36E−09 |
| 658 | 5.48E−09 |
| 659 | >1.00E−07 |
| 660 | 6.37E−09 |
| 661 | 3.40E−08 |
| 662 | 3.58E−10 |
| 663 | 1.95E−09 |
| 664 | 1.56E−09 |
| 665 | 5.91E−09 |
| 666 | 1.45E−08 |
| 667 | 1.57E−09 |
| 668 | 3.16E−09 |
| 669 | 8.66E−09 |
| 670 | 5.72E−09 |
| 679 | >1.00E−06 |
| 680 | 1.21E−08 |
| 681 | >1.00E−06 |
| 682 | >1.00E−07 |
| 685 | 9.08E−08 |
| 686 | 4.31E−08 |
| 687 | >1.00E−07 |
| 690 | >1.00E−07 |
| 691 | >1.00E−07 |
| 692 | 3.80E−08 |
| 693 | >1.00E−07 |
| 695 | >1.00E−07 |
| 696 | 8.07E−09 |
| 697 | 1.71E−08 |
| 698 | 3.96E−08 |
| 699 | 9.69E−09 |
| 700 | 1.20E−08 |
| 707 | 1.30E−08 |
| 708 | 1.61E−09 |
| 709 | 2.40E−09 |
| 710 | 1.88E−10 |
| 711 | >1.00E−07 |
| 712 | 4.30E−12 |
| 713 | 1.38E−09 |
| 715 | 1.54E−10 |
| 718 | 1.33E−10 |
| 722 | 4.14E−09 |
| 723 | 1.13E−09 |
| 724 | 1.18E−09 |
| 725 | 3.29E−09 |
| 726 | 3.71E−09 |
| 727 | 1.64E−09 |
| 728 | 1.41E−09 |
| 729 | >1.00E−07 |
| 730 | 1.59E−08 |
| 731 | >1.00E−07 |
| 732 | 1.93E−08 |
| 733 | 2.41E−09 |
| 734 | 2.25E−09 |
| 735 | >1.00E−07 |
| 736 | 7.45E−09 |
| 737 | 2.36E−09 |
| 738 | 2.03E−09 |

TABLE 22-continued

| Co. No. | IC$_{50}$ (in M) |
|---|---|
| 739 | 4.21E−08 |
| 740 | 1.29E−09 |
| 741 | 1.44E−09 |
| 742 | 2.61E−10 |
| 743 | 1.10E−08 |
| 744 | >1.00E−07 |
| 745 | 3.87E−09 |
| 746 | >1.00E−07 |
| 749 | 1.26E−07 |
| 751 | 6.70E−08 |
| 753 | >1.00E−07 |
| 755 | 4.35E−09 |
| 758 | 1.88E−09 |
| 761 | >1.00E−07 |
| 762 | 4.08E−08 |
| 763 | 5.62E−09 |
| 764 | 2.33E−08 |
| 772 | 1.46E−10 |
| 773 | >1.00E−07 |
| 774 | 5.27E−09 |
| 776 | 4.39E−09 |
| 778 | 7.59E−08 |
| 780 | 4.57E−09 |
| 781 | 3.24E−09 |
| 782 | 1.26E−09 |
| 783 | 3.98E−08 |

Example C.2

"Vaginal Keratinization Test on Ovariectomized Rats"

Ovariectomized rats were injected subcutaneously with a sesame oil solution containing 100 μg of estradiol undecylate in a volume of 0.1 ml per 100 g body weight and control animals were injected with sesame oil. On day one, two and three, test animals were treated once daily with a per os dose of the test compound and control animals with the drug vehicle (PEG 200). One day after the last treatment, the animals were sacrificed and their vaginas were processed for histological evaluation according to the method described in J. Pharmacol. Exp. Ther. 261(2), 773–779 (1992). A dose at which 50% of the tested rats show complete suppression of the estradiol undecylate induced keratinization effects is defined as an active dose. Table 23 lists the lowest active dose (LAD in mg/kg) of the compounds of formula (I) which were tested.

TABLE 23

| Co. No. | LAD (mg/kg) |
|---|---|
| 2 | 5.00 |
| 3 | >2.50 |
| 4 | 0.60 |
| 5 | >2.50 |
| 6 | 2.50 |
| 7 | >2.50 |
| 8 | >2.50 |
| 10 | 2.50 |
| 11 | >2.50 |
| 13 | >2.50 |
| 15 | >2.50 |
| 18 | 2.50 |
| 20 | 2.50 |
| 21 | 5.00 |
| 22 | 2.50 |
| 23 | 2.50 |
| 24 | 2.50 |
| 25 | 10.00 |
| 26 | 5.00 |

TABLE 23-continued

| Co. No. | LAD (mg/kg) |
|---|---|
| 27 | 5.00 |
| 28 | 2.50 |
| 29 | 5.00 |
| 30 | >5.00 |
| 31 | 5.00 |
| 32 | 5.00 |
| 33 | 5.00 |
| 34 | 2.50 |
| 35 | 2.50 |
| 36 | 5.00 |
| 37 | 5.00 |
| 38 | 5.00 |
| 39 | 0.60 |
| 41 | 2.50 |
| 43 | 2.50 |
| 44 | 2.50 |
| 45 | 2.50 |
| 46 | >2.50 |
| 47 | 2.50 |
| 48 | 2.50 |
| 49 | 2.50 |
| 50 | 2.50 |
| 52 | 2.50 |
| 53 | >2.50 |
| 55 | >2.50 |
| 56 | >5.00 |
| 57 | >5.00 |
| 58 | 5.00 |
| 59 | >2.50 |
| 61 | 2.50 |
| 62 | >5.00 |
| 63 | >5.00 |
| 64 | >5.00 |
| 65 | 5.00 |
| 66 | 2.50 |
| 67 | 2.50 |
| 68 | 5.00 |
| 69 | 2.50 |
| 70 | 5.00 |
| 71 | >5.00 |
| 72 | 2.50 |
| 73 | >2.50 |
| 74 | 2.50 |
| 75 | 2.50 |
| 76 | >2.50 |
| 77 | 2.50 |
| 78 | 1.25 |
| 79 | 2.50 |
| 80 | >2.50 |
| 81 | 2.50 |
| 82 | 2.50 |
| 83 | >2.50 |
| 84 | >2.50 |
| 85 | 2.50 |
| 86 | 2.50 |
| 87 | 1.25 |
| 88 | 2.50 |
| 89 | 2.50 |
| 90 | 2.50 |
| 91 | 2.50 |
| 92 | 5.00 |
| 93 | 2.50 |
| 94 | 5.00 |
| 95 | 5.00 |
| 96 | 2.50 |
| 97 | 2.50 |
| 98 | 5.00 |
| 99 | 2.50 |
| 102 | 5.00 |
| 103 | >2.50 |
| 104 | 2.50 |
| 105 | 2.50 |
| 106 | 2.50 |
| 107 | >2.50 |
| 109 | 2.50 |
| 110 | >2.50 |
| 111 | >2.50 |
| 112 | 2.50 |
| 113 | >2.50 |
| 114 | 2.50 |
| 115 | >2.50 |
| 116 | 2.50 |
| 117 | >2.50 |
| 118 | 2.50 |
| 121 | >2.50 |
| 122 | >2.50 |
| 123 | 2.50 |
| 125 | 2.50 |
| 126 | 2.50 |
| 127 | >2.50 |
| 128 | 5.00 |
| 129 | 2.50 |
| 130 | 5.00 |
| 131 | 5.00 |
| 132 | 5.00 |
| 133 | >5.00 |
| 134 | 5.00 |
| 135 | 2.50 |
| 136 | 5.00 |
| 137 | >5.00 |
| 138 | >5.00 |
| 139 | 10.00 |
| 140 | 5.00 |
| 141 | >10.00 |
| 142 | 5.00 |
| 143 | 10.00 |
| 148 | >5.00 |
| 151 | 5.00 |
| 152 | >5.00 |
| 154 | 5.00 |
| 155 | >10.00 |
| 156 | >10.00 |
| 157 | >10.00 |
| 158 | >10.00 |
| 159 | >10.00 |
| 160 | 10.00 |
| 161 | >2.50 |
| 162 | >5.00 |
| 163 | 20.00 |
| 164 | 20.00 |
| 165 | >20.00 |
| 166 | 5.00 |
| 167 | 10.00 |
| 168 | 10.00 |
| 169 | 10.00 |
| 170 | 10.00 |
| 171 | >10.00 |
| 172 | 10.00 |
| 173 | 10.00 |
| 174 | 10.00 |
| 175 | 10.00 |
| 176 | >10.00 |
| 178 | >10.00 |
| 179 | >10.00 |
| 180 | >10.00 |
| 181 | 10.00 |
| 182 | 10.00 |
| 183 | >10.00 |
| 184 | >10.00 |
| 185 | 10.00 |
| 186 | >10.00 |
| 187 | >10.00 |
| 189 | >10.00 |
| 190 | >10.00 |
| 191 | >10.00 |
| 192 | >10.00 |
| 193 | >10.00 |
| 194 | 10.00 |
| 195 | >10.00 |
| 196 | >10.00 |
| 197 | >10.00 |
| 198 | >10.00 |
| 199 | >10.00 |
| 200 | >10.00 |

TABLE 23-continued

| Co. No. | LAD (mg/kg) |
|---|---|
| 201 | >10.00 |
| 202 | >10.00 |
| 203 | >10.00 |
| 204 | >10.00 |
| 205 | >10.00 |
| 207 | 10.00 |
| 208 | >10.00 |
| 209 | 5.00 |
| 210 | 20.00 |
| 212 | 20.00 |
| 213 | 20.00 |
| 214 | 20.00 |
| 215 | 20.00 |
| 216 | 20.00 |
| 217 | 10.00 |
| 219 | 20.00 |
| 220 | 20.00 |
| 221 | 10.00 |
| 222 | 20.00 |
| 223 | 5.00 |
| 224 | >10.00 |
| 227 | >10.00 |
| 228 | >10.00 |
| 229 | >10.00 |
| 230 | >10.00 |
| 231 | >10.00 |
| 232 | >10.00 |
| 233 | >10.00 |
| 234 | 10.00 |
| 235 | 5.00 |
| 236 | 5.00 |
| 237 | 5.00 |
| 238 | 5.00 |
| 239 | 10.00 |
| 240 | 10.00 |
| 241 | 10.00 |
| 242 | >10.00 |
| 243 | 10.00 |
| 244 | 10.00 |
| 245 | 10.00 |
| 246 | 10.00 |
| 247 | 10.00 |
| 248 | 2.50 |
| 249 | 5.00 |
| 250 | >10.00 |
| 251 | 10.00 |
| 252 | >10.00 |
| 253 | >5.00 |
| 254 | >5.00 |
| 255 | 5.00 |
| 256 | >2.50 |
| 261 | >10.00 |
| 262 | 20.00 |
| 263 | >10.00 |
| 264 | >10.00 |
| 266 | >10.00 |
| 267 | >10.00 |
| 268 | >10.00 |
| 269 | >10.00 |
| 270 | >10.00 |
| 271 | 10.00 |
| 272 | >10.00 |
| 273 | >10.00 |
| 274 | >10.00 |
| 275 | >10.00 |
| 276 | >10.00 |
| 277 | >5.00 |
| 278 | 2.50 |
| 279 | 2.50 |
| 280 | >2.50 |
| 281 | >2.50 |
| 283 | 2.50 |
| 284 | 2.50 |
| 285 | >2.50 |
| 286 | >2.50 |
| 287 | >2.50 |
| 288 | >2.50 |

TABLE 23-continued

| Co. No. | LAD (mg/kg) |
|---|---|
| 289 | >2.50 |
| 290 | 2.50 |
| 291 | >2.50 |
| 292 | >2.50 |
| 293 | >2.50 |
| 294 | >2.50 |
| 295 | >2.50 |
| 297 | >2.50 |
| 300 | >2.50 |
| 301 | >2.50 |
| 302 | >2.50 |
| 304 | >2.50 |
| 306 | >2.50 |
| 307 | >2.50 |
| 308 | >2.50 |
| 309 | >2.50 |
| 310 | 2.50 |
| 311 | 2.50 |
| 312 | >2.50 |
| 313 | 2.50 |
| 314 | >2.50 |
| 315 | >2.50 |
| 316 | 5.00 |
| 317 | >5.00 |
| 318 | >2.50 |
| 319 | >5.00 |
| 320 | 5.00 |
| 322 | >2.50 |
| 324 | >2.50 |
| 325 | 2.50 |
| 326 | >2.50 |
| 327 | >2.50 |
| 328 | >2.50 |
| 329 | >2.50 |
| 330 | 2.50 |
| 332 | >2.50 |
| 333 | >2.50 |
| 337 | 2.50 |
| 338 | >2.50 |
| 339 | >2.50 |
| 340 | 2.50 |
| 341 | >2.50 |
| 342 | >2.50 |
| 343 | >2.50 |
| 346 | >5.00 |
| 347 | >5.00 |
| 348 | >2.50 |
| 349 | >2.50 |
| 350 | >2.50 |
| 351 | >5.00 |
| 352 | >5.00 |
| 353 | >5.00 |
| 354 | >5.00 |
| 355 | >10.00 |
| 356 | >10.00 |
| 357 | >10.00 |
| 358 | >10.00 |
| 359 | >10.00 |
| 360 | 2.50 |
| 361 | 10.00 |
| 362 | 10.00 |
| 363 | >10.00 |
| 364 | 2.50 |
| 365 | 10.00 |
| 366 | >10.00 |
| 367 | 2.50 |
| 368 | 2.50 |
| 369 | 10.00 |
| 370 | >10.00 |
| 371 | 10.00 |
| 372 | 5.00 |
| 374 | 2.50 |
| 375 | >5.00 |
| 376 | 2.50 |
| 378 | 2.50 |
| 379 | >2.50 |
| 380 | >2.50 |

TABLE 23-continued

| Co. No. | LAD (mg/kg) |
|---|---|
| 381 | >2.50 |
| 383 | >2.50 |
| 384 | >2.50 |
| 385 | >2.50 |
| 386 | >2.50 |
| 387 | >2.50 |
| 389 | >2.50 |
| 390 | >2.50 |
| 391 | >5.00 |
| 392 | >5.00 |
| 393 | 5.00 |
| 394 | >2.50 |
| 395 | >5.00 |
| 396 | >2.50 |
| 397 | >2.50 |
| 398 | >5.00 |
| 400 | >2.50 |
| 401 | >2.50 |
| 402 | >5.00 |
| 403 | >5.00 |
| 404 | 5.00 |
| 405 | 5.00 |
| 406 | >5.00 |
| 407 | >5.00 |
| 408 | >5.00 |
| 409 | 5.00 |
| 410 | >5.00 |
| 411 | 2.50 |
| 412 | >2.50 |
| 413 | 5.00 |
| 414 | 5.00 |
| 416 | >5.00 |
| 417 | >5.00 |
| 419 | >5.00 |
| 420 | >20.00 |
| 421 | >10.00 |
| 422 | >10.00 |
| 423 | 20.00 |
| 424 | >10.00 |
| 425 | >10.00 |
| 426 | >10.00 |
| 427 | 2.50 |
| 428 | >2.50 |
| 429 | >2.50 |
| 431 | >2.50 |
| 432 | >2.50 |
| 433 | >2.50 |
| 434 | >2.50 |
| 435 | >2.50 |
| 436 | >5.00 |
| 437 | >2.50 |
| 438 | >2.50 |
| 439 | >2.50 |
| 445 | >20.00 |
| 454 | >20.00 |
| 455 | 2.50 |
| 456 | >20.00 |
| 457 | >20.00 |
| 458 | 5.00 |
| 459 | 20.00 |
| 460 | >20.00 |
| 461 | 10.00 |
| 462 | 20.00 |
| 463 | 20.00 |
| 464 | >20.00 |
| 465 | >20.00 |
| 466 | >20.00 |
| 467 | >20.00 |
| 468 | 10.00 |
| 469 | >10.00 |
| 470 | >20.00 |
| 471 | >10.00 |
| 472 | >20.00 |
| 473 | >10.00 |
| 474 | >10.00 |
| 475 | >10.00 |
| 476 | >10.00 |
| 477 | >10.00 |
| 478 | 2.50 |
| 479 | >10.00 |
| 480 | 10.00 |
| 481 | 10.00 |
| 482 | 10.00 |
| 483 | >5.00 |
| 484 | >5.00 |
| 485 | 5.00 |
| 486 | 5.00 |
| 487 | >5.00 |
| 489 | 2.50 |
| 490 | 2.50 |
| 492 | >2.50 |
| 493 | >2.50 |
| 494 | >2.50 |
| 495 | >2.50 |
| 497 | >20.00 |
| 502 | 5.00 |
| 511 | >20.00 |
| 512 | >20.00 |
| 513 | >20.00 |
| 514 | >20.00 |
| 515 | >20.00 |
| 518 | >10.00 |
| 519 | >10.00 |
| 521 | 10.00 |
| 524 | 20.00 |
| 532 | >10.00 |
| 551 | >2.50 |
| 552 | >2.50 |
| 554 | 2.50 |
| 555 | >2.50 |
| 557 | >5.00 |
| 558 | >5.00 |
| 560 | >5.00 |
| 562 | 5.00 |
| 566 | 5.00 |
| 570 | >5.00 |
| 572 | >5.00 |
| 574 | 20.00 |
| 575 | 20.00 |
| 576 | 10.00 |
| 577 | 10.00 |
| 578 | >10.00 |
| 579 | 10.00 |
| 580 | 10.00 |
| 581 | 20.00 |
| 582 | >10.00 |
| 583 | 10.00 |
| 584 | 10.00 |
| 585 | 10.00 |
| 586 | >10.00 |
| 587 | >10.00 |
| 588 | 10.00 |
| 589 | 10.00 |
| 590 | >10.00 |
| 591 | >10.00 |
| 592 | >10.00 |
| 593 | >10.00 |
| 594 | >10.00 |
| 595 | 10.00 |
| 596 | 10.00 |
| 597 | >10.00 |
| 598 | >10.00 |
| 599 | >20.00 |
| 600 | >10.00 |
| 601 | 10.00 |
| 602 | >10.00 |
| 603 | >10.00 |
| 604 | >10.00 |
| 605 | >10.00 |
| 606 | >10.00 |
| 608 | >10.00 |
| 609 | 10.00 |
| 610 | >10.00 |
| 611 | 10.00 |

TABLE 23-continued

| Co. No. | LAD (mg/kg) |
|---|---|
| 612 | 10.00 |
| 613 | >20.00 |
| 614 | >20.00 |
| 615 | >20.00 |
| 618 | >20.00 |
| 619 | >20.00 |
| 621 | 1.25 |
| 623 | >5.00 |
| 624 | >2.50 |
| 626 | 2.50 |
| 627 | >2.50 |
| 628 | >2.50 |
| 629 | >2.50 |
| 630 | >2.50 |
| 631 | >2.50 |
| 632 | >2.50 |
| 636 | 2.50 |
| 638 | >2.50 |
| 639 | 2.50 |
| 640 | >2.50 |
| 642 | 2.50 |
| 644 | 2.50 |
| 645 | >5.00 |
| 646 | 5.00 |
| 647 | >5.00 |
| 649 | 5.00 |
| 650 | 10.00 |
| 651 | 5.00 |
| 652 | 10.00 |
| 653 | 5.00 |
| 654 | 5.00 |
| 655 | >10.00 |
| 656 | 10.00 |
| 657 | >10.00 |
| 658 | >10.00 |
| 659 | >10.00 |
| 660 | >10.00 |
| 661 | >10.00 |
| 662 | 5.00 |
| 663 | 2.50 |
| 664 | 5.00 |
| 665 | 2.50 |
| 666 | 2.50 |
| 667 | 5.00 |
| 668 | 5.00 |
| 669 | 5.00 |
| 670 | >2.50 |
| 679 | >20.00 |
| 680 | >20.00 |
| 681 | >20.00 |
| 682 | >20.00 |
| 686 | >10.00 |
| 690 | >10.00 |
| 692 | >10.00 |
| 695 | >10.00 |
| 696 | >10.00 |
| 697 | 10.00 |
| 698 | 20.00 |
| 700 | 5.00 |
| 704 | >5.00 |
| 705 | >5.00 |
| 706 | 5.00 |
| 707 | 5.00 |
| 708 | >5.00 |
| 709 | 5.00 |
| 710 | 2.50 |
| 711 | 5.00 |
| 712 | 5.00 |
| 713 | 2.50 |
| 714 | 2.50 |
| 715 | >2.50 |
| 716 | >2.50 |
| 717 | >2.50 |
| 718 | 2.50 |
| 720 | >2.50 |
| 721 | >2.50 |
| 722 | 5.00 |
| 723 | 5.00 |
| 724 | 2.50 |
| 725 | 5.00 |
| 726 | 5.00 |
| 727 | >10.00 |
| 728 | 5.00 |
| 729 | 2.50 |
| 730 | >10.00 |
| 732 | >10.00 |
| 733 | >10.00 |
| 734 | 10.00 |
| 735 | 10.00 |
| 736 | >10.00 |
| 737 | >10.00 |
| 738 | 10.00 |
| 739 | >10.00 |
| 740 | 20.00 |
| 741 | 10.00 |
| 742 | 10.00 |
| 743 | >10.00 |
| 745 | >5.00 |
| 746 | >5.00 |
| 749 | >20.00 |
| 751 | 10.00 |
| 753 | >10.00 |
| 754 | 10.00 |
| 758 | >5.00 |
| 761 | >5.00 |
| 762 | >5.00 |
| 763 | >5.00 |
| 764 | >5.00 |
| 766 | >2.50 |
| 768 | >2.50 |
| 772 | >5.00 |
| 773 | >10.00 |
| 774 | 10.00 |
| 776 | >20.00 |
| 778 | 5.00 |
| 782 | 2.50 |
| 783 | 5.00 |
| 784 | >5.00 |
| 785 | 5.00 |

D. COMPOSITION EXAMPLES

The following formulations exemplify typical pharmaceutical compositions suitable for systemic or topical administration to animal and human subjects in accordance with the present invention. "Active ingredient" (A.I.) as used throughout these examples relates to a compound of formula (I) or a pharmaceutically acceptable acid addition salt thereof.

Example D.1

Oral Solution 9 g of methyl 4-hydroxybenzoate and 1 g of propyl 4-hydroxy-benzoate were dissolved in 4 l of boiling purified water. In 3 l of this solution were dissolved first 10 g of 2,3-dihydroxybutanedioic acid and thereafter 20 g of A.I. The latter solution was combined with the remaining part of the former solution and 12 l 1,2,3-propane-triol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of A.I. per teaspoonful (5 ml). The resulting solution was filled in suitable containers.

Example D.2

Oral Drops 500 g of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example D.3

Capsules 20 g of A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelatin capsules, each comprising 20 mg of A.I.

Example D.4

Injectable Solution 0.5 mg A.I. 1, 50 mg glucose anhydrous and 0.332 ml concentrated hydrochloric acid were mixed with 0.8 ml water for injections. Sodium hydroxide was added until pH=3.2±0.1 and water was added to 1 ml. The solution was sterilized and filled in sterile containers.

Example D.5

Film-coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90®) in about 200 ml of water. The wet powder mixture was sieved, dried and sieved again. Then there was added 100 g microcrystalline cellulose (Avicel®) and 15 g hydrogenated vegetable oil (Sterotex®). The whole was mixed well and compressed into tablets, giving 10,000 tablets, each comprising 10 mg of the active ingredient.

Coating

To a solution of 10 g methyl cellulose (Methocel 60 HG®) in 75 ml of denatured ethanol there was added a solution of 5 g of ethyl cellulose (Ethocel 22 cps®) in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension (Opaspray K-1-2109®) and the whole was homogenated. The tablet cores were coated with the thus obtained mixture in a coating apparatus.

Example D.6

2% Cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70 to 75° C. while using a homogenizer for liquids. The resulting emulsion is allowed to cool to below 25° C. while continuously mixing. A solution of 20 mg A.I., 1 mg polysorbate 80 and purified water and a solution of 2 mg sodium sulfite anhydrous in purified water are next added to the emulsion while continuously mixing. The cream, 1 g of the A.I. is homogenized and filled into suitable tubes.

Example D.7

2% Topical Gel

To a solution of 200 mg hydroxypropyl β-cyclodextrine in purified water is added 20 mg of A.I. while stirring. Hydrochloric acid is added until complete dissolution and then sodium hydroxide is added until pH 6.0. This solution is added to a dispersion of 10 mg carrageenan PJ in 50 mg propylene glycol while mixing. While mixing slowly, the mixture is heated to 50° C. and allowed to cool to about 35° C. whereupon 50 mg ethyl alcohol 95% (v/v) is added. The rest of the purified water q.s. ad 1 g is added and the mixture is mixed to homogenous.

Example D.8

2% Topical Cream

To a solution of 200 mg hydroxypropyl β-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

Example D.9

2% Liposome Formulation

A mixture of 2 g A.I. microfine, 20 g phosphatidyl choline, 5 g cholesterol and 10 g ethyl alcohol is stirred and heated at 55–60° C. until complete dissolution and is added to a solution of 0.2 methyl paraben, 0.02 g propyl paraben, 0.15 g disodium edetate and 0.3 g sodium chloride in purified water while homogenizing. 0.15 g Hydroxypropylmethylcellulose in purified water ad 100 g is added and the mixing is continued until swelling is complete.

The invention claimed is:
1. A compound having the formula

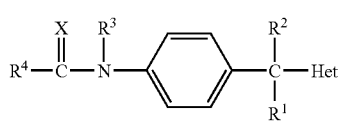

(I)

a N-oxide, a pharmaceutically acceptable addition salt or a stereochemically isomeric form thereof, wherein:

X represents —O—, —S— or —NR$^3$—;

R$^1$ and R$^2$ taken together form a bivalent radical of formula —R$^1$—R$^2$— wherein —R$^1$—R$^2$— represents —(CH$_2$)$_n$— wherein n is 2, 3, 4, 5 or 6;

R$^3$ represents hydrogen, C$_{1-6}$alkyl, aryl, Het$^1$ or C$_{1-6}$alkyl substituted with aryl or Het$^1$;

R$^4$ represents hydrogen; hydroxy; mercapto; C$_{1-6}$alkyloxy; C$_{1-6}$alkylthio; aryloxy; arylthio; Het$^1$-oxy; Het$^1$-thio; C$_{1-12}$alkyl optionally substituted with one, two or three substituents each independently selected from halo, hydroxy, mercapto, C$_{1-6}$alkyloxy, C$_{1-6}$alkylthio, aryloxy, arylthio, Het$^1$-oxy, Het$^1$-thio, C$_{3-7}$cycloalkyl optionally substituted with hydroxycarbonylC$_{1-6}$alkyl, carboxyl, C$_{1-6}$alkyloxycarbonyl, arylC$_{1-6}$alkyloxy, arylC$_{1-6}$alkylthio, aryl, Het$^1$; C$_{2-8}$alkenyl optionally substituted with one, two or three substituents selected from halo, C$_{3-7}$cycloalkyl, aryl, Het$^1$; C$_{2-8}$alkynyl optionally substituted with halo, C$_{3-7}$cycloalkyl, aryl; C$_{3-7}$cycloalkyl optionally substituted with C$_{1-6}$alkyl or aryl; C$_{5-7}$cycloalkenyl optionally substituted with C$_{1-6}$alkyl or aryl; aryl; Het$^1$; or -Alk-NR$^3$R$^5$ (i)

or

—NR$^3$R$^5$ (ii)

wherein Alk represents C$_{1-6}$alkanediyl; and

R$^5$ represents hydrogen, C$_{1-6}$alkyl, aryl, Het$^1$, (aryl or Het$^1$)C$_{1-6}$alkyl, (aryl or Het$^1$)carbonyl or (aryl or Het$^1$)C$_{1-6}$alkyloxycarbonyl;

aryl represents indanyl, indenyl, naphtyl, 5,6,7,8-tetrahydro-2-naphtalenyl phenyl; said indanyl, indenyl, naphtyl or phenyl may be substituted with one, two, three, four or five substituents each independently selected from hydroxy, halo, nitro, cyano, amino, azido, mono- or di(C$_{1-6}$alkyl)amino, C$_{1-6}$alkylcarbonylamino, C$_{1-6}$alkyl, polyhaloC$_{1-6}$alkyl, hydroxyC$_{1-6}$alkyl, phenyl, phenyloxy, phenylC$_{1-6}$alkyloxy, pyridinylC$_{1-6}$alkyloxy, C$_{1-6}$alkyloxy, formyl, carboxyl and C$_{1-6}$alkylcarbonyl; or two adjacent carbon atoms on said phenyl may be substituted by a single bivalent radical having the formula C$_{1-12}$alkanediyl or polyhaloC$_{1-12}$alkanediyl;

Het represents an unsaturated heterocycle which is selected from pyrrolyl, pyrazolyl, imidazolyl, triazolyl, tetrazolyl and pyridinyl; each of said unsaturated heterocycles may optionally be substituted with amino, mercapto, C$_{1-6}$alkyl, C$_{1-6}$alkylthio or aryl; and Het$^1$ represents a monocyclic heterocycle selected from pyrrolidinyl, pyrrolyl, pyrazolyl, imidazolyl, 1,3,4-triazolyl, 1,2,4-triazolyl, tetrahydrofuranyl, furanyl, thiolanyl, thienyl, dioxolanyl, isoxazolyl, oxazolyl, isothiazolyl, thiazolyl, isoxazolidinyl, oxazolidinyl, isothiazolidinyl, thiazolidinyl, piperidinyl, pyridinyl, piperazinyl, pyridazinyl, pyrimidinyl, pyrazinyl, 1,2,3-triazinyl, 1,2,4-triazinyl, tetrahydropyranyl, pyranyl, morpholinyl and dioxanyl; each of said monocyclic heterocycles may be optionally substituted with one or two substituents each independently selected from C$_{1-4}$alkyl, hydroxy, amino, halo, aryl, arylcarbonyl or C$_{1-4}$alkyloxycarbonyl; or a bicyclic heterocycle selected from indolinyl, indolyl, indazolyl, benzimidazolyl, benzotriazolyl, benzofuranyl, benzothienyl, 2H-1-benzopyranyl, 3,4-dihydro-2H-1-benzopyranyl, benzthiazolyl, isoquinolinyl, quinolinyl, 3,4-dihydroquinolinyl, cinnolinyl, quinazolinyl, quinoxalinyl, chromanyl, 1,4-benzodioxinyl, 1,4-benzothianyl, benzodioxanyl and benzodioxolanyl; each of said bicyclic heterocycles may be substituted with one or two substituents each independently selected from C$_{1-4}$alkyl, hydroxy, amino, halo, aryl, arylcarbonyl or C$_{1-4}$alkyloxycarbonyl.

2. A compound according to claim 1 wherein R$^3$ is hydrogen; X is O and R$^4$ is aryl or C$_{1-12}$alkyl optionally substituted with one, two or three substituents each independently selected from halo, hydroxy, C$_{1-6}$alkyloxy, C$_{1-6}$alkylthio, aryloxy, arylthio, Het$^1$-thio, C$_{3-7}$cycloalkyl optionally substituted with hydroxycarbonylC$_{1-6}$alkyl, carboxyl, C$_{1-6}$alkyloxycarbonyl, arylC$_{1-6}$alkylthio, aryl, Het$^1$; or a radical of formula (ii).

3. A pharmaceutical composition comprising a pharmaceutically acceptable carrier and, as active ingredient, a therapeutically effective amount of a compound as claimed in claim 1.

4. A process of preparing a pharmaceutical composition comprising intimately mixing a pharmaceutically acceptable carrier with a therapeutically effective amount of a compound as claimed in claim 1.

5. A pharmaceutical composition comprising a pharmaceutically acceptable carrier and as active ingredients (a) an effective amount of retinoic acid, a derivative thereof or a stereochemically isomeric form thereof, and (b) an effective amount of a compound of formula (I) according to claim 1.

6. A pharmaceutical composition comprising a pharmaceutically acceptable carrier and as active ingredients (a) an effective amount of calcitriol or a prodrug thereof, and (b) an effective amount of a compound of formula (I) according to claim 1.

7. A product containing (a) a pharmaceutical composition containing an effective amount of retinoic acid, a derivative thereof or a stereochemically isomeric form thereof and a pharmaceutical acceptable carrier, and (b) a pharmaceutical composition containing an effective amount of a compound of formula (I) according to claim 1, and a pharmaceutical acceptable carrier, as a combined preparation for simultaneous, separate or sequential use in dermatological or oncological disorders.

8. A product containing (a) a pharmaceutical composition containing an effective amount of calcitriol or a prodrug thereof and a pharmaceutical acceptable carrier, and (b) a pharmaceutical composition containing an effective amount of a compound of formula (I) according to claim 1, and a pharmaceutical acceptable carrier, as a combined preparation for simultaneous, separate or sequential use in dermatological or oncological disorders.

9. A product containing a) a pharmaceutical composition comprising a pharmaceutically effective amount of a compound according to claim 1 and a pharmaceutically acceptable carrier; and b) a pharmaceutical composition comprising a pharmaceutically effective amount of an antineoplastic agent and a pharmaceutically acceptable carrier, as a combined preparation for simultaneous, separate or sequential use in dermatological or oncological disorders.

10. A method of treating a disorder selected from the group consisting of an oncology disorder and a keratinization disorder in a warm-blooded animal in need thereof comprising administering to the warm-blooded animal an effective amount of a compound of formula (I) as claimed in claim 1.

* * * * *